US008852903B2

(12) United States Patent
Eliot et al.

(10) Patent No.: US 8,852,903 B2

(45) Date of Patent: Oct. 7, 2014

(54) CO-METABOLISM OF FRUCTOSE AND GLUCOSE IN MICROBIAL PRODUCTION STRAINS

(75) Inventors: Andrew C. Eliot, Wilmington, DE (US); Anthony A. Gatenby, Wilmington, DE (US); John S. Chapman, New London Township, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 339 days.

(21) Appl. No.: 12/906,537

(22) Filed: Oct. 18, 2010

(65) Prior Publication Data

US 2011/0256598 A1 Oct. 20, 2011

Related U.S. Application Data

(60) Provisional application No. 61/254,217, filed on Oct. 23, 2009.

(51) Int. Cl.

| | |
|---|---|
| ***C12P 7/42*** | (2006.01) |
| ***C12P 7/18*** | (2006.01) |
| ***C12P 7/20*** | (2006.01) |
| ***C12N 1/20*** | (2006.01) |
| ***C07K 14/245*** | (2006.01) |

(52) U.S. Cl.

CPC ................. *C07K 14/245* (2013.01); *C12P 7/18* (2013.01); *C12P 7/20* (2013.01); *C12P 7/42* (2013.01)

USPC ........ 435/146; 435/158; 435/159; 435/252.2; 435/252.3; 435/252.31; 435/252.32; 435/252.33; 435/252.34; 435/252.35

(58) Field of Classification Search

USPC ................... 435/146, 158, 159, 252.2, 252.3, 435/252.31, 252.32, 252.33, 252.34, 252.35

See application file for complete search history.

(56) References Cited

U.S. PATENT DOCUMENTS

| | | | | |
|---|---|---|---|---|
| 5,686,276 | A | 11/1997 | Laffend et al. | |
| 6,013,494 | A | 1/2000 | Nakamura et al. | |
| 6,136,576 | A | 10/2000 | Diaz-Torres et al. | |
| 6,514,733 | B1 | 2/2003 | Emptage et al. | |
| 7,005,291 | B1 | 2/2006 | Nair et al. | |
| 7,132,527 | B2 | 11/2006 | Payne et al. | |
| 7,371,558 | B2 | 5/2008 | Cervin et al. | |
| 7,524,660 | B2 | 4/2009 | Caimi et al. | |
| 2008/0176302 | A1 * | 7/2008 | Cervin et al. | 435/158 |
| 2009/0209011 | A1 * | 8/2009 | Rybak et al. | 435/107 |

FOREIGN PATENT DOCUMENTS

| | | |
|---|---|---|
| WO | 2006135075 | 12/2006 |

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Gunn et al., "Identification of a novel sugar-H+ symport protein, FucP, for transport of L-fucose into *Escherichia coli*", Molecular Microbiology (1994) 12(5), pp. 799-809.

Kornberg et al., "A route for fructose utilization by *Escherichia coli* involving the fucose regulon", PNAS (2006) 103(51), pp. 19496-19499.

Eliot et al., U.S. Appl. No. 12/815,461, filed Jun. 15, 2010.

* cited by examiner

*Primary Examiner* — Ganapathirama Raghu

(57) ABSTRACT

Recombinant microorganisms having an improved ability to co-metabolize in medium both fructose and glucose are described. The recombinant microorganisms comprise a promoter operably linked to a native or non-native nucleotide sequence that encodes a fucose: H+ symporter polypeptide. The recombinant microorganisms are useful for the production of a variety of products including glycerol and glycerol derivatives such as 1,3-propanediol and 3-hydroxypropionic acid.

8 Claims, No Drawings

CO-METABOLISM OF FRUCTOSE AND GLUCOSE IN MICROBIAL PRODUCTION STRAINS

FIELD OF THE INVENTION

The invention relates to the fields of microbiology and molecular biology. More specifically, recombinant microorganisms having an improved ability to co-metabolize fructose and glucose, and methods of utilizing such recombinant microorganisms are provided.

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of fructose and mixed feedstocks containing fructose and other sugars as carbohydrate sources for microbial production systems would be more commercially desirable because these materials are readily available at a lower cost. Desirable commercial feedstocks contain non-glucose breakdown products of starch or a variety of sugars such as fructose, sucrose, and xylose. Low cost feedstock derived from sucrose generally contains fructose and glucose in addition to sucrose.

A production microorganism can function more efficiently when it can utilize any fructose present in a mixed feedstock. Therefore, when a production microorganism does not have the ability to utilize fructose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars, including fructose. Thus, when a production microorganism cannot utilize fructose as a carbohydrate source, it is desirable to engineer the microorganism so that it can utilize fructose.

Caimi et al. (U.S. Pat. No. 7,524,660) describe a process for the utilization of fructose by PTS minus microorganisms. The process includes expressing increased fructokinase activity in the microorganisms and optionally, expressing a galactose-proton symporter to increase the fructose transport capacity of the microorganisms. However, there is still a need for further improved fructose utilization in microbial production strains, particularly in the presence of glucose.

SUMMARY OF THE INVENTION

In one embodiment the invention provides a recombinant microorganism comprising a promoter operably linked to a native or non-native nucleotide sequence selected from the group consisting of:

(a) a nucleotide sequence encoding a fucose:H+ symporter polypeptide, wherein the polypeptide has at least 70% amino acid identity, based on the Clustal V method of alignment, when compared to an amino acid sequence as set forth in SEQ ID NO:2, SEQ ID NO:26, SEQ ID NO:28, or SEQ ID NO:30;

(b) a nucleotide sequence encoding a fucose:H+ symporter polypeptide wherein the nucleotide sequence has at least 70% sequence identity, based on the BLASTN method of alignment, when compared to a nucleotide sequence as set forth in SEQ ID NO:1, SEQ ID NO:25, SEQ ID NO:27, or SEQ ID NO:29; and (c) a nucleotide sequence encoding a fucose:H+ symporter polypeptide, wherein the nucleotide sequence hybridizes under stringent conditions to a nucleotide sequence as set forth in SEQ ID NO:1, SEQ ID NO:25, SEQ ID NO:27, or SEQ ID NO:29;

wherein the promoter is one that is not normally associated with the nucleotide sequence encoding a fucose:H+ symporter polypeptide and further wherein the recombinant microorganism has an improved ability to co-metabolize in medium both fructose and glucose.

In a second embodiment, the invention provides an improved method for producing 1,3-propanediol, glycerol, or 3-hydroxypropionic acid from a microorganism, said method comprising:

a) culturing the recombinant microorganism of any of claims 1-5 in the presence of a carbon source comprising fructose and glucose; and b) optionally, recovering the 1,3-propanediol, glycerol, or 3-hydroxypropionic acid produced in (a).

In a third embodiment, the invention provides a process for reducing the level of fructose in a fermentation medium comprising:

a) culturing the recombinant microorganism of any of claims 1-5 in the presence of fructose and glucose; and b) optionally, determining the level of fructose remaining in the fermentation medium.

The recombinant microorganism can be selected from the group consisting *Escherichia, Streptococcus, Agrobacterium, Bacillus, Corynebacterium, Lactobacillus, Clostridium, Gluconobacter, Saccharomyces, Kluyveromyces, Aspergillus, Pichia, Rhizopus, Citrobacter, Enterobacter, Klebsiella, Aerobacter, Schizosaccharomyces, Zygosaccharomyces, Candida, Hansenula, Debaryomyces, Mucor, Torulopsis, Methylobacter, Salmonella, Streptomyces*, and *Pseudomonas*.

In another aspect, the recombinant microorganism can be PTS minus and/or also has improved fructokinase activity.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a bis), and Section 208 and Annex C of the Administrative Instructions). The symbols and format used for nucleotide and amino acid sequence data comply with the rules set forth in 37 C.F.R. §1.822.

TABLE A

Summary of Gene and Protein SEQ ID Numbers

| Gene | Coding Sequence SEQ ID NO: | Encoded Protein SEQ ID NO: |
|---|---|---|
| fucP from *Escherichia coli* | 1 | 2 |
| GPD1 from *Saccharomyces cerevisiae* | 3 | 4 |
| GPD2 from *Saccharomyces cerevisiae* | 5 | 6 |
| GPP1 from *Saccharomyces cerevisiae* | 7 | 8 |
| GPP2 from *Saccharomyces cerevisiae* | 9 | 10 |
| dhaB1 from *Klebsiella pneumoniae* | 11 | 12 |
| dhaB2 from *Klebsiella pneumoniae* | 13 | 14 |
| dhaB3 from *Klebsiella pneumoniae* | 15 | 16 |
| aldB from *Escherichia coli* | 17 | 18 |
| aldA from *Escherichia coli* | 19 | 20 |

TABLE A-continued

| Summary of Gene and Protein SEQ ID Numbers | | |
|---|---|---|
| Gene | Coding Sequence SEQ ID NO: | Encoded Protein SEQ ID NO: |
| aldH from *Escherichia coli* | 21 | 22 |
| galP from *Escherichia coli* | 23 | 24 |
| fucP from *Klebsiella pneumoniae* | 25 | 26 |
| fucP from *Xanthomonas campestris* | 27 | 28 |
| fucP from *Salmonella enterica* | 29 | 30 |
| scrK from *Agrobacterium tumefaciens* | 31 | 32 |
| scrK from *Streptococcus mutans* | 33 | 34 |
| cscK from *Escherichia coli* | 35 | 36 |
| cscK from *Enterococcus faecalis* | 37 | 38 |
| HXK1 from *Saccharomyces cerevisiae* | 39 | 40 |
| HXK2 from *Saccharomyces cerevisiae* | 41 | 42 |
| dhaT from *Klebsiella pneumoniae* | 43 | 44 |

SEQ ID NO:45 is the nucleotide sequence of the coding region of the dhaX gene from *Klebsiella pneumoniae*.

SEQ ID NO:46 is the nucleotide sequence of plasmid pSYCO101.

SEQ ID NO:47 is the nucleotide sequence of plasmid pSYCO103.

SEQ ID NO:48 is the nucleotide sequence of plasmid pSYCO106.

SEQ ID NO:49 is the nucleotide sequence of plasmid pSYCO109.

SEQ ID NO:50 is the nucleotide sequence of plasmid pSYCO400/AGRO.

SEQ ID NOs:51-54 are the nucleotide sequences of primers used to construct the fucP overexpression plasmids described in Example 1 herein.

SEQ ID NO:55 is the nucleotide sequence of plasmid pMTP1.5fucP.

SEQ ID NO:56 is the nucleotide sequence of plasmid pMTP1.20fucP. SEQ ID NO:57 is the nucleotide sequence of a synthetic linker described in Example 1 herein.

SEQ ID NO:58 is the nucleotide sequence of plasmid pMTP1.6fucP.

SEQ ID NOs:59, 60, 62, 63, 65, and 66 are the nucleotide sequences of primers used to construct the fucP overexpression plasmids described in Example 2 herein.

SEQ ID NO:61 is the nucleotide sequence of plasmid pMTP1.5KpfucP.

SEQ ID NO:64 is the nucleotide sequence of plasmid pMTP1.5XcfucP.

SEQ ID NO:67 is the nucleotide sequence of plasmid pMTP1.5SefucP.

SEQ ID NOs:68-71 are the nucleotide sequences of primers used to construct strain TTab described in Examples 3-9 herein.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "fucose:H+ symporter polypeptide" refers to a polypeptide that mediates the transport of L-fucose into certain microorganisms such as *Escherichia coli* (Gunn et al. *Molec. Microbiol.* 12:799-809, 1994) and also transports fructose (Kornberg et al. *Proc. Natl. Acad. Sci. U.S.A.* 103: 19496-19499, 2006). The *Escherichia coli* fucose:H+ symporter polypeptide, set forth in SEQ ID NO:2, is encoded by the fucP gene, the coding sequence of which is set forth in SEQ ID NO:1.

The term "improved ability to co-metabolize in medium fructose and glucose" means that the recombinant microorganism comprising a fucose:H+ symporter polypeptide disclosed herein co-metabolizes fructose and glucose to a greater extent than the host microorganism from which it is constructed. The term "co-metabolize" refers to the simultaneous utilization of fructose and glucose in medium by a microorganism.

The term "fructokinase" refers to a protein that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "Frk", "scrK", "cscK", "FK", and "KHK". Fructokinase is encoded by the scrK gene in *Agrobacterium tumefaciens* and *Streptococcus mutans*.

The term "fructokinase activity" refers to an enzymatic activity resulting in the phosphorylation of fructose, thereby providing fructose-phosphate. Fructokinase activity is found, for example, in kinases designated as EC 2.7.1.4, as well as in various hexose kinases (EC 2.7.1.3 and EC 2.7.1.1).

The term "increased fructokinase activity" refers to a fructokinase activity level which is higher than the level of activity for that enzyme in the host microorganism.

The term "glycerol derivative" refers to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:3; encoded protein sequence set forth in SEQ ID NO:4), or GPD2 (coding sequence set forth in SEQ ID NO:5; encoded protein sequence set forth in SEQ ID NO:6), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:7; encoded protein sequence set forth in SEQ ID NO:8), or GPP2 (coding sequence set forth in SEQ ID NO:9; encoded protein sequence set forth in SEQ ID NO:10).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium, Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:11, encoded protein sequence set forth in SEQ ID NO:12), gldA and dhaB; genes encoding the medium or "β" (beta) subunit include dhaB2 (coding sequence set forth in SEQ ID NO:13, encoded protein sequence set forth in SEQ ID NO:14), gldB, and dhaC; genes encoding the small or "γ" (gamma) subunit include dhaB3 (coding sequence set forth in SEQ ID NO:15, encoded protein sequence set forth in SEQ ID NO:16), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae, Citrobacter freundii*, and *Clostridium pasteurianum*. Each of these genes encode a polypeptide belonging to the family of type III alcohol dehydrogenases, which exhibits a conserved iron-binding motif, and has a preference for the $NAD^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:18), encoded by the *E. coli* gene aldB (coding sequence set forth in SEQ ID NO:17). Examples of NAD-dependent aldehyde dehydrogenases include AldA (SEQ ID NO:20), encoded by the *E. coli* gene aldA (coding sequence set forth in SEQ ID NO:19); and AldH (SEQ ID NO:22), encoded by the *E. coli* gene aldH (coding sequence set forth in SEQ ID NO:21).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyses the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+$NAD^+$ to 3-phospho-D-glyceroyl-phosphate+NADH+H. Typical of glyceraldehyde-3-phosphate dehydrogenase is EC 1.2.1.12. Glyceraldehyde-3-phosphate dehydrogenase is encoded by gapA in *E. coli.*

The terms "aerobic respiration control protein" and "ArcA" are used interchangeably herein and refer to a global regulatory protein. The aerobic respiration control protein is encoded by arcA in *E. coli.*

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli.*

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+$H_2O$. Typical of phosphogluconate dehydratase is EC 4.2.1.12. Phosphogluconate dehydratase is encoded by edd in *E. coli.*

The term "YciK" refers to a putative enzyme encoded by yciK which is translationally coupled to btuR, the gene encoding Cob(I)alamin adenosyltransferase in *E. coli.*

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:23, encoded protein sequence set forth in SEQ ID NO:24).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+$/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant microorganisms disclosed herein and, particularly, carbon sources comprising fructose and glucose. The carbon source may further comprise other monosaccharides; disaccharides, such as sucrose; oligosaccharides; or polysaccharides.

The terms "host cell" and "host microorganism" are used interchangeably herein and refer to a microorganism capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (i.e., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added.

Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al., *Comput. Appl. Biosci.* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The terms "recombinant construct", "expression construct", "chimeric construct", "construct", and "recombinant DNA construct", are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include microorganisms producing homologous proteins via recombinant technology.

Suitable host microorganisms for use in the construction of the recombinant microorganisms disclosed herein may be either prokaryotic or eukaryotic organisms. Examples of suitable host microorganisms include, but are not limited to organisms of the genera: *Escherichia, Streptococcus, Agrobacterium, Bacillus, Corynebacterium, Lactobacillus, Clostridium, Gluconobacter, Saccharomyces, Kluyveromyces, Aspergillus, Pichia, Rhizopus, Citrobacter, Enterobacter, Klebsiella, Aerobacter, Schizosaccharomyces, Zygosaccharomyces, Candida, Hansenula, Debaryomyces, Mucor, Torulopsis, Methylobacter, Salmonella, Streptomyces*, and *Pseudomonas*.

In one embodiment, the host microorganism is selected from the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces*, and *Pseudomonas*.

In another embodiment the host microorganism is selected from the genera: *Escherichia, Klebsiella, Citrobacter*, and *Aerobacter.*

In another embodiment, the host microorganism is *Escherichia coli.*

In some embodiments, the host microorganism is PTS minus. In these embodiments, the host microorganism is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported.

The term "down-regulated" refers to reduction in, or abolishment of, the activity of active protein(s), as compared to the activity of the wildtype protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, etc.

The recombinant microorganisms disclosed herein comprise a promoter operably linked to a native or non-native nucleotide sequence that encodes a fucose:H+ symporter polypeptide. Fucose:H+ symporter polypeptides mediate the transport of L-fucose into certain microorganisms such as *Escherichia coli* and also transport fructose. The *Escherichia coli* fucose:H+ symporter polypeptide, set forth in SEQ ID NO:2, is encoded by the fucP gene, the coding sequence of which set forth in SEQ ID NO:1.

The coding sequence of the *E. coli* fucP gene may be used to isolate nucleotide sequences encoding homologous fucose:H+ symporter polypeptides from the same or other microbial species. For example, homologs of the *E. coli* fucP gene may be identified using sequence analysis software, such as BLASTN, to search publically available nucleic acid sequence databases, as described in Example 2 herein. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.,* 89: 392, (1992)). For example, the nucleotide sequence encoding the *E. coli* fucose:H+ symporter polypeptide may be employed as a hybridization probe for the identification of homologs.

Additional nucleotide sequences that encode a fucose:H+ symporter polypeptide include, but are not limited to, the fucP homolog from *Klebsiella pneumoniae* (coding sequence set forth in SEQ ID NO:25), from *Xanthomonas campestris* (coding sequence set forth in SEQ ID NO:27), and from *Salmonella enterica* (coding sequence set forth in SEQ ID NO:29), which encode the polypetide sequences set forth in SEQ ID NO:26, SEQ ID NO:28, and SEQ ID NO:30, respectively.

One of ordinary skill in the art will appreciate that genes encoding fucose:H+ symporter polypeptides isolated from other sources may also be used in the recombinant microorganisms disclosed herein. Additionally, variations in the nucleotide sequences encoding a fucose:H+ symporter polypeptide may be made without affecting the amino acid sequence of the encoded polypeptide due to codon degeneracy, and that amino acid substitutions, deletions or additions that produce a substantially similar protein may be included in the encoded protein.

In one embodiment, the encoded fucose:H+ symporter polypeptide has at least 70%, more particularly at least 90%, and more particularly at least 95% amino acid identity, based on the Clustal V method of alignment, when compared to an amino acid sequence as set forth in SEQ ID NOs:2, 26, 28, or 30.

In another embodiment, the nucleotide sequence encoding the fucose:H+ symporter polypeptide has at least 70%, more particularly at least 90%, and more particularly at least 95% sequence identity, based on the BLASTN method of alignment, when compared to a nucleotide sequence as set forth in SEQ ID NOs:1, 25, 27, or 29.

In still another embodiment, the nucleotide sequence encoding the fucose:H+ symporter polypeptide hybridizes under stringent conditions, as defined above, to a nucleotide sequence as set forth in SEQ ID NOs:1, 25, 27, or 29.

Expression of a native or non-native fucose:H+ symporter polypeptide provides fructose uptake for fructose utilization by the recombinant microorganism. The endogenous level of fructose uptake is generally not high enough for optimal fructose utilization. Increased expression of a native or non-native fucose:H+ symporter polypeptide is desirable for efficient use of fructose, particularly in the presence of glucose, as disclosed herein. Expression of a native or non-native fucose:H+ symporter polypeptide may be effected using one of many methods known to one skilled in the art. For example, increased gene copy number may be provided by introducing a nucleotide sequence encoding a fucose:H+ symporter polypeptide (i.e. the coding region of a fucP gene) on a multicopy plasmid, or integrating one or more copies of the coding sequence of a fucP gene into the host genome. The introduced fucP coding region(s) that is either on a plasmid or in the genome may be expressed from a highly active promoter. The promoter is one that is not normally associated with the nucleotide sequence encoding a fucose:H+ symporter polypeptide. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*. In one embodiment, the promoter is the *Streptomyces lividans* glucose isomerase promoter or a variant thereof, described by Payne et al. (U.S. Pat. No. 7,132,527).

In some embodiments, the recombinant microorganisms disclosed herein have improved fructokinase activity. Utilization of fructose as a carbon substrate in the production of microbial products requires the phosphorylation of fructose by an enzyme with fructokinase activity, thereby providing fructose-phosphate for further metabolism. Proteins named fructokinases (designated EC 2.7.1.4) and various hexose kinases having fructose phosphorylating activity (EC 2.7.1.3 and EC 2.7.1.1) may be expressed in host microorganisms thereby providing fructose phosphorylating activity. Fructose phosphorylating activity may be exhibited by hexokinases and ketohexokinases.

Representative genes encoding enzymes from a variety of microorganisms, which may be used to produce increased fructokinase activity in a microbial production host strain are listed in Table 1. One skilled in the art will know that proteins that are substantially similar to a protein which is able to phosphorylate fructose (such as encoded by the genes listed in Table 1) may also be used.

TABLE 1

Sequences Encoding Enzymes with Fructokinase Activity

| Source | Gene Name | EC Number | Nucleotide SEQ ID NO: | Protein SEQ ID NO: |
|---|---|---|---|---|
| *Agrobacterium tumefaciens* | scrK (fructokinase) | 2.7.1.4 | 31 | 32 |
| *Streptococcus mutans* | scrK (fructokinase) | 2.7.1.4 | 33 | 34 |
| *Escherichia coli* | cscK (fructokinase) | 2.7.1.4 | 35 | 36 |
| *Enterococcus faecalis* | cscK (fructokinase) | 2.7.1.4 | 37 | 38 |
| *Saccharomyces cerevisiae* | HXK1 (hexokinase) | 2.7.1.1 | 39 | 40 |
| *Saccharomyces cerevisiae* | HXK2 (hexokinase) | 2.7.1.1 | 41 | 42 |

Endogenous fructokinases are generally expressed only at low levels, even under inducing conditions such as in the presence of sucrose or fructose. Fructokinase genes are not known to be widespread among native *E. coli* strains, and the presence of a fructokinase gene does not always guarantee functional activity. Two identified genes encoding proteins with fructokinase activity, present in a relatively small number of *E. coli* strains, are not induced by fructose. The genes enable strains to grow on sucrose and are only induced in the presence of that disaccharide (Kornberg, H., *Adv. Enz. Reg.* 42:349-360, 2002). Fructose may also be phosphorylated through the activity of a kinase that is normally active on mannose, 2-deoxyglucose and glucosamine. However, this enzyme is rarely present above trace levels in *E. coli*, even when the cells are growing (marginally) on fructose (Kornberg, H., supra). Manipulation of the expression of an endogenous sucrose utilization operon, a mannokinase gene, or other gene encoding a protein able to phosphorylate fructose may be used to enhance fructokinase activity.

As used herein, fructokinase activity is improved when it is higher than the activity found in the host microorganism. An assay of fructokinase units per milligram of protein (U/mg) in the supernatant fraction of a disrupted microorganism cell preparation can be used to determine natural and increased fructokinase activity levels. For example, in an *E. coli* strain which has a natural level of fructokinase activity of 0.62 U/mg, a level that is greater than 0.62 U/mg is an improved level. The improved fructokinase activity may be well above 0.62 U/mg, such as at 9 U/mg or higher.

Improved fructokinase activity may be achieved by methods known to one skilled in the art. These methods include methods of increasing expression from an endogenous gene, as well as methods of introducing a gene to obtain increased expression.

Either an endogenous fructokinase coding region sequence or an exogenous one, such as one listed in Table 1, may be used for high expression of fructokinase activity in a host microorganism. A fructokinase coding sequence may be isolated using PCR (see, e.g., U.S. Pat. No. 4,683,202) and primers designed to bound the desired sequence, if this sequence is known. Other methods of gene isolation are well known to one skilled in the art such as by using degenerate primers or heterologous probe hybridization. DNA molecules of the provided sequences can also be chemically synthesized or purchased from vendors such as DNA2.0 Inc. (Menlo Park, Calif.).

One of ordinary skill in the art will appreciate that genes encoding proteins having fructokinase activity isolated from other sources may also be used. Additionally, variations in the nucleotide sequences encoding a protein having fructokinase activity may be made without affecting the amino acid sequence of the encoded polypeptide due to codon degeneracy, and that amino acid substitutions, deletions or additions that produce a substantially similar protein may be included in the encoded protein.

In one embodiment, the recombinant microorganisms disclosed herein produce glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host microorganisms may be used that naturally produce glycerol. In addition, microorganisms may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host microorganism are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:3, encoded protein sequence set forth in SEQ ID NO:4) and GPD2 from *Saccharomyces cerevisiae* (coding sequence set forth in SEQ ID NO:5, encoded protein sequence set forth in SEQ ID NO:6). Suitable examples of genes encoding polypeptides having glycerol-3-phosphatase activity include, but are not limited to, GPP1 from *Saccharomyces cerevisiae* (coding sequence set forth in SEQ ID NO:7, encoded protein sequence set forth in SEQ ID NO:8) and GPP2 from *Saccharomyces cerevisiae* (coding sequence set forth in SEQ ID NO:9, encoded protein sequence set forth in SEQ ID NO:10).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In another embodiment, the recombinant microorganisms disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host microorganism or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:11), dhaB2 (coding sequence set forth in SEQ ID NO:13), and dhaB3 (coding sequence set forth in SEQ ID NO:15), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:43, encoded protein sequence set forth in SEQ ID NO:44).

Microorganisms can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host microorganism, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:

phosphoenolpyruvate carboxylase typically characterized as EC 4.1.1.31 cob(I)alamin adenosyltransferase, typically characterized as EC 2.5.1.17 non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:

aerobic respiration control protein
methylglyoxal synthase
acetate kinase
phosphotransacetylase
aldehyde dehydrogenase A
aldehyde dehydrogenase B
triosephosphate isomerase
phosphogluconate dehydratase In another embodiment, the recombinant microorganisms disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. Patent Application No. 61/187476. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:18), encoded by the *E. coli* gene aldB (coding sequence set forth in SEQ ID NO:17); AldA (SEQ ID NO:20), encoded by the *E. coli* gene aldA (coding sequence set forth in SEQ ID NO:19); and AldH (SEQ ID NO:22), encoded by the *E. coli* gene aldH (coding sequence asset forth ins SEQ ID NO:21).

Many of the modifications described above to improve 1,3-propanediol production by a recombinant microorganism can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, *Curr. Opin. Biotechnol.* (1999) 10:411; Ross, et al., *J. Bacteriol.* (1998) 180:5375; deHaseth, et al., *J. Bacteriol.* (1998) 180:3019; Smolke and Keasling, *Biotechnol. Bioeng.* (2002) 80:762; Swartz, *Curr. Opin. Biotech.* (2001) 12:195; and Ma, et al., *J. Bacteriol.* (2002) 184:5733.

Recombinant microorganisms containing the necessary changes in gene expression for co-metabolizing fructose and glucose in the production of microbial products including glycerol and glycerol derivatives, as described above, may be constructed using techniques well known in the art, some of which are exemplified in the Examples herein.

The construction of the recombinant microorganisms disclosed herein may be accomplished using a variety of vectors and transformation and expression cassettes suitable for the cloning, transformation and expression of coding regions that confer the ability to co-metabolize fructose and glucose in the production of glycerol and its derivatives in a suitable host microorganism. Suitable vectors are those which are compatible with the microorganism employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host microorganism are numerous and familiar to those skilled in the art. Virtually any promoter capable of driving expression is suitable for use herein. For example, any of the promoters listed above for use in expression of fucose:H+ symporter polypeptides may be used.

Termination control regions may also be derived from various genes native to the preferred hosts. Optionally, a termination site may be unnecessary; however, it is most preferred if included.

For effective expression of the instant enzymes, nucleotide sequences encoding the enzymes are linked operably through initiation codons to selected expression control regions such that expression results in the formation of the appropriate messenger RNA.

Particularly useful in the present invention are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from Klebsiella pneumoniae and from *Saccharomyces cerevisiae*. Each vector contains the open reading frames dhaB1, dhaB2, dhaB3, dhaX (SEQ ID NO:45), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:46, SEQ ID NO:47, SEQ ID NO:48, SEQ ID NO:49, and SEQ ID NO:50, respectively. The differences between the vectors are illustrated in the chart below [the prefix "p-" indicates a promoter; the open reading frames contained within each "( )" represent the composition of an operon]:

pSYCO101 (SEQ ID NO:46):
- p-trc (Dar1_GPP2) in opposite orientation compared to the other 2 pathway operons,
- p-1.6 long GI (dhaB1_dhaB2_dhaB3_dhaX), and
- p-1.6 long GI (orfY_orfX_orfW).

pSYCO103 (SEQ ID NO:47):
- p-trc (Dar1_GPP2) same orientation compared to the other 2 pathway operons,
- p-1.5 long GI (dhaB1_dhaB2_dhaB3_dhaX), and
- p-1.5 long GI (orfY_orfX_orfW).

pSYCO106 (SEQ ID NO:48):
- p-trc (Dar1_GPP2) same orientation compared to the other 2 pathway operons,
- p-1.6 long GI (dhaB1_dhaB2_dhaB3_dhaX), and
- p-1.6 long GI (orfY_orfX_orfW).

pSYCO109 (SEQ ID NO:49):
- p-trc (Dar1_GPP2) same orientation compared to the other 2 pathway operons,
- p-1.6 long GI (dhaB1_dhaB2_dhaB3_dhaX), and
- p-1.6 long GI (orfY_orfX).

pSYCO400/AGRO (SEQ ID NO:50):
- p-trc (Dar1_GPP2) same orientation compared to the other 2 pathway operons,
- p-1.6 long GI (dhaB1_dhaB2_dhaB3_dhaX), and
- p-1.6 long GI (orfY_orfX).
- p-1.20 short/long GI (scrK) opposite orientation compared to the pathway operons.

Once suitable expression cassettes are constructed, they are used to transform appropriate host microorganisms. Introduction of the cassette containing coding regions of, for example a fucose:H+ symporter polypeptide and fructokinase into the host cell may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host cell through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise a mixture of fructose and glucose as a carbon substrate. Other carbon substrates such as sucrose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae, Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other microorganisms, capable of de novo vitamin $B_{12}$ biosynthesis will also be suitable production cells and the addition of vitamin $B_{12}$ to these microorganisms will be unnecessary.

Typically microbial cells are grown at 25 to 40° C. in an appropriate medium containing fructose and glucose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant microorganism. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired microorganism or microorganisms and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In one embodiment, an improved method for producing 1,3-propanediol, glycerol, or 3-hydroxypropionic acid is provided. The method comprises the steps of culturing a recombinant microorganism, as described above, in the presence of a carbon source comprising fructose and glucose, and optionally recovering the 1,3-propanediol, glycerol, or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation.

In another embodiment, a process for reducing the level of fructose in a fermentation medium is provided. The process comprises the steps of culturing a recombinant microorganism, as described above, in the presence of fructose and glucose and optionally, determining the level of fructose remaining in the fermentation medium. The level of fructose remaining in the fermentation medium may be determined using methods known in the art, such as high performance liquid chromatography (HPLC), as described in Examples 3-9 herein below.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.).

The meaning of abbreviations is as follows: “s” means second(s), “min” means minute(s), “h” means hour(s), “nm” means nanometers, “μL” means microliter(s), “mL” means milliliter(s), “L” means liter(s), “mM” means millimolar, “M” means molar, “g” means gram(s), “μg” means microgram(s), “bp” means base pair(s), “kbp” means kilobase pair(s), “rpm” means revolutions per minute, “ATCC” means American Type Culture Collection, Manassas, Va., “Gluc” means glucose, “Fruc” means fructose.

Example 1

Construction of fucP Overexpression Plasmids

This Example illustrates the construction of three fucP overexpression plasmids, i.e., pMTP1.20fucP, pMTP1.5fucP, and pMTP1.6fucP.

The origin of replication of the large native plasmid pMT100, described in U.S. Patent Application Publication No. 2008/0194032, from *E. coli* strain ATCC No. 13281 was amplified by PCR using primers MTori1, set forth in SEQ ID NO:51, and MTori2, set forth in SEQ ID NO:52. A HindIII restriction enzyme recognition site was present in one of the PCR primers. The resulting PCR product was digested with the restriction enzymes DraI and HindIII and ligated to the SspI/HindIII fragment of pK194, described by Jobling and Holmes (*Nucleic Acids Res.* 18:5315, 1990), that contains a multiple cloning site and a kanamycin resistance gene. The resulting plasmid was named pMTori. To make plasmids pMTP1.20, pMTP1.5 and pMTP1.6, the EcoRI/HindIII fragment from pMTori1 was replaced with the EcoRI/HindIII fragment from the respective pMP38 plasmid, described in U.S. Pat. No. 7,132,527. The designations “1.20”, “1.5” and “1.6” refer to the variants of the glucose isomerase promoter described in U.S. Pat. No. 7,132,527. The coding sequence of the *E. coli* fucP gene, set forth in SEQ ID NO;1 was amplified by PCR from genomic DNA from *E. coli* strain MG1655 (available from The American Type Culture Collection as ATCC No: 700926) using the primer pair set forth in SEQ ID NOs:53 and 54. The resulting blunt fragment was ligated with HindIII-digested and blunted pMTP1.5 and pMTP1.20 to generate pMTP1.5fucP (SEQ ID NO:55) and pMTP1.20fucP (SEQ ID NO:56), respectively. The sequence of each plasmid was verified.

A pmel restriction site was added to pMTP1.5fucP by ligation of a synthetic linker sequence (set forth in SEQ ID NO:57) with ScaI and NotI digested pMTP1.5fucP plasmids. The synthetic linker sequence had an overhang of ccgg at the 5' end of the reverse strand. The resulting plasmid was designated as pMTP1.5fucPpmel.

The plasmid pMTP1.6fucP (SEQ ID NO: 58) was generated by digesting pMTP1.5fucPpmel and pMTP1.6 with BstEII. The larger fragment from the pMTP1.5fucPpmel digest and the smaller fragment from the pMTP1.6 digest were then ligated. The sequence of the resulting plasmid was verified.

Example 2

Cloning of Homologs of the *E. Coli* fucP Gene

This Example illustrates the identification and cloning of fucP genes from *Klebsiella pneumoniae, Xanthomonas campestris*, and *Salmonella enterica*, resulting in overexpression plasmids named pMTP1.5KpfucP, pMTP1.5XcfucP, and pMTP1.5SefucP, respectively.

Homologs of the *E. coli* fucP gene were identified by a BLAST search of publically available nucleic acid sequence databases (default settings), and three were chosen for expression in *E. coli:* the fucP gene from *Klebsiella pneumoniae* strain ATCC No: 700721, *Xanthomonas campestris* strain ATCC No: 33913 and *Salmonella enterica* strain LT2 (available as ATCC No: 15277).

The coding sequence of the *K. pneumoniae* fucP gene, set forth in SEQ ID NO:25, was amplified by PCR from genomic DNA obtained from ATCC using primers KpfucP1, set forth in SEQ ID NO:59, and KpfucP2, set forth in SEQ ID NO:60. The 5' primer contained a HindIII restriction site, and the 3' primer a HpaI site. The PCR product was digested with HindIII and HpaI and ligated with similarly digested pMTP1.5 plasmid DNA. The resulting plasmid was named "pMTP1.5KpfucP", set forth in SEQ ID NO:61, and the sequence was verified.

The coding sequence of the *X. campestris* fucP gene, set forth in SEQ ID NO:27, was amplified by PCR from genomic DNA obtained from ATCC using primers XcfucP1, set forth in SEQ ID NO:62, and XcfucP2, set forth in SEQ ID NO:63. The 5' primer contained a HindIII restriction site, and the 3' primer a HpaI site. The PCR product was digested with HindIII and ligated with pMTP1.5 plasmid DNA that had been digested with HindIII and HpaI. The resulting plasmid was named "pMTP1.5XcfucP", set forth in SEQ ID NO:64, and the sequence was verified.

The coding sequence of the *S. enterica* fucP gene, set forth in SEQ ID NO:29, was amplified by PCR from genomic DNA, isolated from whole cells using standard methods, using primers SalmfucP1, set forth in SEQ ID NO:65, and SalmfucP2, set forth in SEQ ID NO:66. The PCR product was ligated with pMTP1.5 plasmid DNA that had been digested with HindIII and treated with Klenow enzyme to generate blunt ends. The resulting plasmid was named "pMTP1.5SefucP", set forth in SEQ ID NO:67, and the sequence was verified.

Examples 3-9

Construction of Recombinant *E. Coli* Strains Comprising Nucleotide Sequences Encoding a Fucose:H+ Symporter Polypeptide These Examples illustrate the construction of recombinant *E. coli* strains that overexpress a fucP gene encoding a fucose: H+ symporter polypeptide. The improved fructose utilization of these strains in a medium containing a fructose-glucose mixture, compared to a control strain which does not overexpress a fucP gene, was also demonstrated.

*E. coli* Strain TTab pSYCO400/AGRO (a PTS Minus Strain)

Strain TTab was generated by deletion of the aldB gene from strain TT aldA, described in U.S. Pat. No. 7,371,558 (Example 17). Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:68 and SEQ ID NO:69 using pKD3 as the template. The primer SEQ ID NO:68 contains 80 by of homology to the 5'-end of aldB and 20 by of homology to pKD3. Primer SEQ ID NO:69 contains 80 by of homology to the 3' end of aldB and 20 by homology to pKD3. The PCR products were gel-purified and electroporated into MG1655/pKD46 competent cells (U.S. Pat. No. 7,371,558). Recombinant strains were selected on LB plates with 12.5 mg/L of chloroamphenicol. The deletion of the aldB gene was confirmed by PCR, using the primer pair SEQ ID NO:70 and SEQ ID NO:71. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:70 and SEQ ID NO:71 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:50), described in U.S. Pat. No. 7,524,660 (Example 4), to generate strain TTab pSYCO400/AGRO.

As described in the cited references, strain TTab is a derivative of *E. coli* strain FM5 (ATCC No. 53911) containing the following modifications:

deletion of glpK, gldA, ptsHI, crr, edd, arcA, mgsA, qor, ackA, pta, aldA and aldB genes;

upregulation of galP, glk, btuR, ppc, and yqhD genes; and downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

*E. coli* strain TTab pSYCO400/AGRO was transformed with each of the six fucP overexpression plasmids: pMTP1.20fucP, pMTP1.5fucP, pMTP1.6fucP, pMTP1.5XcfucP, pMTP1.5KpfucP, pMTP1.5SefucP. Transformants were selected by growth on LB (Luria-Bertani) agar containing 50 μg/mL of spectinomycin and 50 μg/mL of kanamycin. Individual colonies were picked and grown overnight at 34° C. with shaking (250 rpm) in LB broth with the same antibiotics. The control strain TTab pSYCO400/AGRO was grown under identical conditions with the exception of the kanamycin.

These overnight cultures were diluted into TM3 medium containing 9 g/L glucose and 1 g/L fructose to an optical density of 0.01 units measured at 550 nm. TM3 is a minimal medium containing 13.6 g/L $KH_2PO_4$, 2.04 g/L citric acid dihydrate, 2 g/L magnesium sulfate heptahydrate, 0.33 g/L ferric ammonium citrate, 0.5 g/L yeast extract, 3 g/L ammonium sulfate, 0.2 g/L $CaCl_2.2H_2O$, 0.03 g $MnSO_4.H_2O$, 0.01 g/L NaCl, 1 mg/L $FeSO_4.7H_2O$, 1 mg/L, $CoCl_2.6H_2O$, 1 mg/L $ZnSO_4.7H_2O$, 0.1 mg/L $CuSO_4.5H_2O$, 0.1 mg/L $H_3BO_4$, 0.1 mg/L $NaMoO_4.2H_2O$ and sufficient $NH_4OH$ to provide a final pH of 6.8. Vitamin $B_{12}$ was added to the medium to a concentration of 0.1 mg/L. The cultures were incubated at 34° C. with shaking (225 rpm) for 24 h. Aliquots were removed at 0, 5, 8, 11, 14, 17, 20 and 23 h after inoculation, and the concentrations of glucose, fructose, glycerol and 1,3-propanediol (PDO) in the broth were determined by high performance liquid chromatography.

Chromatographic separation was achieved using a Shodex SH1011 column (Showa Denko America Inc., New York, N.Y.) with an isocratic mobile phase of 0.01 N $H_2SO_4$ in water at a flow rate of 0.5 mL/min. Eluted compounds were quantified by refractive index detection with reference to a standard curve prepared from commercially purchased pure compounds dissolved to known concentrations in the TM3 medium.

All six fucP overexpression plasmids (Examples 4-9) resulted in improved metabolism of fructose compared to the control strain without an overexpressed fucP gene (Example 3, Comparative) in the fructose-glucose mixture (Table 2). In the case of the *E. coli* fucP gene (Examples 4, 5, and 6), the degree of improved co-metabolism of fructose and glucose corresponded to the strength of the promoter driving the expression of the gene, with the weakest promoter (1.20; U.S. Pat. No. 7,132,527) providing the poorest improvement (Example 4). Furthermore, the production of the end products 1,3-propanediol (PDO) and glycerol from the glucose-fructose mixture was also improved by expression of the fucP genes (Table 3).

TABLE 2

Glucose and Fructose Utilization

| Time (h) | Example 3, Comparative Control strain | | Example 4 + pMTP1.20fucp | | Example 5 + pMTP1.5fucP | | Example 6 + pMTP1.6fucP | | Example 7 + pMTP1.5XcfucP | | Example 8 + pMTP1.5-SefucP | | Example 9 + pMTP1.5KpfucP | |
|---|---|---|---|---|---|---|---|---|---|---|---|---|---|---|
| | Gluc (g/L) | Fruc (g/L) | Gluc (g/L) | Fruc (g/L) | Gluc (g/L) | Fruc (g/L) | Gluc (g/L) | Fruc (g/L) | Gluc (g/L) | Fruc (g/L) | Gluc (g/L) | Fruc (g/L) | Gluc (g/L) | Fruc (g/L) |
| 0 | 8.95 | 1.03 | 8.95 | 1.03 | 8.95 | 1.03 | 8.95 | 1.03 | 8.95 | 1.03 | 8.95 | 1.03 | 8.95 | 1.03 |
| 5 | 8.71 | 1.01 | 8.72 | 1.01 | 8.72 | 1.01 | 8.75 | 1.01 | 8.75 | 1.01 | 8.74 | 1.01 | 8.81 | 1.01 |
| 8 | 7.61 | 1.01 | 7.71 | 1.00 | 7.75 | 0.99 | 7.86 | 0.98 | 7.89 | 0.98 | 7.86 | 1.01 | 8.10 | 0.94 |
| 11 | 5.28 | 1.00 | 5.24 | 0.97 | 5.34 | 0.93 | 5.55 | 0.87 | 5.57 | 0.88 | 5.53 | 0.99 | 6.10 | 0.66 |
| 14 | 0.98 | 0.98 | 0.82 | 0.87 | 0.97 | 0.75 | 1.41 | 0.65 | 1.57 | 0.66 | 1.35 | 0.95 | 2.67 | 0.24 |
| 17 | 0.00 | 0.86 | 0.00 | 0.69 | 0.00 | 0.48 | 0.00 | 0.36 | 0.00 | 0.38 | 0.00 | 0.84 | 0.00 | 0.00 |
| 20 | 0.00 | 0.74 | 0.00 | 0.53 | 0.00 | 0.26 | 0.00 | 0.16 | 0.00 | 0.18 | 0.00 | 0.73 | 0.00 | 0.00 |
| 23 | 0.00 | 0.58 | 0.00 | 0.38 | 0.00 | 0.07 | 0.00 | 0.00 | 0.00 | 0.01 | 0.00 | 0.61 | 0.00 | 0.00 |

TABLE 3

PDO and Glycerol Production

| | | Mol/L PDO + Glycerol | | | | | |
|---|---|---|---|---|---|---|---|
| Time (h) | Example 3 Comparative Control strain | Example 4 + pMTP1.20fucp | Example 5 + pMTP1.5fucP | Example 6 + pMTP1.6fucP | Example 7 + pMTP1.5XcfucP | Example 8 + pMTP1.5SefucP | Example 9 + pMTP1.5KpfucP |
| 0 | 0.000 | 0.000 | 0.000 | 0.000 | 0.000 | 0.000 | 0.000 |
| 5 | 0.001 | 0.001 | 0.001 | 0.001 | 0.001 | 0.001 | 0.001 |
| 8 | 0.008 | 0.008 | 0.007 | 0.007 | 0.006 | 0.006 | 0.005 |
| 11 | 0.024 | 0.025 | 0.025 | 0.024 | 0.024 | 0.023 | 0.022 |
| 14 | 0.052 | 0.057 | 0.057 | 0.055 | 0.054 | 0.053 | 0.050 |
| 17 | 0.057 | 0.062 | 0.063 | 0.066 | 0.065 | 0.061 | 0.069 |
| 20 | 0.058 | 0.062 | 0.064 | 0.066 | 0.066 | 0.061 | 0.068 |
| 23 | 0.059 | 0.063 | 0.065 | 0.067 | 0.067 | 0.062 | 0.068 |

What is claimed is:

1. A recombinant microorganism comprising a promoter operably linked to a native or non-native nucleotide sequence, wherein the recombinant microorganism is PTS (phosphoenolpyruvate-suqar phosphotransferase) minus and has increased fructokinase activity, and wherein the native or non-native nucleotide sequence is selected from the group consisting of:

(a) a nucleotide sequence encoding a fucose: $H^+$symporter polypeptide, wherein the polypeptide has at least 95% amino acid identity, based on the Clustal V method of alignment, when compared to the amino acid sequence of SEQ ID NO:2;

(b) a nucleotide sequence encoding a fucose: $H^+$symporter polypeptide wherein the nucleotide sequence has at least 95% sequence identity, based on the BLASTN method of alignment, when compared to the nucleotide sequence of SEQ ID NO:1; and (c) a nucleotide sequence encoding a fucose: $H^+$symporter polypeptide, wherein the nucleotide sequence hybridizes under stringent conditions to the nucleotide sequence of SEQ ID NO:1 wherein stringent conditions comprise hybridization in 40 to 45% formamide, 1 M NaCl, 1% SDS (sodium dodecyl sulfate) at 37° C., and a wash in 0.5×to 1×SSC at 55 to 60 ° C.;

wherein the promoter is one that is not normally associated with the nucleotide sequence encoding a fucose: $H^+$symporter polypeptide, the nucleotide sequence is overexpressed in the recombinant microorganism, the recombinant microorganism has an improved ability to co-metabolize in medium both fructose and glucose compared to an equivalent microorganism lacking the promoter operably linked to the nucleotide sequence, and further wherein the recombinant microorganism produces an increased amount of 1,3-propanediol, glycerol, or 3-hydroxypropionic acid when grown in a medium containing glucose and fructose as compared to an equivalent microorganism lacking the promoter operably linked to the nucleotide sequence.

2. The recombinant microorganism of claim 1 wherein said microorganism is selected from the group consisting of organisms of the genera:

*Escherichia, Streptococcus, Agrobacterium, Bacillus, Corynebacterium, Lactobacillus, Clostridium, Gluconobacter, Saccharomyces, Kluyveromyces, Aspergillus, Pichia, Rhizopus, Citrobacter, Enterobacter, Klebsiella, Aerobacter, Schizosaccharomyces, Zygosaccharomyces, Candida, Hansenula, Debaryomyces, Mucor, Torulopsis, Methylobacter, Salmonella, Streptomyces*, and *Pseudomonas*.

3. The recombinant microorganism of claim 2 wherein said microorganism is selected from the group consisting of organisms of the genera:

*Escherichia, Klebsiella, Citrobacter*, and *Aerobacter*.

4. The recombinant microorganism of claim 3 wherein said microorganism is *Escherichia coli*.

5. An improved method for producing 1,3-propanediol, glycerol, or 3-hydroxypropionic acid from a microorganism, said method comprising:

(a) culturing the recombinant microorganism of any of claims 1-4 in the presence of a carbon source comprising fructose or glucose; and (b) optionally, recovering the 1,3-propanediol, glycerol, or 3-hydroxypropionic acid produce in (a).

6. A process for reducing the level of fructose in a fermentation medium comprising:

(a) culturing the recombinant microorganism of any of claims 1-4 in the presence of fructose or glucose; and (b) optionally, determining the level of fructose remaining in the fermentation medium.

7. The recombinant microorganism of claim 1 wherein the recombinant microorganism has reduced expression of one or more polynucleotides encoding one or more polypeptides selected from the group consisting of aerobic respiration control protein, methylglyoxal synthase, acetate kinase, phosphotransacetylase, aldehyde dehydrogenase A, aldehyde dehydrogenase B, and triosephosphate isomerase, and wherein the reduced expression of one or more of said polynucleotides increases 1,3-propanediol production from said recombinant microorganism when grown in a medium containing glucose and fructose.

8. The recombinant microorganism of claim 1 further comprising one or more polynucleotides encoding one or more polypeptides, wherein the one or more polypeptides have at least 95% identity, based on the Clustal V method of alignment, when compared to an amino acid sequence selected from the group consisting of SEQ ID NOs: 12, 14, 16, and 44.

* * * * *

SEQUENCE LISTING

<160> NUMBER OF SEQ ID NOS: 71

<210> SEQ ID NO 1
<211> LENGTH: 1317
<212> TYPE: DNA
<213> ORGANISM: Escherichia coli

<400> SEQUENCE: 1

```
atgggaaaca catcaataca aacgcagagt taccgtgcgg tagataaaga tgcagggcaa      60

agcagaagtt acattattcc attcgcgctg ctgtgctcac tgttttttct ttgggcggta     120

gccaataacc ttaacgacat tttattacct caattccagc aggcttttac gctgacaaat     180

ttccaggctg gcctgatcca atcggccttt tactttggtt atttcattat cccaatccct     240

gctgggatat tgatgaaaaa actcagttat aaagcaggga ttattaccgg gttattttta     300

tatgccttgg gtgctgcatt attctggccc gccgcagaaa taatgaacta caccttgttt     360

ttagttggcc tatttattat tgcagccgga ttaggttgtc tggaaactgc cgcaaaccct     420
```

-continued

```
tttgttacgg tattagggcc ggaaagtagt ggtcacttcc gcttaaatct tgcgcaaaca    480

tttaactcgt ttggcgcaat tatcgcggtt gtctttgggc aaagtcttat tttgtctaac    540

gtgccacatc aatcgcaaga cgttctcgat aaaatgtctc cagagcaatt gagtgcgtat    600

aaacacagcc tggtattatc ggtacagaca ccttatatga tcatcgtggc tatcgtgtta    660

ctggtcgccc tgctgatcat gctgacgaaa ttcccggcat tgcagagtga taatcacagt    720

gacgccaaac aaggatcgtt ctccgcatcg ctttctcgcc tggcgcgtat tcgccactgg    780

cgctgggcgg tattagcgca attctgctat gtcggcgcac aaacggcctg ctggagctat    840

ttgattcgct acgctgtaga agaaattcca ggtatgactg caggctttgc cgctaactat    900

ttaaccggaa ccatggtgtg cttctttatt ggtcgtttca ccggtacctg gctcatcagt    960

cgcttcgcac cacacaaagt cctggccgcc tacgcattaa tcgctatggc actgtgcctg   1020

atctcagcct tcgctggcgg tcatgtgggc ttaatagccc tgactttatg cagcgccttt   1080

atgtcgattc agtacccaac aatcttctcg ctgggcatta agaatctcgg ccaggacacc   1140

aaatatggtt cgtccttcat cgttatgacc attattggcg gcggtattgt cactccggtc   1200

atgggttttg tcagtgacgc ggcgggcaac atccccactg ctgaactgat ccccgcactc   1260

tgcttcgcgg tcatctttat ctttgcccgt ttccgttctc aaacggcaac taactga      1317


<210> SEQ ID NO 2
<211> LENGTH: 438
<212> TYPE: PRT
<213> ORGANISM: Escherichia coli

<400> SEQUENCE: 2

Met Gly Asn Thr Ser Ile Gln Thr Gln Ser Tyr Arg Ala Val Asp Lys
1               5                   10                  15

Asp Ala Gly Gln Ser Arg Ser Tyr Ile Ile Pro Phe Ala Leu Leu Cys
            20                  25                  30

Ser Leu Phe Phe Leu Trp Ala Val Ala Asn Asn Leu Asn Asp Ile Leu
        35                  40                  45

Leu Pro Gln Phe Gln Gln Ala Phe Thr Leu Thr Asn Phe Gln Ala Gly
    50                  55                  60

Leu Ile Gln Ser Ala Phe Tyr Phe Gly Tyr Phe Ile Ile Pro Ile Pro
65                  70                  75                  80

Ala Gly Ile Leu Met Lys Lys Leu Ser Tyr Lys Ala Gly Ile Ile Thr
                85                  90                  95

Gly Leu Phe Leu Tyr Ala Leu Gly Ala Ala Leu Phe Trp Pro Ala Ala
            100                 105                 110

Glu Ile Met Asn Tyr Thr Leu Phe Leu Val Gly Leu Phe Ile Ile Ala
        115                 120                 125

Ala Gly Leu Gly Cys Leu Glu Thr Ala Ala Asn Pro Phe Val Thr Val
    130                 135                 140

Leu Gly Pro Glu Ser Ser Gly His Phe Arg Leu Asn Leu Ala Gln Thr
145                 150                 155                 160

Phe Asn Ser Phe Gly Ala Ile Ile Ala Val Val Phe Gly Gln Ser Leu
                165                 170                 175

Ile Leu Ser Asn Val Pro His Gln Ser Gln Asp Val Leu Asp Lys Met
            180                 185                 190

Ser Pro Glu Gln Leu Ser Ala Tyr Lys His Ser Leu Val Leu Ser Val
        195                 200                 205

Gln Thr Pro Tyr Met Ile Ile Val Ala Ile Val Leu Leu Val Ala Leu
    210                 215                 220
```

-continued

```
Leu Ile Met Leu Thr Lys Phe Pro Ala Leu Gln Ser Asp Asn His Ser
225                 230                 235                 240

Asp Ala Lys Gln Gly Ser Phe Ser Ala Ser Leu Ser Arg Leu Ala Arg
                245                 250                 255

Ile Arg His Trp Arg Trp Ala Val Leu Ala Gln Phe Cys Tyr Val Gly
            260                 265                 270

Ala Gln Thr Ala Cys Trp Ser Tyr Leu Ile Arg Tyr Ala Val Glu Glu
        275                 280                 285

Ile Pro Gly Met Thr Ala Gly Phe Ala Ala Asn Tyr Leu Thr Gly Thr
    290                 295                 300

Met Val Cys Phe Phe Ile Gly Arg Phe Thr Gly Thr Trp Leu Ile Ser
305                 310                 315                 320

Arg Phe Ala Pro His Lys Val Leu Ala Ala Tyr Ala Leu Ile Ala Met
                325                 330                 335

Ala Leu Cys Leu Ile Ser Ala Phe Ala Gly Gly His Val Gly Leu Ile
            340                 345                 350

Ala Leu Thr Leu Cys Ser Ala Phe Met Ser Ile Gln Tyr Pro Thr Ile
        355                 360                 365

Phe Ser Leu Gly Ile Lys Asn Leu Gly Gln Asp Thr Lys Tyr Gly Ser
    370                 375                 380

Ser Phe Ile Val Met Thr Ile Ile Gly Gly Gly Ile Val Thr Pro Val
385                 390                 395                 400

Met Gly Phe Val Ser Asp Ala Ala Gly Asn Ile Pro Thr Ala Glu Leu
                405                 410                 415

Ile Pro Ala Leu Cys Phe Ala Val Ile Phe Ile Phe Ala Arg Phe Arg
            420                 425                 430

Ser Gln Thr Ala Thr Asn
        435
```

<210> SEQ ID NO 3
<211> LENGTH: 1176
<212> TYPE: DNA
<213> ORGANISM: Saccharomyces cerevisiae

<400> SEQUENCE: 3

```
atgtctgctg ctgctgatag attaaactta acttccggcc acttgaatgc tggtagaaag      60

agaagttcct cttctgtttc tttgaaggct gccgaaaagc ctttcaaggt tactgtgatt     120

ggatctggta actggggtac tactattgcc aaggtggttg ccgaaaattg taagggatac     180

ccagaagttt tcgctccaat agtacaaatg tgggtgttcg aagaagagat caatggtgaa     240

aaattgactg aaatcataaa tactagacat caaaacgtga aatacttgcc tggcatcact     300

ctacccgaca atttggttgc taatccagac ttgattgatt cagtcaagga tgtcgacatc     360

atcgttttca acattccaca tcaatttttg ccccgtatct gtagccaatt gaaaggtcat     420

gttgattcac acgtcagagc tatctcctgt ctaaagggtt ttgaagttgg tgctaaaggt     480

gtccaattgc tatcctctta catcactgag gaactaggta ttcaatgtgg tgctctatct     540

ggtgctaaca ttgccaccga agtcgctcaa gaacactggt ctgaaacaac agttgcttac     600

cacattccaa aggatttcag aggcgagggc aaggacgtcg accataaggt tctaaaggcc     660

ttgttccaca gaccttactt ccacgttagt gtcatcgaag atgttgctgg tatctccatc     720

tgtggtgctt tgaagaacgt tgttgcctta ggttgtggtt tcgtcgaagg tctaggctgg     780

ggtaacaacg cttctgctgc catccaaaga gtcggtttgg gtgagatcat cagattcggt     840
```

-continued

```
caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080

ccattatttg aagccgtata ccaaatcgtt tacaacaact acccaatgaa gaacctgccg   1140

gacatgattg aagaattaga tctacatgaa gattag                              1176
```

<210> SEQ ID NO 4
<211> LENGTH: 391
<212> TYPE: PRT
<213> ORGANISM: Saccharomyces cerevisiae

<400> SEQUENCE: 4

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320
```

-continued

Ser Gly Lys Asp Ala Trp Glu Cys Glu Lys Glu Leu Leu Asn Gly Gln
325 330 335

Ser Ala Gln Gly Leu Ile Thr Cys Lys Glu Val His Glu Trp Leu Glu
340 345 350

Thr Cys Gly Ser Val Glu Asp Phe Pro Leu Phe Glu Ala Val Tyr Gln
355 360 365

Ile Val Tyr Asn Asn Tyr Pro Met Lys Asn Leu Pro Asp Met Ile Glu
370 375 380

Glu Leu Asp Leu His Glu Asp
385 390

<210> SEQ ID NO 5
<211> LENGTH: 1323
<212> TYPE: DNA
<213> ORGANISM: Saccharomyces cerevisiae

<400> SEQUENCE: 5
atgcttgctg tcagaagatt aacaagatac acattcctta agcgaacgca tccggtgtta 60
tatactcgtc gtgcatataa aattttgcct tcaagatcta ctttcctaag aagatcatta 120
ttacaaacac aactgcactc aaagatgact gctcatacta atatcaaaca gcacaaacac 180
tgtcatgagg accatcctat cagaagatcg gactctgccg tgtcaattgt acatttgaaa 240
cgtgcgccct tcaaggttac agtgattggt tctggtaact gggggaccac catcgccaaa 300
gtcattgcgg aaaacacaga attgcattcc catatcttcg agccagaggt gagaatgtgg 360
gtttttgatg aaaagatcgg cgacgaaaat ctgacggata tcataaatac aagacaccag 420
aacgttaaat atctacccaa tattgacctg ccccataatc tagtggccga tcctgatctt 480
ttacactcca tcaagggtgc tgacatcctt gttttcaaca tccctcatca atttttacca 540
aacatagtca aacaattgca aggccacgtg gcccctcatg taagggccat ctcgtgtcta 600
aaagggttcg agttgggctc caagggtgtg caattgctat cctcctatgt tactgatgag 660
ttaggaatcc aatgtggcgc actatctggt gcaaacttgg caccggaagt ggccaaggag 720
cattggtccg aaaccaccgt ggcttaccaa ctaccaaagg attatcaagg tgatggcaag 780
gatgtagatc ataagatttt gaaattgctg ttccacagac cttacttcca cgtcaatgtc 840
atcgatgatg ttgctggtat atccattgcc ggtgccttga agaacgtcgt ggcacttgca 900
tgtggtttcg tagaaggtat gggatggggt aacaatgcct ccgcagccat tcaaaggctg 960
ggtttaggtg aaattatcaa gttcggtaga atgtttttcc cagaatccaa agtcgagacc 1020
tactatcaag aatccgctgg tgttgcagat ctgatcacca cctgctcagg cggtagaaac 1080
gtcaaggttg ccacatacat ggccaagacc ggtaagtcag ccttggaagc agaaaaggaa 1140
ttgcttaacg gtcaatccgc ccaagggata atcacatgca gagaagttca cgagtggcta 1200
caaacatgtg agttgaccca agaattccca ttattcgagg cagtctacca gatagtctac 1260
aacaacgtcc gcatggaaga cctaccggag atgattgaag agctagacat cgatgacgaa 1320
tag 1323

<210> SEQ ID NO 6
<211> LENGTH: 440
<212> TYPE: PRT
<213> ORGANISM: Saccharomyces cerevisiae

<400> SEQUENCE: 6

Met Leu Ala Val Arg Arg Leu Thr Arg Tyr Thr Phe Leu Lys Arg Thr

-continued

```
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys His Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

Thr Ile Ala Lys Val Ile Ala Glu Asn Thr Glu Leu His Ser His Ile
            100                 105                 110

Phe Glu Pro Glu Val Arg Met Trp Val Phe Asp Glu Lys Ile Gly Asp
        115                 120                 125

Glu Asn Leu Thr Asp Ile Ile Asn Thr Arg His Gln Asn Val Lys Tyr
    130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                165                 170                 175

Gln Phe Leu Pro Asn Ile Val Lys Gln Leu Gln Gly His Val Ala Pro
            180                 185                 190

His Val Arg Ala Ile Ser Cys Leu Lys Gly Phe Glu Leu Gly Ser Lys
        195                 200                 205

Gly Val Gln Leu Leu Ser Ser Tyr Val Thr Asp Glu Leu Gly Ile Gln
    210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                245                 250                 255

Gly Asp Gly Lys Asp Val Asp His Lys Ile Leu Lys Leu Leu Phe His
            260                 265                 270

Arg Pro Tyr Phe His Val Asn Val Ile Asp Asp Val Ala Gly Ile Ser
        275                 280                 285

Ile Ala Gly Ala Leu Lys Asn Val Val Ala Leu Ala Cys Gly Phe Val
    290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                325                 330                 335

Lys Val Glu Thr Tyr Tyr Gln Glu Ser Ala Gly Val Ala Asp Leu Ile
            340                 345                 350

Thr Thr Cys Ser Gly Gly Arg Asn Val Lys Val Ala Thr Tyr Met Ala
        355                 360                 365

Lys Thr Gly Lys Ser Ala Leu Glu Ala Glu Lys Glu Leu Leu Asn Gly
    370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Leu Phe Glu Ala Val Tyr
                405                 410                 415

Gln Ile Val Tyr Asn Asn Val Arg Met Glu Asp Leu Pro Glu Met Ile
            420                 425                 430
```

```
Glu Glu Leu Asp Ile Asp Asp Glu
        435                 440


<210> SEQ ID NO 7
<211> LENGTH: 816
<212> TYPE: DNA
<213> ORGANISM: Saccharomyces cerevisiae

<400> SEQUENCE: 7

atgaaacgtt tcaatgtttt aaaatatatc agaacaacaa aagcaaatat acaaaccatc      60

gcaatgcctt tgaccacaaa acctttatct ttgaaaatca acgccgctct attcgatgtt     120

gacggtacca tcatcatctc tcaaccagcc attgctgctt tctggagaga tttcggtaaa     180

gacaagcctt acttcgatgc cgaacacgtt attcacatct ctcacggttg gagaacttac     240

gatgccattg ccaagttcgc tccagacttt gctgatgaag aatacgttaa caagctagaa     300

ggtgaaatcc cagaaaagta cggtgaacac tccatcgaag ttccaggtgc tgtcaagttg     360

tgtaatgctt tgaacgcctt gccaaaggaa aaatgggctg tcgccacctc tggtacccgt     420

gacatggcca agaaatggtt cgacattttg aagatcaaga gaccagaata cttcatcacc     480

gccaatgatg tcaagcaagg taagcctcac ccagaaccat acttaaaggg tagaaacggt     540

ttgggtttcc caattaatga acaagaccca tccaaatcta aggttgttgt ctttgaagac     600

gcaccagctg gtattgctgc tggtaaggct gctggctgta aaatcgttgg tattgctacc     660

actttcgatt tggacttctt gaaggaaaag ggttgtgaca tcattgtcaa gaaccacgaa     720

tctatcagag tcggtgaata caacgctgaa accgatgaag tcgaattgat ctttgatgac     780

tacttatacg ctaaggatga cttgttgaaa tggtaa                               816


<210> SEQ ID NO 8
<211> LENGTH: 271
<212> TYPE: PRT
<213> ORGANISM: Saccharomyces cerevisiae

<400> SEQUENCE: 8

Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
```

-continued

```
            165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
            245                 250                 255

Ile Phe Asp Asp Tyr Leu Tyr Ala Lys Asp Asp Leu Leu Lys Trp
            260                 265                 270


<210> SEQ ID NO 9
<211> LENGTH: 753
<212> TYPE: DNA
<213> ORGANISM: Saccharomyces cerevisiae

<400> SEQUENCE: 9

atgggattga ctactaaacc tctatctttg aaagttaacg ccgctttgtt cgacgtcgac      60

ggtaccatta tcatctctca accagccatt gctgcattct ggagggattt cggtaaggac     120

aaaccttatt tcgatgctga acacgttatc caagtctcgc atggttggag aacgtttgat     180

gccattgcta agttcgctcc agactttgcc aatgaagagt atgttaacaa attagaagct     240

gaaattccgg tcaagtacgg tgaaaaatcc attgaagtcc caggtgcagt taagctgtgc     300

aacgctttga acgctctacc aaaagagaaa tgggctgtgg caacttccgg tacccgtgat     360

atggcacaaa aatggttcga gcatctggga atcaggagac caaagtactt cattaccgct     420

aatgatgtca aacagggtaa gcctcatcca gaaccatatc tgaagggcag gaatggctta     480

ggatatccga tcaatgagca agacccttcc aaatctaagg tagtagtatt tgaagacgct     540

ccagcaggta ttgccgccgg aaaagccgcc ggttgtaaga tcattggtat tgccactact     600

ttcgacttgg acttcctaaa ggaaaaaggc tgtgacatca ttgtcaaaaa ccacgaatcc     660

atcagagttg gcggctacaa tgccgaaaca gacgaagttg aattcatttt tgacgactac     720

ttatatgcta aggacgatct gttgaaatgg taa                                  753


<210> SEQ ID NO 10
<211> LENGTH: 250
<212> TYPE: PRT
<213> ORGANISM: Saccharomyces cerevisiae

<400> SEQUENCE: 10

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95
```

```
Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
                245                 250


<210> SEQ ID NO 11
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 11

atg aaa aga tca aaa cga ttt gca gta ctg gcc cag cgc ccc gtc aat       48
Met Lys Arg Ser Lys Arg Phe Ala Val Leu Ala Gln Arg Pro Val Asn
1               5                   10                  15

cag gac ggg ctg att ggc gag tgg cct gaa gag ggg ctg atc gcc atg       96
Gln Asp Gly Leu Ile Gly Glu Trp Pro Glu Glu Gly Leu Ile Ala Met
            20                  25                  30

gac agc ccc ttt gac ccg gtc tct tca gta aaa gtg gac aac ggt ctg      144
Asp Ser Pro Phe Asp Pro Val Ser Ser Val Lys Val Asp Asn Gly Leu
        35                  40                  45

atc gtc gaa ctg gac ggc aaa cgc cgg gac cag ttt gac atg atc gac      192
Ile Val Glu Leu Asp Gly Lys Arg Arg Asp Gln Phe Asp Met Ile Asp
    50                  55                  60

cga ttt atc gcc gat tac gcg atc aac gtt gag cgc aca gag cag gca      240
Arg Phe Ile Ala Asp Tyr Ala Ile Asn Val Glu Arg Thr Glu Gln Ala
65                  70                  75                  80

atg cgc ctg gag gcg gtg gaa ata gcc cgt atg ctg gtg gat att cac      288
Met Arg Leu Glu Ala Val Glu Ile Ala Arg Met Leu Val Asp Ile His
                85                  90                  95

gtc agc cgg gag gag atc att gcc atc act acc gcc atc acg ccg gcc      336
Val Ser Arg Glu Glu Ile Ile Ala Ile Thr Thr Ala Ile Thr Pro Ala
            100                 105                 110

aaa gcg gtc gag gtg atg gcg cag atg aac gtg gtg gag atg atg atg      384
Lys Ala Val Glu Val Met Ala Gln Met Asn Val Val Glu Met Met Met
        115                 120                 125

gcg ctg cag aag atg cgt gcc cgc cgg acc ccc tcc aac cag tgc cac      432
Ala Leu Gln Lys Met Arg Ala Arg Arg Thr Pro Ser Asn Gln Cys His
    130                 135                 140

gtc acc aat ctc aaa gat aat ccg gtg cag att gcc gct gac gcc gcc      480
```

-continued

```
Val Thr Asn Leu Lys Asp Asn Pro Val Gln Ile Ala Ala Asp Ala Ala
145                 150                 155                 160

gag gcc ggg atc cgc ggc ttc tca gaa cag gag acc acg gtc ggt atc      528
Glu Ala Gly Ile Arg Gly Phe Ser Glu Gln Glu Thr Thr Val Gly Ile
                165                 170                 175

gcg cgc tac gcg ccg ttt aac gcc ctg gcg ctg ttg gtc ggt tcg cag      576
Ala Arg Tyr Ala Pro Phe Asn Ala Leu Ala Leu Leu Val Gly Ser Gln
            180                 185                 190

tgc ggc cgc ccc ggc gtg ttg acg cag tgc tcg gtg gaa gag gcc acc      624
Cys Gly Arg Pro Gly Val Leu Thr Gln Cys Ser Val Glu Glu Ala Thr
        195                 200                 205

gag ctg gag ctg ggc atg cgt ggc tta acc agc tac gcc gag acg gtg      672
Glu Leu Glu Leu Gly Met Arg Gly Leu Thr Ser Tyr Ala Glu Thr Val
    210                 215                 220

tcg gtc tac ggc acc gaa gcg gta ttt acc gac ggc gat gat acg ccg      720
Ser Val Tyr Gly Thr Glu Ala Val Phe Thr Asp Gly Asp Asp Thr Pro
225                 230                 235                 240

tgg tca aag gcg ttc ctc gcc tcg gcc tac gcc tcc cgc ggg ttg aaa      768
Trp Ser Lys Ala Phe Leu Ala Ser Ala Tyr Ala Ser Arg Gly Leu Lys
                245                 250                 255

atg cgc tac acc tcc ggc acc gga tcc gaa gcg ctg atg ggc tat tcg      816
Met Arg Tyr Thr Ser Gly Thr Gly Ser Glu Ala Leu Met Gly Tyr Ser
            260                 265                 270

gag agc aag tcg atg ctc tac ctc gaa tcg cgc tgc atc ttc att act      864
Glu Ser Lys Ser Met Leu Tyr Leu Glu Ser Arg Cys Ile Phe Ile Thr
        275                 280                 285

aaa ggc gcc ggg gtt cag gga ctg caa aac ggc gcg gtg agc tgt atc      912
Lys Gly Ala Gly Val Gln Gly Leu Gln Asn Gly Ala Val Ser Cys Ile
    290                 295                 300

ggc atg acc ggc gct gtg ccg tcg ggc att cgg gcg gtg ctg gcg gaa      960
Gly Met Thr Gly Ala Val Pro Ser Gly Ile Arg Ala Val Leu Ala Glu
305                 310                 315                 320

aac ctg atc gcc tct atg ctc gac ctc gaa gtg gcg tcc gcc aac gac     1008
Asn Leu Ile Ala Ser Met Leu Asp Leu Glu Val Ala Ser Ala Asn Asp
                325                 330                 335

cag act ttc tcc cac tcg gat att cgc cgc acc gcg cgc acc ctg atg     1056
Gln Thr Phe Ser His Ser Asp Ile Arg Arg Thr Ala Arg Thr Leu Met
            340                 345                 350

cag atg ctg ccg ggc acc gac ttt att ttc tcc ggc tac agc gcg gtg     1104
Gln Met Leu Pro Gly Thr Asp Phe Ile Phe Ser Gly Tyr Ser Ala Val
        355                 360                 365

ccg aac tac gac aac atg ttc gcc ggc tcg aac ttc gat gcg gaa gat     1152
Pro Asn Tyr Asp Asn Met Phe Ala Gly Ser Asn Phe Asp Ala Glu Asp
    370                 375                 380

ttt gat gat tac aac atc ctg cag cgt gac ctg atg gtt gac ggc ggc     1200
Phe Asp Asp Tyr Asn Ile Leu Gln Arg Asp Leu Met Val Asp Gly Gly
385                 390                 395                 400

ctg cgt ccg gtg acc gag gcg gaa acc att gcc att cgc cag aaa gcg     1248
Leu Arg Pro Val Thr Glu Ala Glu Thr Ile Ala Ile Arg Gln Lys Ala
                405                 410                 415

gcg cgg gcg atc cag gcg gtt ttc cgc gag ctg ggg ctg ccg cca atc     1296
Ala Arg Ala Ile Gln Ala Val Phe Arg Glu Leu Gly Leu Pro Pro Ile
            420                 425                 430

gcc gac gag gag gtg gag gcc gcc acc tac gcg cac ggc agc aac gag     1344
Ala Asp Glu Glu Val Glu Ala Ala Thr Tyr Ala His Gly Ser Asn Glu
        435                 440                 445

atg ccg ccg cgt aac gtg gtg gag gat ctg agt gcg gtg gaa gag atg     1392
Met Pro Pro Arg Asn Val Val Glu Asp Leu Ser Ala Val Glu Glu Met
    450                 455                 460
```

```
atg aag cgc aac atc acc ggc ctc gat att gtc ggc gcg ctg agc cgc      1440
Met Lys Arg Asn Ile Thr Gly Leu Asp Ile Val Gly Ala Leu Ser Arg
465                 470                 475                 480

agc ggc ttt gag gat atc gcc agc aat att ctc aat atg ctg cgc cag      1488
Ser Gly Phe Glu Asp Ile Ala Ser Asn Ile Leu Asn Met Leu Arg Gln
                485                 490                 495

cgg gtc acc ggc gat tac ctg cag acc tcg gcc att ctc gat cgg cag      1536
Arg Val Thr Gly Asp Tyr Leu Gln Thr Ser Ala Ile Leu Asp Arg Gln
            500                 505                 510

ttc gag gtg gtg agt gcg gtc aac gac atc aat gac tat cag ggg ccg      1584
Phe Glu Val Val Ser Ala Val Asn Asp Ile Asn Asp Tyr Gln Gly Pro
        515                 520                 525

ggc acc ggc tat cgc atc tct gcc gaa cgc tgg gcg gag atc aaa aat      1632
Gly Thr Gly Tyr Arg Ile Ser Ala Glu Arg Trp Ala Glu Ile Lys Asn
    530                 535                 540

att ccg ggc gtg gtt cag ccc gac acc att gaa taa                      1668
Ile Pro Gly Val Val Gln Pro Asp Thr Ile Glu
545                 550                 555


<210> SEQ ID NO 12
<211> LENGTH: 555
<212> TYPE: PRT
<213> ORGANISM: Klebsiella pneumoniae

<400> SEQUENCE: 12

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255
```

```
Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555


<210> SEQ ID NO 13
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 13

gtg caa cag aca acc caa att cag ccc tct ttt acc ctg aaa acc cgc       48
Val Gln Gln Thr Thr Gln Ile Gln Pro Ser Phe Thr Leu Lys Thr Arg
1               5                   10                  15

gag ggc ggg gta gct tct gcc gat gaa cgc gcc gat gaa gtg gtg atc       96
Glu Gly Gly Val Ala Ser Ala Asp Glu Arg Ala Asp Glu Val Val Ile
            20                  25                  30

ggc gtc ggc cct gcc ttc gat aaa cac cag cat cac act ctg atc gat      144
Gly Val Gly Pro Ala Phe Asp Lys His Gln His His Thr Leu Ile Asp
```

-continued

```
        35                  40                  45

atg ccc cat ggc gcg atc ctc aaa gag ctg att gcc ggg gtg gaa gaa      192
Met Pro His Gly Ala Ile Leu Lys Glu Leu Ile Ala Gly Val Glu Glu
    50                  55                  60

gag ggg ctt cac gcc cgg gtg gtg cgc att ctg cgc acg tcc gac gtc      240
Glu Gly Leu His Ala Arg Val Val Arg Ile Leu Arg Thr Ser Asp Val
65                  70                  75                  80

tcc ttt atg gcc tgg gat gcg gcc aac ctg agc ggc tcg ggg atc ggc      288
Ser Phe Met Ala Trp Asp Ala Ala Asn Leu Ser Gly Ser Gly Ile Gly
                85                  90                  95

atc ggt atc cag tcg aag ggg acc acg gtc atc cat cag cgc gat ctg      336
Ile Gly Ile Gln Ser Lys Gly Thr Thr Val Ile His Gln Arg Asp Leu
            100                 105                 110

ctg ccg ctc agc aac ctg gag ctg ttc tcc cag gcg ccg ctg ctg acg      384
Leu Pro Leu Ser Asn Leu Glu Leu Phe Ser Gln Ala Pro Leu Leu Thr
        115                 120                 125

ctg gag acc tac cgg cag att ggc aaa aac gct gcg cgc tat gcg cgc      432
Leu Glu Thr Tyr Arg Gln Ile Gly Lys Asn Ala Ala Arg Tyr Ala Arg
    130                 135                 140

aaa gag tca cct tcg ccg gtg ccg gtg gtg aac gat cag atg gtg cgg      480
Lys Glu Ser Pro Ser Pro Val Pro Val Val Asn Asp Gln Met Val Arg
145                 150                 155                 160

ccg aaa ttt atg gcc aaa gcc gcg cta ttt cat atc aaa gag acc aaa      528
Pro Lys Phe Met Ala Lys Ala Ala Leu Phe His Ile Lys Glu Thr Lys
                165                 170                 175

cat gtg gtg cag gac gcc gag ccc gtc acc ctg cac atc gac tta gta      576
His Val Val Gln Asp Ala Glu Pro Val Thr Leu His Ile Asp Leu Val
            180                 185                 190

agg gag tga                                                          585
Arg Glu
```

<210> SEQ ID NO 14
<211> LENGTH: 194
<212> TYPE: PRT
<213> ORGANISM: Klebsiella pneumoniae

<400> SEQUENCE: 14

```
Val Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160
```

-continued

```
Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu


<210> SEQ ID NO 15
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

<400> SEQUENCE: 15

atg agc gag aaa acc atg cgc gtg cag gat tat ccg tta gcc acc cgc        48
Met Ser Glu Lys Thr Met Arg Val Gln Asp Tyr Pro Leu Ala Thr Arg
1               5                   10                  15

tgc ccg gag cat atc ctg acg cct acc ggc aaa cca ttg acc gat att        96
Cys Pro Glu His Ile Leu Thr Pro Thr Gly Lys Pro Leu Thr Asp Ile
            20                  25                  30

acc ctc gag aag gtg ctc tct ggc gag gtg ggc ccg cag gat gtg cgg       144
Thr Leu Glu Lys Val Leu Ser Gly Glu Val Gly Pro Gln Asp Val Arg
        35                  40                  45

atc tcc cgc cag acc ctt gag tac cag gcg cag att gcc gag cag atg       192
Ile Ser Arg Gln Thr Leu Glu Tyr Gln Ala Gln Ile Ala Glu Gln Met
    50                  55                  60

cag cgc cat gcg gtg gcg cgc aat ttc cgc cgc gcg gcg gag ctt atc       240
Gln Arg His Ala Val Ala Arg Asn Phe Arg Arg Ala Ala Glu Leu Ile
65                  70                  75                  80

gcc att cct gac gag cgc att ctg gct atc tat aac gcg ctg cgc ccg       288
Ala Ile Pro Asp Glu Arg Ile Leu Ala Ile Tyr Asn Ala Leu Arg Pro
                85                  90                  95

ttc cgc tcc tcg cag gcg gag ctg ctg gcg atc gcc gac gag ctg gag       336
Phe Arg Ser Ser Gln Ala Glu Leu Leu Ala Ile Ala Asp Glu Leu Glu
            100                 105                 110

cac acc tgg cat gcg aca gtg aat gcc gcc ttt gtc cgg gag tcg gcg       384
His Thr Trp His Ala Thr Val Asn Ala Ala Phe Val Arg Glu Ser Ala
        115                 120                 125

gaa gtg tat cag cag cgg cat aag ctg cgt aaa gga agc taa               426
Glu Val Tyr Gln Gln Arg His Lys Leu Arg Lys Gly Ser
    130                 135                 140


<210> SEQ ID NO 16
<211> LENGTH: 141
<212> TYPE: PRT
<213> ORGANISM: Klebsiella pneumoniae

<400> SEQUENCE: 16

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
```

```
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140


<210> SEQ ID NO 17
<211> LENGTH: 1539
<212> TYPE: DNA
<213> ORGANISM: Escherichia coli
<220> FEATURE:
<221> NAME/KEY: CDS
<222> LOCATION: (1)..(1539)

<400> SEQUENCE: 17

atg acc aat aat ccc cct tca gca cag att aag ccc ggc gag tat ggt       48
Met Thr Asn Asn Pro Pro Ser Ala Gln Ile Lys Pro Gly Glu Tyr Gly
1               5                   10                  15

ttc ccc ctc aag tta aaa gcc cgc tat gac aac ttt att ggc ggc gaa       96
Phe Pro Leu Lys Leu Lys Ala Arg Tyr Asp Asn Phe Ile Gly Gly Glu
            20                  25                  30

tgg gta gcc cct gcc gac ggc gag tat tac cag aat ctg acg ccg gtg      144
Trp Val Ala Pro Ala Asp Gly Glu Tyr Tyr Gln Asn Leu Thr Pro Val
        35                  40                  45

acc ggg cag ctg ctg tgc gaa gtg gcg tct tcg ggc aaa cga gac atc      192
Thr Gly Gln Leu Leu Cys Glu Val Ala Ser Ser Gly Lys Arg Asp Ile
    50                  55                  60

gat ctg gcg ctg gat gct gcg cac aaa gtg aaa gat aaa tgg gcg cac      240
Asp Leu Ala Leu Asp Ala Ala His Lys Val Lys Asp Lys Trp Ala His
65                  70                  75                  80

acc tcg gtg cag gat cgt gcg gcg att ctg ttt aag att gcc gat cga      288
Thr Ser Val Gln Asp Arg Ala Ala Ile Leu Phe Lys Ile Ala Asp Arg
                85                  90                  95

atg gaa caa aac ctc gag ctg tta gcg aca gct gaa acc tgg gat aac      336
Met Glu Gln Asn Leu Glu Leu Leu Ala Thr Ala Glu Thr Trp Asp Asn
            100                 105                 110

ggc aaa ccc att cgc gaa acc agt gct gcg gat gta ccg ctg gcg att      384
Gly Lys Pro Ile Arg Glu Thr Ser Ala Ala Asp Val Pro Leu Ala Ile
        115                 120                 125

gac cat ttc cgc tat ttc gcc tcg tgt att cgg gcg cag gaa ggt ggg      432
Asp His Phe Arg Tyr Phe Ala Ser Cys Ile Arg Ala Gln Glu Gly Gly
    130                 135                 140

atc agt gaa gtt gat agc gaa acc gtg gcc tat cat ttc cat gaa ccg      480
Ile Ser Glu Val Asp Ser Glu Thr Val Ala Tyr His Phe His Glu Pro
145                 150                 155                 160

tta ggc gtg gtg ggg cag att atc ccg tgg aac ttc ccg ctg ctg atg      528
Leu Gly Val Val Gly Gln Ile Ile Pro Trp Asn Phe Pro Leu Leu Met
                165                 170                 175

gcg agc tgg aaa atg gct ccc gcg ctg gcg gcg ggc aac tgt gtg gtg      576
Ala Ser Trp Lys Met Ala Pro Ala Leu Ala Ala Gly Asn Cys Val Val
            180                 185                 190

ctg aaa ccc gca cgt ctt acc ccg ctt tct gta ctg ctg cta atg gaa      624
Leu Lys Pro Ala Arg Leu Thr Pro Leu Ser Val Leu Leu Leu Met Glu
        195                 200                 205

att gtc ggt gat tta ctg ccg ccg ggc gtg gtg aac gtg gtc aat ggc      672
Ile Val Gly Asp Leu Leu Pro Pro Gly Val Val Asn Val Val Asn Gly
    210                 215                 220

gca ggt ggg gta att ggc gaa tat ctg gcg acc tcg aaa cgc atc gcc      720
```

```
Ala Gly Gly Val Ile Gly Glu Tyr Leu Ala Thr Ser Lys Arg Ile Ala
225                 230                 235                 240

aaa gtg gcg ttt acc ggc tca acg gaa gtg ggc caa caa att atg caa      768
Lys Val Ala Phe Thr Gly Ser Thr Glu Val Gly Gln Gln Ile Met Gln
                245                 250                 255

tac gca acg caa aac att att ccg gtg acg ctg gag ttg ggc ggt aag      816
Tyr Ala Thr Gln Asn Ile Ile Pro Val Thr Leu Glu Leu Gly Gly Lys
            260                 265                 270

tcg cca aat atc ttc ttt gct gat gtg atg gat gaa gaa gat gcc ttt      864
Ser Pro Asn Ile Phe Phe Ala Asp Val Met Asp Glu Glu Asp Ala Phe
        275                 280                 285

ttc gat aaa gcg ctg gaa ggc ttt gca ctg ttt gcc ttt aac cag ggc      912
Phe Asp Lys Ala Leu Glu Gly Phe Ala Leu Phe Ala Phe Asn Gln Gly
    290                 295                 300

gaa gtt tgc acc tgt ccg agt cgt gct tta gtg cag gaa tct atc tac      960
Glu Val Cys Thr Cys Pro Ser Arg Ala Leu Val Gln Glu Ser Ile Tyr
305                 310                 315                 320

gaa cgc ttt atg gaa cgc gcc atc cgc cgt gtc gaa agc att cgt agc     1008
Glu Arg Phe Met Glu Arg Ala Ile Arg Arg Val Glu Ser Ile Arg Ser
                325                 330                 335

ggt aac ccg ctc gac agc gtg acg caa atg ggc gcg cag gtt tct cac     1056
Gly Asn Pro Leu Asp Ser Val Thr Gln Met Gly Ala Gln Val Ser His
            340                 345                 350

ggg caa ctg gaa acc atc ctc aac tac att gat atc ggt aaa aaa gag     1104
Gly Gln Leu Glu Thr Ile Leu Asn Tyr Ile Asp Ile Gly Lys Lys Glu
        355                 360                 365

ggc gct gac gtg ctc aca ggc ggg cgg cgc aag ctg ctg gaa ggt gaa     1152
Gly Ala Asp Val Leu Thr Gly Gly Arg Arg Lys Leu Leu Glu Gly Glu
    370                 375                 380

ctg aaa gac ggc tac tac ctc gaa ccg acg att ctg ttt ggt cag aac     1200
Leu Lys Asp Gly Tyr Tyr Leu Glu Pro Thr Ile Leu Phe Gly Gln Asn
385                 390                 395                 400

aat atg cgg gtg ttc cag gag gag att ttt ggc ccg gtg ctg gcg gtg     1248
Asn Met Arg Val Phe Gln Glu Glu Ile Phe Gly Pro Val Leu Ala Val
                405                 410                 415

acc acc ttc aaa acg atg gaa gaa gcg ctg gag ctg gcg aac gat acg     1296
Thr Thr Phe Lys Thr Met Glu Glu Ala Leu Glu Leu Ala Asn Asp Thr
            420                 425                 430

caa tat ggc ctg ggc gcg ggc gtc tgg agc cgc aac ggt aat ctg gcc     1344
Gln Tyr Gly Leu Gly Ala Gly Val Trp Ser Arg Asn Gly Asn Leu Ala
        435                 440                 445

tat aag atg ggg cgc ggc ata cag gct ggg cgc gtg tgg acc aac tgt     1392
Tyr Lys Met Gly Arg Gly Ile Gln Ala Gly Arg Val Trp Thr Asn Cys
    450                 455                 460

tat cac gct tac ccg gca cat gcg gcg ttt ggt ggc tac aaa caa tca     1440
Tyr His Ala Tyr Pro Ala His Ala Ala Phe Gly Gly Tyr Lys Gln Ser
465                 470                 475                 480

ggt atc ggt cgc gaa acc cac aag atg atg ctg gag cat tac cag caa     1488
Gly Ile Gly Arg Glu Thr His Lys Met Met Leu Glu His Tyr Gln Gln
                485                 490                 495

acc aag tgc ctg ctg gtg agc tac tcg gat aaa ccg ttg ggg ctg ttc     1536
Thr Lys Cys Leu Leu Val Ser Tyr Ser Asp Lys Pro Leu Gly Leu Phe
            500                 505                 510

tga                                                                 1539
```

<210> SEQ ID NO 18
<211> LENGTH: 512
<212> TYPE: PRT
<213> ORGANISM: Escherichia coli -continued

<400> SEQUENCE: 18

```
Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
    50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
        275                 280                 285

Phe Asp Lys Ala Leu Glu Gly Phe Ala Leu Phe Ala Phe Asn Gln Gly
    290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
    370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415
```

-continued

```
Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
    450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
            500                 505                 510


<210> SEQ ID NO 19
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 19

atg tca gta ccc gtt caa cat cct atg tat atc gat gga cag ttt gtt       48
Met Ser Val Pro Val Gln His Pro Met Tyr Ile Asp Gly Gln Phe Val
1               5                   10                  15

acc tgg cgt gga gac gca tgg att gat gtg gta aac cct gct aca gag       96
Thr Trp Arg Gly Asp Ala Trp Ile Asp Val Val Asn Pro Ala Thr Glu
            20                  25                  30

gct gtc att tcc cgc ata ccc gat ggt cag gcc gag gat gcc cgt aag      144
Ala Val Ile Ser Arg Ile Pro Asp Gly Gln Ala Glu Asp Ala Arg Lys
        35                  40                  45

gca atc gat gca gca gaa cgt gca caa cca gaa tgg gaa gcg ttg cct      192
Ala Ile Asp Ala Ala Glu Arg Ala Gln Pro Glu Trp Glu Ala Leu Pro
    50                  55                  60

gct att gaa cgc gcc agt tgg ttg cgc aaa atc tcc gcc ggg atc cgc      240
Ala Ile Glu Arg Ala Ser Trp Leu Arg Lys Ile Ser Ala Gly Ile Arg
65                  70                  75                  80

gaa cgc gcc agt gaa atc agt gcg ctg att gtt gaa gaa ggg ggc aag      288
Glu Arg Ala Ser Glu Ile Ser Ala Leu Ile Val Glu Glu Gly Gly Lys
                85                  90                  95

atc cag cag ctg gct gaa gtc gaa gtg gct ttt act gcc gac tat atc      336
Ile Gln Gln Leu Ala Glu Val Glu Val Ala Phe Thr Ala Asp Tyr Ile
            100                 105                 110

gat tac atg gcg gag tgg gca cgg cgt tac gag ggc gag att att caa      384
Asp Tyr Met Ala Glu Trp Ala Arg Arg Tyr Glu Gly Glu Ile Ile Gln
        115                 120                 125

agc gat cgt cca gga gaa aat att ctt ttg ttt aaa cgt gcg ctt ggt      432
Ser Asp Arg Pro Gly Glu Asn Ile Leu Leu Phe Lys Arg Ala Leu Gly
    130                 135                 140

gtg act acc ggc att ctg ccg tgg aac ttc ccg ttc ttc ctc att gcc      480
Val Thr Thr Gly Ile Leu Pro Trp Asn Phe Pro Phe Phe Leu Ile Ala
145                 150                 155                 160

cgc aaa atg gct ccc gct ctt ttg acc ggt aat acc atc gtc att aaa      528
Arg Lys Met Ala Pro Ala Leu Leu Thr Gly Asn Thr Ile Val Ile Lys
                165                 170                 175

cct agt gaa ttt acg cca aac aat gcg att gca ttc gcc aaa atc gtc      576
Pro Ser Glu Phe Thr Pro Asn Asn Ala Ile Ala Phe Ala Lys Ile Val
            180                 185                 190

gat gaa ata ggc ctt ccg cgc ggc gtg ttt aac ctt gta ctg ggg cgt      624
```

```
Asp Glu Ile Gly Leu Pro Arg Gly Val Phe Asn Leu Val Leu Gly Arg
        195                 200                 205

ggt gaa acc gtt ggg caa gaa ctg gcg ggt aac cca aag gtc gca atg      672
Gly Glu Thr Val Gly Gln Glu Leu Ala Gly Asn Pro Lys Val Ala Met
    210                 215                 220

gtc agt atg aca ggc agc gtc tct gca ggt gag aag atc atg gcg act      720
Val Ser Met Thr Gly Ser Val Ser Ala Gly Glu Lys Ile Met Ala Thr
225                 230                 235                 240

gcg gcg aaa aac atc acc aaa gtg tgt ctg gaa ttg ggg ggt aaa gca      768
Ala Ala Lys Asn Ile Thr Lys Val Cys Leu Glu Leu Gly Gly Lys Ala
                245                 250                 255

cca gct atc gta atg gac gat gcc gat ctt gaa ctg gca gtc aaa gcc      816
Pro Ala Ile Val Met Asp Asp Ala Asp Leu Glu Leu Ala Val Lys Ala
            260                 265                 270

atc gtt gat tca cgc gtc att aat agt ggg caa gtg tgt aac tgt gca      864
Ile Val Asp Ser Arg Val Ile Asn Ser Gly Gln Val Cys Asn Cys Ala
        275                 280                 285

gaa cgt gtt tat gta cag aaa ggc att tat gat cag ttc gtc aat cgg      912
Glu Arg Val Tyr Val Gln Lys Gly Ile Tyr Asp Gln Phe Val Asn Arg
    290                 295                 300

ctg ggt gaa gcg atg cag gcg gtt caa ttt ggt aac ccc gct gaa cgc      960
Leu Gly Glu Ala Met Gln Ala Val Gln Phe Gly Asn Pro Ala Glu Arg
305                 310                 315                 320

aac gac att gcg atg ggg ccg ttg att aac gcc gcg gcg ctg gaa agg     1008
Asn Asp Ile Ala Met Gly Pro Leu Ile Asn Ala Ala Ala Leu Glu Arg
                325                 330                 335

gtc gag caa aaa gtg gcg cgc gca gta gaa gaa ggg gcg aga gtg gcg     1056
Val Glu Gln Lys Val Ala Arg Ala Val Glu Glu Gly Ala Arg Val Ala
            340                 345                 350

ttc ggt ggc aaa gcg gta gag ggg aaa gga tat tat tat ccg ccg aca     1104
Phe Gly Gly Lys Ala Val Glu Gly Lys Gly Tyr Tyr Tyr Pro Pro Thr
        355                 360                 365

ttg ctg ctg gat gtt cgc cag gaa atg tcg att atg cat gag gaa acc     1152
Leu Leu Leu Asp Val Arg Gln Glu Met Ser Ile Met His Glu Glu Thr
    370                 375                 380

ttt ggc ccg gtg ctg cca gtt gtc gca ttt gac acg ctg gaa gat gct     1200
Phe Gly Pro Val Leu Pro Val Val Ala Phe Asp Thr Leu Glu Asp Ala
385                 390                 395                 400

atc tca atg gct aat gac agt gat tac ggc ctg acc tca tca atc tat     1248
Ile Ser Met Ala Asn Asp Ser Asp Tyr Gly Leu Thr Ser Ser Ile Tyr
                405                 410                 415

acc caa aat ctg aac gtc gcg atg aaa gcc att aaa ggg ctg aag ttt     1296
Thr Gln Asn Leu Asn Val Ala Met Lys Ala Ile Lys Gly Leu Lys Phe
            420                 425                 430

ggt gaa act tac atc aac cgt gaa aac ttc gaa gct atg caa ggc ttc     1344
Gly Glu Thr Tyr Ile Asn Arg Glu Asn Phe Glu Ala Met Gln Gly Phe
        435                 440                 445

cac gcc gga tgg cgt aaa tcc ggt att ggc ggc gca gat ggt aaa cat     1392
His Ala Gly Trp Arg Lys Ser Gly Ile Gly Gly Ala Asp Gly Lys His
    450                 455                 460

ggc ttg cat gaa tat ctg cag acc cag gtg gtt tat tta cag tct taa     1440
Gly Leu His Glu Tyr Leu Gln Thr Gln Val Val Tyr Leu Gln Ser
465                 470                 475


<210> SEQ ID NO 20
<211> LENGTH: 479
<212> TYPE: PRT
<213> ORGANISM: Escherichia coli

<400> SEQUENCE: 20
```

-continued

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
        355                 360                 365

Leu Leu Leu Asp Val Arg Gln Glu Met Ser Ile Met His Glu Glu Thr
    370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
```

```
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475


<210> SEQ ID NO 21
<211> LENGTH: 1488
<212> TYPE: DNA
<213> ORGANISM: Escherichia coli
<220> FEATURE:
<221> NAME/KEY: CDS
<222> LOCATION: (1)..(1488)

<400> SEQUENCE: 21

atg aat ttt cat cat ctg gct tac tgg cag gat aaa gcg tta agt ctc       48
Met Asn Phe His His Leu Ala Tyr Trp Gln Asp Lys Ala Leu Ser Leu
1               5                   10                  15

gcc att gaa aac cgc tta ttt att aac ggt gaa tat act gct gcg gcg       96
Ala Ile Glu Asn Arg Leu Phe Ile Asn Gly Glu Tyr Thr Ala Ala Ala
            20                  25                  30

gaa aat gaa acc ttt gaa acc gtt gat ccg gtc acc cag gca ccg ctg      144
Glu Asn Glu Thr Phe Glu Thr Val Asp Pro Val Thr Gln Ala Pro Leu
        35                  40                  45

gcg aaa att gcc cgc ggc aag agc gtc gat atc gac cgt gcg atg agc      192
Ala Lys Ile Ala Arg Gly Lys Ser Val Asp Ile Asp Arg Ala Met Ser
    50                  55                  60

gca gca cgc ggc gta ttt gaa cgc ggc gac tgg tca ctc tct tct ccg      240
Ala Ala Arg Gly Val Phe Glu Arg Gly Asp Trp Ser Leu Ser Ser Pro
65                  70                  75                  80

gct aaa cgt aaa gcg gta ctg aat aaa ctc gcc gat tta atg gaa gcc      288
Ala Lys Arg Lys Ala Val Leu Asn Lys Leu Ala Asp Leu Met Glu Ala
                85                  90                  95

cac gcc gaa gag ctg gca ctg ctg gaa act ctc gac acc ggc aaa ccg      336
His Ala Glu Glu Leu Ala Leu Leu Glu Thr Leu Asp Thr Gly Lys Pro
            100                 105                 110

att cgt cac agt ctg cgt gat gat att ccc ggc gcg gcg cgc gcc att      384
Ile Arg His Ser Leu Arg Asp Asp Ile Pro Gly Ala Ala Arg Ala Ile
        115                 120                 125

cgc tgg tac gcc gaa gcg atc gac aaa gtg tat ggc gaa gtg gcg acc      432
Arg Trp Tyr Ala Glu Ala Ile Asp Lys Val Tyr Gly Glu Val Ala Thr
    130                 135                 140

acc agt agc cat gag ctg gcg atg atc gtg cgt gaa ccg gtc ggc gtg      480
Thr Ser Ser His Glu Leu Ala Met Ile Val Arg Glu Pro Val Gly Val
145                 150                 155                 160

att gcc gcc atc gtg ccg tgg aac ttc ccg ctg ttg ctg act tgc tgg      528
Ile Ala Ala Ile Val Pro Trp Asn Phe Pro Leu Leu Leu Thr Cys Trp
                165                 170                 175

aaa ctc ggc ccg gcg ctg gcg gcg gga aac agc gtg att cta aaa ccg      576
Lys Leu Gly Pro Ala Leu Ala Ala Gly Asn Ser Val Ile Leu Lys Pro
            180                 185                 190

tct gaa aaa tca ccg ctc agt gcg att cgt ctc gcg ggg ctg gcg aaa      624
Ser Glu Lys Ser Pro Leu Ser Ala Ile Arg Leu Ala Gly Leu Ala Lys
        195                 200                 205

gaa gca ggc ttg ccg gat ggt gtg ttg aac gtg gtg acg ggt ttt ggt      672
Glu Ala Gly Leu Pro Asp Gly Val Leu Asn Val Val Thr Gly Phe Gly
    210                 215                 220

cat gaa gcc ggg cag gcg ctg tcg cgt cat aac gat atc gac gcc att      720
```

-continued

```
His Glu Ala Gly Gln Ala Leu Ser Arg His Asn Asp Ile Asp Ala Ile
225                 230                 235                 240

gcc ttt acc ggt tca acc cgt acc ggg aaa cag ctg ctg aaa gat gcg      768
Ala Phe Thr Gly Ser Thr Arg Thr Gly Lys Gln Leu Leu Lys Asp Ala
                245                 250                 255

ggc gac agc aac atg aaa cgc gtc tgg ctg gaa gcg ggc ggc aaa agc      816
Gly Asp Ser Asn Met Lys Arg Val Trp Leu Glu Ala Gly Gly Lys Ser
            260                 265                 270

gcc aac atc gtt ttc gct gac tgc ccg gat ttg caa cag gcg gca agc      864
Ala Asn Ile Val Phe Ala Asp Cys Pro Asp Leu Gln Gln Ala Ala Ser
        275                 280                 285

gcc acc gca gca ggc att ttc tac aac cag gga cag gtg tgc atc gcc      912
Ala Thr Ala Ala Gly Ile Phe Tyr Asn Gln Gly Gln Val Cys Ile Ala
    290                 295                 300

gga acg cgc ctg ttg ctg gaa gag agc atc gcc gat gaa ttc tta gcc      960
Gly Thr Arg Leu Leu Leu Glu Glu Ser Ile Ala Asp Glu Phe Leu Ala
305                 310                 315                 320

ctg tta aaa cag cag gcg caa aac tgg cag ccg ggc cat cca ctt gat     1008
Leu Leu Lys Gln Gln Ala Gln Asn Trp Gln Pro Gly His Pro Leu Asp
                325                 330                 335

ccc gca acc acc atg ggc acc tta atc gac tgc gcc cac gcc gac tcg     1056
Pro Ala Thr Thr Met Gly Thr Leu Ile Asp Cys Ala His Ala Asp Ser
            340                 345                 350

gtc cat agc ttt att cgg gaa ggc gaa agc aaa ggg caa ctg ttg ttg     1104
Val His Ser Phe Ile Arg Glu Gly Glu Ser Lys Gly Gln Leu Leu Leu
        355                 360                 365

gat ggc cgt aac gcc ggg ctg gct gcc gcc atc ggc ccg acc atc ttt     1152
Asp Gly Arg Asn Ala Gly Leu Ala Ala Ala Ile Gly Pro Thr Ile Phe
    370                 375                 380

gtg gat gtg gac ccg aat gcg tcc tta agt cgc gaa gag att ttc ggt     1200
Val Asp Val Asp Pro Asn Ala Ser Leu Ser Arg Glu Glu Ile Phe Gly
385                 390                 395                 400

ccg gtg ctg gtg gtc acg cgt ttc aca tca gaa gaa cag gcg cta cag     1248
Pro Val Leu Val Val Thr Arg Phe Thr Ser Glu Glu Gln Ala Leu Gln
                405                 410                 415

ctt gcc aac gac agc cag tac ggc ctt ggc gcg gcg gta tgg acg cgc     1296
Leu Ala Asn Asp Ser Gln Tyr Gly Leu Gly Ala Ala Val Trp Thr Arg
            420                 425                 430

gac ctc tcc cgc gcg cac cgc atg agc cga cgc ctg aaa gcc ggt tcc     1344
Asp Leu Ser Arg Ala His Arg Met Ser Arg Arg Leu Lys Ala Gly Ser
        435                 440                 445

gtc ttc gtc aat aac tac aac gac ggc gat atg acc gtg ccg ttt ggc     1392
Val Phe Val Asn Asn Tyr Asn Asp Gly Asp Met Thr Val Pro Phe Gly
    450                 455                 460

ggc tat aag cag agc ggc aac ggt cgc gac aaa tcc ctg cat gcc ctt     1440
Gly Tyr Lys Gln Ser Gly Asn Gly Arg Asp Lys Ser Leu His Ala Leu
465                 470                 475                 480

gaa aaa ttc act gaa ctg aaa acc atc tgg ata agc ctg gag gcc tga     1488
Glu Lys Phe Thr Glu Leu Lys Thr Ile Trp Ile Ser Leu Glu Ala
                485                 490                 495


<210> SEQ ID NO 22
<211> LENGTH: 495
<212> TYPE: PRT
<213> ORGANISM: Escherichia coli

<400> SEQUENCE: 22

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
```

```
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
        115                 120                 125

Arg Trp Tyr Ala Glu Ala Ile Asp Lys Val Tyr Gly Glu Val Ala Thr
    130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Val Thr Gly Phe Gly
    210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
    290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
    370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445
```

Val Phe Val Asn Asn Tyr Asn Asp Gly Asp Met Thr Val Pro Phe Gly
    450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 23
<211> LENGTH: 1395
<212> TYPE: DNA
<213> ORGANISM: Escherichia coli

<400> SEQUENCE: 23
atgcctgacg ctaaaaaaca ggggcggtca aacaaggcaa tgacgttttt cgtctgcttc 60
cttgccgctc tggcgggatt actctttggc ctggatatcg gtgtaattgc tggcgcactg 120
ccgtttattg cagatgaatt ccagattact tcgcacacgc aagaatgggt cgtaagctcc 180
atgatgttcg gtgcggcagt cggtgcggtg ggcagcggct ggctctcctt taaactcggg 240
cgcaaaaaga gcctgatgat cggcgcaatt ttgtttgttg ccggttcgct gttctctgcg 300
gctgcgccaa acgttgaagt actgattctt tcccgcgttc tactggggct ggcggtgggt 360
gtggcctctt ataccgcacc gctgtacctc tctgaaattg cgccggaaaa aattcgtggc 420
agtatgatct cgatgtatca gttgatgatc actatcggga tcctcggtgc ttatctttct 480
gataccgcct tcagctacac cggtgcatgg cgctggatgc tgggtgtgat tatcatcccg 540
gcaattttgc tgctgattgg tgtcttcttc ctgccagaca gcccacgttg gtttgccgcc 600
aaacgccgtt ttgttgatgc cgaacgcgtg ctgctacgcc tgcgtgacac cagcgcggaa 660
gcgaaacgcg aactggatga aatccgtgaa agtttgcagg ttaaacagag tggctgggcg 720
ctgtttaaag agaacagcaa cttccgccgc gcggtgttcc ttggcgtact gttgcaggta 780
atgcagcaat tcaccgggat gaacgtcatc atgtattacg cgccgaaaat cttcgaactg 840
gcgggttata ccaacactac cgagcaaatg tgggggaccg tgattgtcgg cctgaccaac 900
gtacttgcca cctttatcgc aatcggcctt gttgaccgct ggggacgtaa accaacgcta 960
acgctgggct tcctggtgat ggctgctggc atgggcgtac tcggtacaat gatgcatatc 1020
ggtattcact ctccgtcggc gcagtatttc gccatcgcca tgctgctgat gtttattgtc 1080
ggttttgcca tgagtgccgg tccgctgatt tgggtactgt gctccgaaat tcagccgctg 1140
aaaggccgcg attttggcat cacctgctcc actgccacca actggattgc caacatgatc 1200
gttggcgcaa cgttcctgac catgctcaac acgctgggta acgccaacac cttctgggtg 1260
tatgcggctc tgaacgtact gtttatcctg ctgacattgt ggctggtacc ggaaaccaaa 1320
cacgtttcgc tggaacatat tgaacgtaat ctgatgaaag gtcgtaaact gcgcgaaata 1380
ggcgctcacg attaa 1395

<210> SEQ ID NO 24
<211> LENGTH: 464
<212> TYPE: PRT
<213> ORGANISM: Escherichia coli

<400> SEQUENCE: 24

Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

-continued

```
Ile Gly Val Ile Ala Gly Ala Leu Pro Phe Ile Ala Asp Glu Phe Gln
        35                  40                  45

Ile Thr Ser His Thr Gln Glu Trp Val Val Ser Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
    130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Leu Ile Gly Val Phe Phe Leu Pro
            180                 185                 190

Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
    210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
    290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
        355                 360                 365

Leu Ile Trp Val Leu Cys Ser Glu Ile Gln Pro Leu Lys Gly Arg Asp
    370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445
```

```
Arg Asn Leu Met Lys Gly Arg Lys Leu Arg Glu Ile Gly Ala His Asp
    450                 455                 460


<210> SEQ ID NO 25
<211> LENGTH: 1335
<212> TYPE: DNA
<213> ORGANISM: Klebsiella pneumoniae
<220> FEATURE:
<221> NAME/KEY: CDS
<222> LOCATION: (1)..(1335)

<400> SEQUENCE: 25

atg agt acg cta atc acg gat aag gtc gat aac gca gcg gtc caa aaa       48
Met Ser Thr Leu Ile Thr Asp Lys Val Asp Asn Ala Ala Val Gln Lys
1               5                   10                  15

gaa aaa ctg gac acc agt gcg tat tta ccc cat acc ccc tgg ctg caa       96
Glu Lys Leu Asp Thr Ser Ala Tyr Leu Pro His Thr Pro Trp Leu Gln
            20                  25                  30

ttt tta ctg gtc tgt tgc ctg ttt gcg cta tgg ggg atg gcg ggc aac      144
Phe Leu Leu Val Cys Cys Leu Phe Ala Leu Trp Gly Met Ala Gly Asn
        35                  40                  45

ctg aat gat att ttg atc gcc cag ttt aaa aag ggc ttc gat tta acg      192
Leu Asn Asp Ile Leu Ile Ala Gln Phe Lys Lys Gly Phe Asp Leu Thr
    50                  55                  60

gat acc cag aca gcg ctg gtg cag tcg att ttt ttc ctc ggc tac ttt      240
Asp Thr Gln Thr Ala Leu Val Gln Ser Ile Phe Phe Leu Gly Tyr Phe
65                  70                  75                  80

ttt gtc gcc ctg ccc gcg gcg gcg ctg att aag cgt ttc tcc tat aaa      288
Phe Val Ala Leu Pro Ala Ala Ala Leu Ile Lys Arg Phe Ser Tyr Lys
                85                  90                  95

gcg gcg att att att ggg ctg tgc ctg tac gcc ctc ggc tgc ttc ctg      336
Ala Ala Ile Ile Ile Gly Leu Cys Leu Tyr Ala Leu Gly Cys Phe Leu
            100                 105                 110

ttc gtt ccg gcc gca cag atc atg acc tac ggc gca ttc ctc gcc tgc      384
Phe Val Pro Ala Ala Gln Ile Met Thr Tyr Gly Ala Phe Leu Ala Cys
        115                 120                 125

ctc gga gtg atc gcc tgc gga ctc tct ttt ctg gaa acg tcg gca aac      432
Leu Gly Val Ile Ala Cys Gly Leu Ser Phe Leu Glu Thr Ser Ala Asn
    130                 135                 140

acc tac tcc agc ctg ctg ggt ccg att caa tcc tcc acc cag cgt att      480
Thr Tyr Ser Ser Leu Leu Gly Pro Ile Gln Ser Ser Thr Gln Arg Ile
145                 150                 155                 160

aac ttt tcg cag atc ttc aac tcg ctg ggc gtg atc tcc ggc gta tta      528
Asn Phe Ser Gln Ile Phe Asn Ser Leu Gly Val Ile Ser Gly Val Leu
                165                 170                 175

att ggc cag ctg atg gtc ttt ggc gaa aac gat ccg agt cat gaa caa      576
Ile Gly Gln Leu Met Val Phe Gly Glu Asn Asp Pro Ser His Glu Gln
            180                 185                 190

ctg ctg gcg atg ccc gcc gcc gct gca gac gtt gca cgc cat cag atg      624
Leu Leu Ala Met Pro Ala Ala Ala Ala Asp Val Ala Arg His Gln Met
        195                 200                 205

gtt ggt cag gtg gtc ggg ccc tat ctg att atc ggc tcc gta ctg gtg      672
Val Gly Gln Val Val Gly Pro Tyr Leu Ile Ile Gly Ser Val Leu Val
    210                 215                 220

gtg ctg gcg ctg gtg ttc gtg ttt att aaa ttc ccg tcg tgc aag ggc      720
Val Leu Ala Leu Val Phe Val Phe Ile Lys Phe Pro Ser Cys Lys Gly
225                 230                 235                 240

gcg ccc gct caa cag caa caa ctc ccg acg gaa agc atg ggg cca acg      768
Ala Pro Ala Gln Gln Gln Gln Leu Pro Thr Glu Ser Met Gly Pro Thr
                245                 250                 255

ctg aaa cgc ctg ttt gct atc ccg cgc ttt cgc ctc ggg atc ctg tcg      816
```

```
Leu Lys Arg Leu Phe Ala Ile Pro Arg Phe Arg Leu Gly Ile Leu Ser
            260                 265                 270

cag ttt ttg tac gtc ggc gcc cag gtt ggc gta tgg agc ttc acg att      864
Gln Phe Leu Tyr Val Gly Ala Gln Val Gly Val Trp Ser Phe Thr Ile
        275                 280                 285

cgc ttt gtg cag ctc gtg cag caa ggc acc agc gag cac tcc gcg act      912
Arg Phe Val Gln Leu Val Gln Gln Gly Thr Ser Glu His Ser Ala Thr
    290                 295                 300

tac tgg ctg ctg gct tct ctg gtg att tac gcc gtg gga aaa acc gtg      960
Tyr Trp Leu Leu Ala Ser Leu Val Ile Tyr Ala Val Gly Lys Thr Val
305                 310                 315                 320

gcc acc tgg ttg atg aac cgt ctg aat ccg gcg atg ctg ctc gga acg     1008
Ala Thr Trp Leu Met Asn Arg Leu Asn Pro Ala Met Leu Leu Gly Thr
                325                 330                 335

ttt gcc ctg gcc gcc acc gcc ctg tta ctg att gcc gtt ttc agc ggt     1056
Phe Ala Leu Ala Ala Thr Ala Leu Leu Leu Ile Ala Val Phe Ser Gly
            340                 345                 350

tca atg ctg gcg gtc tat gcg ctc att ctg gtc agc ttc tgt atg gcg     1104
Ser Met Leu Ala Val Tyr Ala Leu Ile Leu Val Ser Phe Cys Met Ala
        355                 360                 365

cca tgc tgg ccg acg aac ttt ggt ctg gtg atc aaa ggg atg ggg aaa     1152
Pro Cys Trp Pro Thr Asn Phe Gly Leu Val Ile Lys Gly Met Gly Lys
    370                 375                 380

gat acc cag acc gca ggc tcg atc gtg gtg atg tcg att atc ggc ggg     1200
Asp Thr Gln Thr Ala Gly Ser Ile Val Val Met Ser Ile Ile Gly Gly
385                 390                 395                 400

gcc gta att ccg ctg gtg atg ggc att atc tcg gat atg aac ggc ggc     1248
Ala Val Ile Pro Leu Val Met Gly Ile Ile Ser Asp Met Asn Gly Gly
                405                 410                 415

aat atg caa atc gcc ttt atc gct ccg ctc ctg tgc ttt gtg tat gtc     1296
Asn Met Gln Ile Ala Phe Ile Ala Pro Leu Leu Cys Phe Val Tyr Val
            420                 425                 430

gct ttc tac ggc ttc tgg tgc gtg cgt aag ggg gta taa                 1335
Ala Phe Tyr Gly Phe Trp Cys Val Arg Lys Gly Val
        435                 440


<210> SEQ ID NO 26
<211> LENGTH: 444
<212> TYPE: PRT
<213> ORGANISM: Klebsiella pneumoniae

<400> SEQUENCE: 26

Met Ser Thr Leu Ile Thr Asp Lys Val Asp Asn Ala Ala Val Gln Lys
1               5                   10                  15

Glu Lys Leu Asp Thr Ser Ala Tyr Leu Pro His Thr Pro Trp Leu Gln
            20                  25                  30

Phe Leu Leu Val Cys Cys Leu Phe Ala Leu Trp Gly Met Ala Gly Asn
        35                  40                  45

Leu Asn Asp Ile Leu Ile Ala Gln Phe Lys Lys Gly Phe Asp Leu Thr
    50                  55                  60

Asp Thr Gln Thr Ala Leu Val Gln Ser Ile Phe Phe Leu Gly Tyr Phe
65                  70                  75                  80

Phe Val Ala Leu Pro Ala Ala Ala Leu Ile Lys Arg Phe Ser Tyr Lys
                85                  90                  95

Ala Ala Ile Ile Ile Gly Leu Cys Leu Tyr Ala Leu Gly Cys Phe Leu
            100                 105                 110

Phe Val Pro Ala Ala Gln Ile Met Thr Tyr Gly Ala Phe Leu Ala Cys
        115                 120                 125
```

```
Leu Gly Val Ile Ala Cys Gly Leu Ser Phe Leu Glu Thr Ser Ala Asn
    130                 135                 140

Thr Tyr Ser Ser Leu Leu Gly Pro Ile Gln Ser Ser Thr Gln Arg Ile
145                 150                 155                 160

Asn Phe Ser Gln Ile Phe Asn Ser Leu Gly Val Ile Ser Gly Val Leu
                165                 170                 175

Ile Gly Gln Leu Met Val Phe Gly Glu Asn Asp Pro Ser His Glu Gln
            180                 185                 190

Leu Leu Ala Met Pro Ala Ala Ala Ala Asp Val Ala Arg His Gln Met
        195                 200                 205

Val Gly Gln Val Val Gly Pro Tyr Leu Ile Ile Gly Ser Val Leu Val
    210                 215                 220

Val Leu Ala Leu Val Phe Val Phe Ile Lys Phe Pro Ser Cys Lys Gly
225                 230                 235                 240

Ala Pro Ala Gln Gln Gln Gln Leu Pro Thr Glu Ser Met Gly Pro Thr
                245                 250                 255

Leu Lys Arg Leu Phe Ala Ile Pro Arg Phe Arg Leu Gly Ile Leu Ser
            260                 265                 270

Gln Phe Leu Tyr Val Gly Ala Gln Val Gly Val Trp Ser Phe Thr Ile
        275                 280                 285

Arg Phe Val Gln Leu Val Gln Gln Gly Thr Ser Glu His Ser Ala Thr
    290                 295                 300

Tyr Trp Leu Leu Ala Ser Leu Val Ile Tyr Ala Val Gly Lys Thr Val
305                 310                 315                 320

Ala Thr Trp Leu Met Asn Arg Leu Asn Pro Ala Met Leu Leu Gly Thr
                325                 330                 335

Phe Ala Leu Ala Ala Thr Ala Leu Leu Leu Ile Ala Val Phe Ser Gly
            340                 345                 350

Ser Met Leu Ala Val Tyr Ala Leu Ile Leu Val Ser Phe Cys Met Ala
        355                 360                 365

Pro Cys Trp Pro Thr Asn Phe Gly Leu Val Ile Lys Gly Met Gly Lys
    370                 375                 380

Asp Thr Gln Thr Ala Gly Ser Ile Val Val Met Ser Ile Ile Gly Gly
385                 390                 395                 400

Ala Val Ile Pro Leu Val Met Gly Ile Ile Ser Asp Met Asn Gly Gly
                405                 410                 415

Asn Met Gln Ile Ala Phe Ile Ala Pro Leu Leu Cys Phe Val Tyr Val
            420                 425                 430

Ala Phe Tyr Gly Phe Trp Cys Val Arg Lys Gly Val
        435                 440
```

<210> SEQ ID NO 27
<211> LENGTH: 1299
<212> TYPE: DNA
<213> ORGANISM: Xanthomonas campestris
<220> FEATURE:
<221> NAME/KEY: CDS
<222> LOCATION: (1)..(1299)

<400> SEQUENCE: 27

```
atg cat tac agc gat acc gcc gcg tca ccg cgc ggc aac ctg gcg cgt       48
Met His Tyr Ser Asp Thr Ala Ala Ser Pro Arg Gly Asn Leu Ala Arg
1               5                   10                  15

acc gcc gtg gtg ccc ctg ttg ttg atc gtc agc ctg ttt ttt cta tgg       96
Thr Ala Val Val Pro Leu Leu Leu Ile Val Ser Leu Phe Phe Leu Trp
            20                  25                  30
```

-continued

```
ggc atg gcg aac aac ctc aac gac atc ctg atc aag cag ttc aag aag      144
Gly Met Ala Asn Asn Leu Asn Asp Ile Leu Ile Lys Gln Phe Lys Lys
        35                  40                  45

gcc ttc gag ctg tcc gac ctg cag gcc ggg ctg gtg cag agc gct ttc      192
Ala Phe Glu Leu Ser Asp Leu Gln Ala Gly Leu Val Gln Ser Ala Phe
    50                  55                  60

tac ctg ggc tat ttc gtg ttc gcg atg cca gcg gcg atg ttc atg cgc      240
Tyr Leu Gly Tyr Phe Val Phe Ala Met Pro Ala Ala Met Phe Met Arg
65                  70                  75                  80

cgc tac agc tac aag gcc gcg gtg gtg ctg ggc ctg ctg cta tat gcc      288
Arg Tyr Ser Tyr Lys Ala Ala Val Val Leu Gly Leu Leu Leu Tyr Ala
                85                  90                  95

tgc ggc gcg ttc ctg ttc tat ccg gcc gcg cag gtg cac acc tac tgg      336
Cys Gly Ala Phe Leu Phe Tyr Pro Ala Ala Gln Val His Thr Tyr Trp
            100                 105                 110

ctg ttc ctg ctg gcg ttg ttc gtg atc gcc agc ggc ctg gcg ttt ctg      384
Leu Phe Leu Leu Ala Leu Phe Val Ile Ala Ser Gly Leu Ala Phe Leu
        115                 120                 125

gaa acc acc gcc aat ccg ctg gtc acc gtg ctg ggc ccg gcc gac ggc      432
Glu Thr Thr Ala Asn Pro Leu Val Thr Val Leu Gly Pro Ala Asp Gly
    130                 135                 140

gcg gcg cgg cgg ctc aat ctt gcg cag gcc ttc aat ccg ctg ggc tcg      480
Ala Ala Arg Arg Leu Asn Leu Ala Gln Ala Phe Asn Pro Leu Gly Ser
145                 150                 155                 160

atc acc ggc gtg ctg gtg ggc cag cat ttc att ttc tcc ggc gtg gag      528
Ile Thr Gly Val Leu Val Gly Gln His Phe Ile Phe Ser Gly Val Glu
                165                 170                 175

cac acc cca gcc gag ctg gcg gcg atg gcg ccg gcc gcg cgc gag gcc      576
His Thr Pro Ala Glu Leu Ala Ala Met Ala Pro Ala Ala Arg Glu Ala
            180                 185                 190

ttc ttc gcc acc gaa tcc tca gcg gtg cag atg ccc tat ctg atc atc      624
Phe Phe Ala Thr Glu Ser Ser Ala Val Gln Met Pro Tyr Leu Ile Ile
        195                 200                 205

ggc gtg gtg gtg gtg ctg tgg gcg atc ctg atc gcg ctg gtg cgc ttc      672
Gly Val Val Val Val Leu Trp Ala Ile Leu Ile Ala Leu Val Arg Phe
    210                 215                 220

cca acc ggc gac gcc ggc gtg ggc acg gcg gcc ccc aag cgt gcc aag      720
Pro Thr Gly Asp Ala Gly Val Gly Thr Ala Ala Pro Lys Arg Ala Lys
225                 230                 235                 240

ttc ggc gaa ttg ctg cgt aac cgg ctg ttc gtg ttt tcg gtg gtg gcg      768
Phe Gly Glu Leu Leu Arg Asn Arg Leu Phe Val Phe Ser Val Val Ala
                245                 250                 255

cag ttc ttc tac gtg ggc gcg cag gtc ggc atc tgg agt tat ttg att      816
Gln Phe Phe Tyr Val Gly Ala Gln Val Gly Ile Trp Ser Tyr Leu Ile
            260                 265                 270

cgc tac ctg cag gat gcg gtc ccc ggt acg ccg gaa aaa agc gcg gcc      864
Arg Tyr Leu Gln Asp Ala Val Pro Gly Thr Pro Glu Lys Ser Ala Ala
        275                 280                 285

acc tat ctg acg atc tcg ctg gtg cta ttc atg gcc ggg cgc ttt gtc      912
Thr Tyr Leu Thr Ile Ser Leu Val Leu Phe Met Ala Gly Arg Phe Val
    290                 295                 300

ggc acc gca ctg ctg cgc tat ctg gcg ccg gcc aag ttg ctg gcc agc      960
Gly Thr Ala Leu Leu Arg Tyr Leu Ala Pro Ala Lys Leu Leu Ala Ser
305                 310                 315                 320

ttt gcc acg atc aat ctg ctg ctg tgc gca gtc gcg att gcc ttg ccg     1008
Phe Ala Thr Ile Asn Leu Leu Leu Cys Ala Val Ala Ile Ala Leu Pro
                325                 330                 335

ggc tgg act ggc ctg tat gcg ctg gtt gcg gcc agc gtg ttc atg tcg     1056
Gly Trp Thr Gly Leu Tyr Ala Leu Val Ala Ala Ser Val Phe Met Ser
            340                 345                 350
```

```
gta atg ttc ccg acc atc ttc gcg ctg ggc ctg gat ggc atg cac gat     1104
Val Met Phe Pro Thr Ile Phe Ala Leu Gly Leu Asp Gly Met His Asp
        355                 360                 365

gac gca cgc aag ctg ggg tct tcg ttg ctg gtg atg gcc atc att ggt     1152
Asp Ala Arg Lys Leu Gly Ser Ser Leu Leu Val Met Ala Ile Ile Gly
    370                 375                 380

ggc gcc ttg ctc act gcg ctc atg ggt gcg gtg tcg gac atg gcc ggc     1200
Gly Ala Leu Leu Thr Ala Leu Met Gly Ala Val Ser Asp Met Ala Gly
385                 390                 395                 400

atc cat tgg gca atg gtg gtg ccc ggt gtg tgc ttc ggc gtg atc ctg     1248
Ile His Trp Ala Met Val Val Pro Gly Val Cys Phe Gly Val Ile Leu
                405                 410                 415

ctg ttc gcg ttg cgt gcc cgt cgt gct gcg cct gtg gtg gcg ggg gca     1296
Leu Phe Ala Leu Arg Ala Arg Arg Ala Ala Pro Val Val Ala Gly Ala
            420                 425                 430

tga                                                                 1299


<210> SEQ ID NO 28
<211> LENGTH: 432
<212> TYPE: PRT
<213> ORGANISM: Xanthomonas campestris

<400> SEQUENCE: 28

Met His Tyr Ser Asp Thr Ala Ala Ser Pro Arg Gly Asn Leu Ala Arg
1               5                   10                  15

Thr Ala Val Val Pro Leu Leu Leu Ile Val Ser Leu Phe Phe Leu Trp
            20                  25                  30

Gly Met Ala Asn Asn Leu Asn Asp Ile Leu Ile Lys Gln Phe Lys Lys
        35                  40                  45

Ala Phe Glu Leu Ser Asp Leu Gln Ala Gly Leu Val Gln Ser Ala Phe
    50                  55                  60

Tyr Leu Gly Tyr Phe Val Phe Ala Met Pro Ala Ala Met Phe Met Arg
65                  70                  75                  80

Arg Tyr Ser Tyr Lys Ala Ala Val Val Leu Gly Leu Leu Leu Tyr Ala
                85                  90                  95

Cys Gly Ala Phe Leu Phe Tyr Pro Ala Ala Gln Val His Thr Tyr Trp
            100                 105                 110

Leu Phe Leu Leu Ala Leu Phe Val Ile Ala Ser Gly Leu Ala Phe Leu
        115                 120                 125

Glu Thr Thr Ala Asn Pro Leu Val Thr Val Leu Gly Pro Ala Asp Gly
    130                 135                 140

Ala Ala Arg Arg Leu Asn Leu Ala Gln Ala Phe Asn Pro Leu Gly Ser
145                 150                 155                 160

Ile Thr Gly Val Leu Val Gly Gln His Phe Ile Phe Ser Gly Val Glu
                165                 170                 175

His Thr Pro Ala Glu Leu Ala Ala Met Ala Pro Ala Ala Arg Glu Ala
            180                 185                 190

Phe Phe Ala Thr Glu Ser Ser Ala Val Gln Met Pro Tyr Leu Ile Ile
        195                 200                 205

Gly Val Val Val Val Leu Trp Ala Ile Leu Ile Ala Leu Val Arg Phe
    210                 215                 220

Pro Thr Gly Asp Ala Gly Val Gly Thr Ala Ala Pro Lys Arg Ala Lys
225                 230                 235                 240

Phe Gly Glu Leu Leu Arg Asn Arg Leu Phe Val Phe Ser Val Val Ala
                245                 250                 255
```

```
Gln Phe Phe Tyr Val Gly Ala Gln Val Gly Ile Trp Ser Tyr Leu Ile
            260                 265                 270

Arg Tyr Leu Gln Asp Ala Val Pro Gly Thr Pro Glu Lys Ser Ala Ala
        275                 280                 285

Thr Tyr Leu Thr Ile Ser Leu Val Leu Phe Met Ala Gly Arg Phe Val
    290                 295                 300

Gly Thr Ala Leu Leu Arg Tyr Leu Ala Pro Ala Lys Leu Leu Ala Ser
305                 310                 315                 320

Phe Ala Thr Ile Asn Leu Leu Leu Cys Ala Val Ala Ile Ala Leu Pro
                325                 330                 335

Gly Trp Thr Gly Leu Tyr Ala Leu Val Ala Ala Ser Val Phe Met Ser
            340                 345                 350

Val Met Phe Pro Thr Ile Phe Ala Leu Gly Leu Asp Gly Met His Asp
        355                 360                 365

Asp Ala Arg Lys Leu Gly Ser Ser Leu Leu Val Met Ala Ile Ile Gly
    370                 375                 380

Gly Ala Leu Leu Thr Ala Leu Met Gly Ala Val Ser Asp Met Ala Gly
385                 390                 395                 400

Ile His Trp Ala Met Val Val Pro Gly Val Cys Phe Gly Val Ile Leu
                405                 410                 415

Leu Phe Ala Leu Arg Ala Arg Arg Ala Ala Pro Val Val Ala Gly Ala
            420                 425                 430


<210> SEQ ID NO 29
<211> LENGTH: 1317
<212> TYPE: DNA
<213> ORGANISM: Salmonella enterica
<220> FEATURE:
<221> NAME/KEY: CDS
<222> LOCATION: (1)..(1317)

<400> SEQUENCE: 29

atg gga aac aca aca ata caa aca cag agt ttt cgt gct gtg gat gca       48
Met Gly Asn Thr Thr Ile Gln Thr Gln Ser Phe Arg Ala Val Asp Ala
1               5                   10                  15

gag caa agc aaa agc aag cgc tac att att cca ttc gcc tta ctt tgc       96
Glu Gln Ser Lys Ser Lys Arg Tyr Ile Ile Pro Phe Ala Leu Leu Cys
            20                  25                  30

tcg cta ttt ttt ctg tgg gcc gtc gcc aat aat ctg aat gac att tta      144
Ser Leu Phe Phe Leu Trp Ala Val Ala Asn Asn Leu Asn Asp Ile Leu
        35                  40                  45

tta ccg cag ttt caa caa gct ttt acg cta act aac ttt cag gcc ggg      192
Leu Pro Gln Phe Gln Gln Ala Phe Thr Leu Thr Asn Phe Gln Ala Gly
    50                  55                  60

ctt att cag tca gcc ttt tat ttc ggt tat ttc gtc att cca att ccc      240
Leu Ile Gln Ser Ala Phe Tyr Phe Gly Tyr Phe Val Ile Pro Ile Pro
65                  70                  75                  80

gct ggg att ttg atg aaa aaa ctc agt tat aaa gca ggg att atc acc      288
Ala Gly Ile Leu Met Lys Lys Leu Ser Tyr Lys Ala Gly Ile Ile Thr
                85                  90                  95

gga ctt ttt ttg tat gct gtt ggc gcc gca tta ttc tgg cct gcc gcc      336
Gly Leu Phe Leu Tyr Ala Val Gly Ala Ala Leu Phe Trp Pro Ala Ala
            100                 105                 110

gag ata atg aat tac aca ttg ttt tta att ggc ctg ttt atc atc gcc      384
Glu Ile Met Asn Tyr Thr Leu Phe Leu Ile Gly Leu Phe Ile Ile Ala
        115                 120                 125

gcc ggt tta ggc tgc ctt gaa act gcg gcc aac cct ttt gtt acg gta      432
Ala Gly Leu Gly Cys Leu Glu Thr Ala Ala Asn Pro Phe Val Thr Val
    130                 135                 140
```

```
tta ggt cca gaa agc ggc gga cat ttc cgg ctt aat ctg gcg caa act      480
Leu Gly Pro Glu Ser Gly Gly His Phe Arg Leu Asn Leu Ala Gln Thr
145                 150                 155                 160

ttt aac tcc ttt ggc gct att atc gcc gtt gtg ttt ggg caa agc ctt      528
Phe Asn Ser Phe Gly Ala Ile Ile Ala Val Val Phe Gly Gln Ser Leu
                165                 170                 175

att ttg tct aac gtg ccg cat caa tcg caa gaa gcg ctt gat aaa atg      576
Ile Leu Ser Asn Val Pro His Gln Ser Gln Glu Ala Leu Asp Lys Met
            180                 185                 190

acg ccg gat cag ctt agc gcc tat aaa cac agc ctg gtg tta tcg gta      624
Thr Pro Asp Gln Leu Ser Ala Tyr Lys His Ser Leu Val Leu Ser Val
        195                 200                 205

caa acg cca tac atg att atc gtc gcc atc gta tta gta gtt gcg cta      672
Gln Thr Pro Tyr Met Ile Ile Val Ala Ile Val Leu Val Val Ala Leu
    210                 215                 220

ctg att atg ctg acc aaa ttt ccg gcc ctg caa agt gac gat cat agc      720
Leu Ile Met Leu Thr Lys Phe Pro Ala Leu Gln Ser Asp Asp His Ser
225                 230                 235                 240

gat gct aaa caa agc tct ttc tta tct tct ctc tcc cga ctc atc cgt      768
Asp Ala Lys Gln Ser Ser Phe Leu Ser Ser Leu Ser Arg Leu Ile Arg
                245                 250                 255

atc cgc cac tgg cgc tgg gcg gtg ctg gcg cag ttc tgc tac gtg ggg      816
Ile Arg His Trp Arg Trp Ala Val Leu Ala Gln Phe Cys Tyr Val Gly
            260                 265                 270

gcg caa acc gcc tgc tgg agc tat ctg atc cgc tac gcc att gag gag      864
Ala Gln Thr Ala Cys Trp Ser Tyr Leu Ile Arg Tyr Ala Ile Glu Glu
        275                 280                 285

atc cct gga atg acg ccc ggt ttc gcc gcc aat tac ctg acc ggc acg      912
Ile Pro Gly Met Thr Pro Gly Phe Ala Ala Asn Tyr Leu Thr Gly Thr
    290                 295                 300

atg gtg tgc ttc ttt atc ggc cgt ttc acc ggg acc tgg ctt atc agc      960
Met Val Cys Phe Phe Ile Gly Arg Phe Thr Gly Thr Trp Leu Ile Ser
305                 310                 315                 320

cgc ttc gcg ccg cat aaa gtg ctg gcc gcc tac gcc ctg ttt gcc atg     1008
Arg Phe Ala Pro His Lys Val Leu Ala Ala Tyr Ala Leu Phe Ala Met
                325                 330                 335

ctc ctg tgt ctg att tcc gcc ttt agc ggc gga cat atc ggc ctg ctg     1056
Leu Leu Cys Leu Ile Ser Ala Phe Ser Gly Gly His Ile Gly Leu Leu
            340                 345                 350

gcg ctg acg ttg tgt agc gca ttt atg tca atc cag tac ccg acc atc     1104
Ala Leu Thr Leu Cys Ser Ala Phe Met Ser Ile Gln Tyr Pro Thr Ile
        355                 360                 365

ttc tcg ctg ggt atc aaa aat ctg gga cag gac act aag tac ggc tcg     1152
Phe Ser Leu Gly Ile Lys Asn Leu Gly Gln Asp Thr Lys Tyr Gly Ser
    370                 375                 380

tct ttt atc gtc atg acc atc att ggc ggc ggt att gtc acg cca gta     1200
Ser Phe Ile Val Met Thr Ile Ile Gly Gly Gly Ile Val Thr Pro Val
385                 390                 395                 400

atg ggc ttc gtt agc gac gcc gca ggc aaa atc ccg acc gcc gaa ctg     1248
Met Gly Phe Val Ser Asp Ala Ala Gly Lys Ile Pro Thr Ala Glu Leu
                405                 410                 415

gtt ccg gca ttg tgc ttt gcc gtc atc ttc att ttt gcc cgt ttc cgt     1296
Val Pro Ala Leu Cys Phe Ala Val Ile Phe Ile Phe Ala Arg Phe Arg
            420                 425                 430

tca caa gcg gcg aca aac tga                                         1317
Ser Gln Ala Ala Thr Asn
        435
```

<210> SEQ ID NO 30

<211> LENGTH: 438
<212> TYPE: PRT
<213> ORGANISM: Salmonella enterica

<400> SEQUENCE: 30

Met Gly Asn Thr Thr Ile Gln Thr Gln Ser Phe Arg Ala Val Asp Ala
1 5 10 15

Glu Gln Ser Lys Ser Lys Arg Tyr Ile Ile Pro Phe Ala Leu Leu Cys
20 25 30

Ser Leu Phe Phe Leu Trp Ala Val Ala Asn Asn Leu Asn Asp Ile Leu
35 40 45

Leu Pro Gln Phe Gln Gln Ala Phe Thr Leu Thr Asn Phe Gln Ala Gly
50 55 60

Leu Ile Gln Ser Ala Phe Tyr Phe Gly Tyr Phe Val Ile Pro Ile Pro
65 70 75 80

Ala Gly Ile Leu Met Lys Lys Leu Ser Tyr Lys Ala Gly Ile Ile Thr
85 90 95

Gly Leu Phe Leu Tyr Ala Val Gly Ala Ala Leu Phe Trp Pro Ala Ala
100 105 110

Glu Ile Met Asn Tyr Thr Leu Phe Leu Ile Gly Leu Phe Ile Ile Ala
115 120 125

Ala Gly Leu Gly Cys Leu Glu Thr Ala Ala Asn Pro Phe Val Thr Val
130 135 140

Leu Gly Pro Glu Ser Gly Gly His Phe Arg Leu Asn Leu Ala Gln Thr
145 150 155 160

Phe Asn Ser Phe Gly Ala Ile Ile Ala Val Val Phe Gly Gln Ser Leu
165 170 175

Ile Leu Ser Asn Val Pro His Gln Ser Gln Glu Ala Leu Asp Lys Met
180 185 190

Thr Pro Asp Gln Leu Ser Ala Tyr Lys His Ser Leu Val Leu Ser Val
195 200 205

Gln Thr Pro Tyr Met Ile Ile Val Ala Ile Val Leu Val Val Ala Leu
210 215 220

Leu Ile Met Leu Thr Lys Phe Pro Ala Leu Gln Ser Asp Asp His Ser
225 230 235 240

Asp Ala Lys Gln Ser Ser Phe Leu Ser Ser Leu Ser Arg Leu Ile Arg
245 250 255

Ile Arg His Trp Arg Trp Ala Val Leu Ala Gln Phe Cys Tyr Val Gly
260 265 270

Ala Gln Thr Ala Cys Trp Ser Tyr Leu Ile Arg Tyr Ala Ile Glu Glu
275 280 285

Ile Pro Gly Met Thr Pro Gly Phe Ala Ala Asn Tyr Leu Thr Gly Thr
290 295 300

Met Val Cys Phe Phe Ile Gly Arg Phe Thr Gly Thr Trp Leu Ile Ser
305 310 315 320

Arg Phe Ala Pro His Lys Val Leu Ala Ala Tyr Ala Leu Phe Ala Met
325 330 335

Leu Leu Cys Leu Ile Ser Ala Phe Ser Gly Gly His Ile Gly Leu Leu
340 345 350

Ala Leu Thr Leu Cys Ser Ala Phe Met Ser Ile Gln Tyr Pro Thr Ile
355 360 365

Phe Ser Leu Gly Ile Lys Asn Leu Gly Gln Asp Thr Lys Tyr Gly Ser
370 375 380

Ser Phe Ile Val Met Thr Ile Ile Gly Gly Gly Ile Val Thr Pro Val

-continued

```
385                 390                 395                 400

Met Gly Phe Val Ser Asp Ala Ala Gly Lys Ile Pro Thr Ala Glu Leu
                405                 410                 415

Val Pro Ala Leu Cys Phe Ala Val Ile Phe Ile Phe Ala Arg Phe Arg
            420                 425                 430

Ser Gln Ala Ala Thr Asn
        435
```

<210> SEQ ID NO 31
<211> LENGTH: 927
<212> TYPE: DNA
<213> ORGANISM: Agrobacterium tumefaciens

<400> SEQUENCE: 31

```
atgatcctgt gttgtggtga agccctgatc gacatgctgc cccggcagac gacgctgggt     60

gaggcgggct ttgcccctta cgcaggcgga gcggtcttca acacggcaat tgcgctgggg    120

cgtcttggcg tcccttcagc ctttttacc ggtctttccg acgacatgat gggcgatatc    180

ctgcgggaga ccctgcgggc cagcaaggtg gatttcagct attgcgccac cctgtcgcgc    240

cccaccacca ttgcgttcgt taagctggtt gatggccatg cgacctacgc tttttacgac    300

gagaacaccg ccggccggat gatcaccgag gccgaacttc cggccttggg agcggattgc    360

gaagcgctgc atttcggcgc catcagcctt attcccgaac cctgcggcag cacctatgag    420

gcgctgatga cgcgcgagca tgagacccgc gtcatctcgc tcgatccgaa cattcgtccc    480

ggcttcatcc agaacaagca gtcgcacatg gcccgcatcc gccgcatggc ggcgatgtct    540

gacatcgtca agttctcgga tgaggacctg gcgtggttcg gtctggaagg cgacgaggac    600

acgcttgccc gccactggct gcaccacggt gcaaaactcg tcgttgtcac ccgtggcgcc    660

aagggtgccg tgggttacag cgccaatctc aaggtggaag tggcctccga gcgcgtcgaa    720

gtggtcgata cggtcggcgc cggcgatacg ttcgatgccg gcattcttgc ttcgctgaaa    780

atgcagggcc tgctgaccaa agcgcaggtg gcttcgctga gcgaagagca gatcagaaaa    840

gctttggcgc ttggcgcgaa agccgctgcg gtcactgtct cgcgggctgg cgcaaatccg    900

cctttcgcgc atgaaatcgg tttgtga                                        927
```

<210> SEQ ID NO 32
<211> LENGTH: 308
<212> TYPE: PRT
<213> ORGANISM: Agrobacterium tumefaciens

<400> SEQUENCE: 32

```
Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
            20                  25                  30

Phe Asn Thr Ala Ile Ala Leu Gly Arg Leu Gly Val Pro Ser Ala Phe
        35                  40                  45

Phe Thr Gly Leu Ser Asp Asp Met Met Gly Asp Ile Leu Arg Glu Thr
    50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110
```

```
Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
                165                 170                 175

Ala Ala Met Ser Asp Ile Val Lys Phe Ser Asp Glu Asp Leu Ala Trp
            180                 185                 190

Phe Gly Leu Glu Gly Asp Glu Asp Thr Leu Ala Arg His Trp Leu His
        195                 200                 205

His Gly Ala Lys Leu Val Val Val Thr Arg Gly Ala Lys Gly Ala Val
    210                 215                 220

Gly Tyr Ser Ala Asn Leu Lys Val Glu Val Ala Ser Glu Arg Val Glu
225                 230                 235                 240

Val Val Asp Thr Val Gly Ala Gly Asp Thr Phe Asp Ala Gly Ile Leu
                245                 250                 255

Ala Ser Leu Lys Met Gln Gly Leu Leu Thr Lys Ala Gln Val Ala Ser
            260                 265                 270

Leu Ser Glu Glu Gln Ile Arg Lys Ala Leu Ala Leu Gly Ala Lys Ala
        275                 280                 285

Ala Ala Val Thr Val Ser Arg Ala Gly Ala Asn Pro Pro Phe Ala His
    290                 295                 300

Glu Ile Gly Leu
305
```

<210> SEQ ID NO 33
<211> LENGTH: 1404
<212> TYPE: DNA
<213> ORGANISM: Streptococcus mutans

<400> SEQUENCE: 33

```
cagctgatta tgcgtcagtt gaaaccctcg cttcttcagg aactgttgct gtaggtgata     60

gcttacttga agttaaaaaa taagaaatat tatcagaaag accgtaaggt ctttttgact    120

gcttaaaaga ttcagtaaca atagtattaa agccttttgg ctaactaata cttgaaattt    180

agcaaattat gatataatgt taagtagtcc ttaagggtag attaagggta ttcaaatcca    240

aaaattgatt tggtaagtta agtaaaatat aagaggttta ttatgtctaa attatatggc    300

agcatcgaag ctggcggaac aaaatttgtc tgtgctgtag gtgatgaaaa ttttcaaatt    360

ttagaaaaag ttcagttccc aacaacaaca ccttatgaaa caatagaaaa aacagttgct    420

ttctttaaaa aatttgaagc tgatttagcc agtgttgcca ttggttcttt tggccctatt    480

gatattgatc aaaattcaga cacttatggt tacattactt caacaccaaa gccaaactgg    540

gctaacgttg attttgtcgg cttaatttct aaagatttta aaattccatt ttactttacg    600

acagatgtta attcttctgc ttatggggaa acaattgctc gttcaaatgt taaaagtctg    660

gtttattata ctattggaac aggcattgga gcaggggcta ttcaaaatgg cgaattcatt    720

ggcggtatgg gacatacgga agctggacac gtttacatgg ctccgcatcc caatgatgtt    780

catcatggtt ttgtaggcac ctgtcctttc cataaaggct gtttagaagg acttgcagcg    840

ggtcctagct tagaggctcg tactggtatt cgtggtgagt taattgagca aaactcagaa    900

gtttgggata ttcaggcata ctacattgct caggcggcta ttcaagcgac tgtcctttat    960
```

-continued

```
cgtccgcaag tcattgtatt tggcggaggc gttatggcac aagaacatat gctcaatcgg   1020

gttcgtgaaa aatttacttc acttttgaat gactatcttc cagttccaga tgttaaagat   1080

tatattgtga caccagctgt tgcagaaaat ggttcagcaa cattgggaaa tctcgcttta   1140

gctaaaaaga tagcagcgcg ttaattaaaa atgaattgga agattaaagc accttctaat   1200

attcaatatt aaactgttag aatttacgtg aacgaaattt tcattttatg aggataatga   1260

agtgaatata attactcttg atttcctctg aaactagata gtggtatatt gaaaaacaga   1320

aaggagaaca ctatggaagg acctttgttt ttacaatcac aaatgcataa aaaaatctgg   1380

ggcggcaatc ggctcagaaa agaa                                          1404
```

<210> SEQ ID NO 34
<211> LENGTH: 293
<212> TYPE: PRT
<213> ORGANISM: Streptococcus mutans

<400> SEQUENCE: 34

```
Met Ser Lys Leu Tyr Gly Ser Ile Glu Ala Gly Gly Thr Lys Phe Val
1               5                   10                  15

Cys Ala Val Gly Asp Glu Asn Phe Gln Ile Leu Glu Lys Val Gln Phe
            20                  25                  30

Pro Thr Thr Thr Pro Tyr Glu Thr Ile Glu Lys Thr Val Ala Phe Phe
        35                  40                  45

Lys Lys Phe Glu Ala Asp Leu Ala Ser Val Ala Ile Gly Ser Phe Gly
    50                  55                  60

Pro Ile Asp Ile Asp Gln Asn Ser Asp Thr Tyr Gly Tyr Ile Thr Ser
65                  70                  75                  80

Thr Pro Lys Pro Asn Trp Ala Asn Val Asp Phe Val Gly Leu Ile Ser
                85                  90                  95

Lys Asp Phe Lys Ile Pro Phe Tyr Phe Thr Thr Asp Val Asn Ser Ser
            100                 105                 110

Ala Tyr Gly Glu Thr Ile Ala Arg Ser Asn Val Lys Ser Leu Val Tyr
        115                 120                 125

Tyr Thr Ile Gly Thr Gly Ile Gly Ala Gly Ala Ile Gln Asn Gly Glu
    130                 135                 140

Phe Ile Gly Gly Met Gly His Thr Glu Ala Gly His Val Tyr Met Ala
145                 150                 155                 160

Pro His Pro Asn Asp Val His His Gly Phe Val Gly Thr Cys Pro Phe
                165                 170                 175

His Lys Gly Cys Leu Glu Gly Leu Ala Ala Gly Pro Ser Leu Glu Ala
            180                 185                 190

Arg Thr Gly Ile Arg Gly Glu Leu Ile Glu Gln Asn Ser Glu Val Trp
        195                 200                 205

Asp Ile Gln Ala Tyr Tyr Ile Ala Gln Ala Ala Ile Gln Ala Thr Val
    210                 215                 220

Leu Tyr Arg Pro Gln Val Ile Val Phe Gly Gly Gly Val Met Ala Gln
225                 230                 235                 240

Glu His Met Leu Asn Arg Val Arg Glu Lys Phe Thr Ser Leu Leu Asn
                245                 250                 255

Asp Tyr Leu Pro Val Pro Asp Val Lys Asp Tyr Ile Val Thr Pro Ala
            260                 265                 270

Val Ala Glu Asn Gly Ser Ala Thr Leu Gly Asn Leu Ala Leu Ala Lys
        275                 280                 285
```

```
Lys Ile Ala Ala Arg
    290


<210> SEQ ID NO 35
<211> LENGTH: 924
<212> TYPE: DNA
<213> ORGANISM: Escherichia coli

<400> SEQUENCE: 35

ttacttctca ctttccagtt cttgtcgaca tggcagcgct gtcattgccc ctttcgctgt     60

tactgcaagc gctccgcaac gttgagcgag atcgataatt cgtcgcattt ctctctcatc    120

tgtagataat cccgtagagg acagacctgt gagtaacccg gcaacgaacg catctcccgc    180

cccagtgcta tcgacacaat tcacagacat tccagcaaaa tggtggactt gtcctcgata    240

acagaccacc accccttctg cacctttagt caccaacagc atggcgatct catactcttt    300

tgccagggcg catatatccc gatcgttctg tgtttttcca ctgataagtc gccattcttc    360

ttccgagagc ttgacgacat ccgccagttg tagcgcctgc cgcaaacaca agcggagcaa    420

atgctcgtct tgccatagat cttcacgaat attgggatcg aagctgacaa aacctccggc    480

atgccggatc gccgtcatcg cagtaaatgc gctggtacgc gaaggctcgg cagacaacgc    540

aattgaacag agatgtaacc attcgccatg tcgccagcag ggcaagtctg tcgtctctaa    600

aaaaagatcg gcactggggc ggaccataaa cgtaaatgaa cgttctcctt gatcgttcag    660

atcgacaagc accgtggatg tccggtgcca ttcatcttgc ttcagatacg tgatatcgac    720

accctcagtt agcagcgttc tttgcattaa cgcaccaaaa ggatcatcac cgacccgacc    780

tataaaccca cttgttccgc ctaatctggc gattcccacc gcaacgttag ctggcgcgcc    840

gccaggacaa ggcagtagcc gcccgtctga ttctggcaag agatctacga ccgcatcccc    900

taaaacccat actttggctg acat                                           924


<210> SEQ ID NO 36
<211> LENGTH: 307
<212> TYPE: PRT
<213> ORGANISM: Escherichia coli

<400> SEQUENCE: 36

Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
```

```
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Glu Trp Arg
            180                 185                 190

Leu Ile Ser Gly Lys Thr Gln Asn Asp Arg Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

Ser Glu Lys
305
```

<210> SEQ ID NO 37
<211> LENGTH: 879
<212> TYPE: DNA
<213> ORGANISM: Enterococcus faecalis

<400> SEQUENCE: 37

```
atgacagaaa aacttttagg aagtatcgaa gccggtggca caaaatttgt atgtggcgtt     60

gggacagatg atttgaccat cgtagaacgt gtcagttttc ccacaacaac cccagaagaa    120

acaatgaaaa aagtaataga atttttccaa caatatcctt taaaagcgat tgggattggt    180

tcatttggtc cgattgatat tcacgttgat tctcctacgt atggttatat cacttctaca    240

ccaaaattag cttggcgtaa ctttgacttg ttaggaacta tgaaacaaca ttttgatgtg    300

ccaatggctt ggacaacgga tgtgaatgct gcggcatatg gtgagtatgt tgctggaaat    360

gggcaacata catctagttg tgtatattat acaattggaa ctggtgttgg cgctggagcg    420

attcaaaacg gtgagtttat tgaaggcttt agccacccag aaatggggca tgcgttagtt    480

cgtcgtcatc ctgaagatac gtatgcagga aattgtcctt atcatggaga ttgtttagaa    540

gggattgcag caggaccagc agttgaaggt cgttctggta aaaaaggaca tttattggaa    600

gaggatcata aaacttggga attagaagct tattatttag cgcaagcggc gtacaatacg    660

actttattat tagcgccaga agtgatcatt ttaggtggcg gcgtcatgaa acaacgtcat    720

ttgatgccga aagttcgtga aaaatttgct gaattagtca atggatatgt ggaaacaccg    780

cctttagaaa aatacttggt gacgcctctt ttagaagata atccaggaac aatcggttgc    840

tttgccttgg caaaaaaagc tttaatggct caaaaataa                           879
```

<210> SEQ ID NO 38
<211> LENGTH: 292
<212> TYPE: PRT
<213> ORGANISM: Enterococcus faecalis

<400> SEQUENCE: 38

```
Met Thr Glu Lys Leu Leu Gly Ser Ile Glu Ala Gly Gly Thr Lys Phe
```

-continued

```
1               5                   10                  15

Val Cys Gly Val Gly Thr Asp Asp Leu Thr Ile Val Glu Arg Val Ser
            20                  25                  30

Phe Pro Thr Thr Thr Pro Glu Glu Thr Met Lys Lys Val Ile Glu Phe
        35                  40                  45

Phe Gln Gln Tyr Pro Leu Lys Ala Ile Gly Ile Gly Ser Phe Gly Pro
    50                  55                  60

Ile Asp Ile His Val Asp Ser Pro Thr Tyr Gly Tyr Ile Thr Ser Thr
65                  70                  75                  80

Pro Lys Leu Ala Trp Arg Asn Phe Asp Leu Leu Gly Thr Met Lys Gln
                85                  90                  95

His Phe Asp Val Pro Met Ala Trp Thr Thr Asp Val Asn Ala Ala Ala
            100                 105                 110

Tyr Gly Glu Tyr Val Ala Gly Asn Gly Gln His Thr Ser Ser Cys Val
        115                 120                 125

Tyr Tyr Thr Ile Gly Thr Gly Val Gly Ala Gly Ala Ile Gln Asn Gly
    130                 135                 140

Glu Phe Ile Glu Gly Phe Ser His Pro Glu Met Gly His Ala Leu Val
145                 150                 155                 160

Arg Arg His Pro Glu Asp Thr Tyr Ala Gly Asn Cys Pro Tyr His Gly
                165                 170                 175

Asp Cys Leu Glu Gly Ile Ala Ala Gly Pro Ala Val Glu Gly Arg Ser
            180                 185                 190

Gly Lys Lys Gly His Leu Leu Glu Glu Asp His Lys Thr Trp Glu Leu
        195                 200                 205

Glu Ala Tyr Tyr Leu Ala Gln Ala Ala Tyr Asn Thr Thr Leu Leu Leu
    210                 215                 220

Ala Pro Glu Val Ile Ile Leu Gly Gly Gly Val Met Lys Gln Arg His
225                 230                 235                 240

Leu Met Pro Lys Val Arg Glu Lys Phe Ala Glu Leu Val Asn Gly Tyr
                245                 250                 255

Val Glu Thr Pro Pro Leu Glu Lys Tyr Leu Val Thr Pro Leu Leu Glu
            260                 265                 270

Asp Asn Pro Gly Thr Ile Gly Cys Phe Ala Leu Ala Lys Lys Ala Leu
        275                 280                 285

Met Ala Gln Lys
    290
```

<210> SEQ ID NO 39
<211> LENGTH: 1458
<212> TYPE: DNA
<213> ORGANISM: Saccharomyces cerevisiae

<400> SEQUENCE: 39

```
ttaagcgcca atgataccaa gagacttacc ttcggcaatt ctttttcgg acaatgcagc      60

aataacagca gcacctgcac ctgaaccatc ctcagctgga acaatcgtaa ttggatcttt     120

gcttgcgtca ccagtccatc catagatatc tctcaaaccc ttagcggcgg cttccttgaa     180

acctgggtat ttgttataga cagaaccgtc agcggcaatg tgaccagtct tgtaacctct     240

cttttggcaa atagcggcaa taccacaaac agctaatcta gcagctctgg taccgatcaa     300

ttcacaaagt cttctaatca acttacgttc tggcagagtg gtcttgacac caaagtcctt     360

ttggaagatg tcatcagtat cttccaagtt ttcaaatgga tcatcctcga ttcttgctgg     420

gtaggaggta tccatgatgt atggttgttt caacttgctt agatcttgat ccttcaacat     480
```

```
caagcccttc tcgtttaatt caagtaacac tagacgcaac aattcaccca agtagtaacc    540

ggaggtcatc ttttcaaaag cttgttgacc aggtcttgga gattgttcgt cgacagcaac    600

atcgtacttg gttcttggca agaccaaatg ttcattatcg aaggaaccat attcacaatt    660

gatagccatt ggagagttac ttggaatatc gtctgctaat ttgccctcca acttttcgat    720

atcggaaaca acatcataga aagcaccgtt gacaccagta ccgaaaatca cacccatctt    780

agtctctggg tcagtgtagt atgaggcaat taaagtacca acagtatcat taatcaatgc    840

tacaatttca ataggcaact ctctcttgga aatttcgttt tgtagcaatg ggacgacatc    900

gtggccttcg acatttggaa tatcgaaacc cttggtccat ctttgcaaaa taccttcgtt    960

aatcttgttt tgggaagctg ggtacgagaa ggtgaaacct aatggtaagg tgtccttggt   1020

gtttagcaat tcttgctcga ccataaagtc cttcaaagag tcggcaataa aggaccataa   1080

ctcctcttgg tgcttagtgg ttctcatgtc atgtggtagt ttatacttgg attgagtggt   1140

gtcaaaggta tggttaccgc tcaacttgac caacacgact cttaagttag taccacccaa   1200

atcaatggcc aaatagttac cagattcttt acctgttggg aattccatga cccaaccggg   1260

aatcattgga atgttacctc ccttctttgt caaaccttta ttcaattcgt cgataaagtg   1320

cttaacaacc tttctcaagg tctcgctgtc aactgtaaac atatcttcca actgatgaat   1380

ttcatccatc aattccttgg gcacatcagc catggaaccc tttctagcct gtggtttctt   1440

tggacctaaa tgaaccat                                                 1458
```

<210> SEQ ID NO 40
<211> LENGTH: 485
<212> TYPE: PRT
<213> ORGANISM: Saccharomyces cerevisiae

<400> SEQUENCE: 40

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
    50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190
```

```
Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
    210                 215                 220

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
    290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Asp Ile Phe Gln Lys Asp
        355                 360                 365

Phe Gly Val Lys Thr Thr Leu Pro Glu Arg Lys Leu Ile Arg Arg Leu
    370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
        435                 440                 445

Pro Ile Thr Ile Val Pro Ala Glu Asp Gly Ser Gly Ala Gly Ala Ala
    450                 455                 460

Val Ile Ala Ala Leu Ser Glu Lys Arg Ile Ala Glu Gly Lys Ser Leu
465                 470                 475                 480

Gly Ile Ile Gly Ala
                485


<210> SEQ ID NO 41
<211> LENGTH: 1461
<212> TYPE: DNA
<213> ORGANISM: Saccharomyces cerevisiae

<400> SEQUENCE: 41

atggttcatt taggtccaaa aaaaccacaa gccagaaagg gttccatggc cgatgtgcca      60

aaggaattga tgcaacaaat tgagaatttt gaaaaaattt tcactgttcc aactgaaact     120

ttacaagccg ttaccaagca cttcatttcc gaattggaaa agggtttgtc caagaagggt     180

ggtaacattc caatgattcc aggttgggtt atggatttcc caactggtaa ggaatccggt     240

gatttcttgg ccattgattt gggtggtacc aacttgagag ttgtcttagt caagttgggc     300

ggtgaccgta cctttgacac cactcaatct aagtacagat taccagatgc tatgagaact     360

actcaaaatc cagacgaatt gtgggaattt attgccgact ctttgaaagc ttttattgat     420
```

-continued

```
gagcaattcc cacaaggtat ctctgagcca attccattgg gtttcacctt ttctttccca    480

gcttctcaaa acaaaatcaa tgaaggtatc ttgcaaagat ggactaaagg ttttgatatt    540

ccaaacattg aaaaccacga tgttgttcca atgttgcaaa agcaaatcac taagaggaat    600

atcccaattg aagttgttgc tttgataaac gacactaccg gtactttggt tgcttcttac    660

tacactgacc cagaaactaa gatgggtgtt atcttcggta ctggtgtcaa tggtgcttac    720

tacgatgttt gttccgatat cgaaaagcta caaggaaaac tatctgatga cattccacca    780

tctgctccaa tggccatcaa ctgtgaatac ggttccttcg ataatgaaca tgtcgttttg    840

ccaagaacta aatacgatat caccattgat gaagaatctc caagaccagg ccaacaaacc    900

tttgaaaaaa tgtcttctgg ttactactta ggtgaaattt tgcgtttggc cttgatggac    960

atgtacaaac aaggtttcat cttcaagaac caagacttgt ctaagttcga caagcctttc   1020

gtcatggaca cttcttaccc agccagaatc gaggaagatc cattcgagaa cctagaagat   1080

accgatgact tgttccaaaa tgagttcggt atcaacacta ctgttcaaga acgtaaattg   1140

atcagacgtt tatctgaatt gattggtgct agagctgcta gattgtccgt ttgtggtatt   1200

gctgctatct gtcaaaagag aggttacaag accggtcaca tcgctgcaga cggttccgtt   1260

tacaacagat acccaggttt caaagaaaag gctgccaatg ctttgaagga catttacggc   1320

tggactcaaa cctcactaga cgactaccca atcaagattg ttcctgctga agatggttcc   1380

ggtgctggtg ccgctgttat tgctgctttg gcccaaaaaa gaattgctga aggtaagtcc   1440

gttggtatca tcggtgctta a                                             1461
```

<210> SEQ ID NO 42
<211> LENGTH: 486
<212> TYPE: PRT
<213> ORGANISM: Saccharomyces cerevisiae

<400> SEQUENCE: 42

```
Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190
```

```
Gln Lys Gln Ile Thr Lys Arg Asn Ile Pro Ile Glu Val Val Ala Leu
        195                 200                 205

Ile Asn Asp Thr Thr Gly Thr Leu Val Ala Ser Tyr Tyr Thr Asp Pro
    210                 215                 220

Glu Thr Lys Met Gly Val Ile Phe Gly Thr Gly Val Asn Gly Ala Tyr
225                 230                 235                 240

Tyr Asp Val Cys Ser Asp Ile Glu Lys Leu Gln Gly Lys Leu Ser Asp
                245                 250                 255

Asp Ile Pro Pro Ser Ala Pro Met Ala Ile Asn Cys Glu Tyr Gly Ser
            260                 265                 270

Phe Asp Asn Glu His Val Val Leu Pro Arg Thr Lys Tyr Asp Ile Thr
        275                 280                 285

Ile Asp Glu Glu Ser Pro Arg Pro Gly Gln Gln Thr Phe Glu Lys Met
    290                 295                 300

Ser Ser Gly Tyr Tyr Leu Gly Glu Ile Leu Arg Leu Ala Leu Met Asp
305                 310                 315                 320

Met Tyr Lys Gln Gly Phe Ile Phe Lys Asn Gln Asp Leu Ser Lys Phe
                325                 330                 335

Asp Lys Pro Phe Val Met Asp Thr Ser Tyr Pro Ala Arg Ile Glu Glu
            340                 345                 350

Asp Pro Phe Glu Asn Leu Glu Asp Thr Asp Asp Leu Phe Gln Asn Glu
        355                 360                 365

Phe Gly Ile Asn Thr Thr Val Gln Glu Arg Lys Leu Ile Arg Arg Leu
    370                 375                 380

Ser Glu Leu Ile Gly Ala Arg Ala Ala Arg Leu Ser Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Arg Tyr Pro Gly Phe Lys Glu Lys Ala Ala
            420                 425                 430

Asn Ala Leu Lys Asp Ile Tyr Gly Trp Thr Gln Thr Ser Leu Asp Asp
        435                 440                 445

Tyr Pro Ile Lys Ile Val Pro Ala Glu Asp Gly Ser Gly Ala Gly Ala
    450                 455                 460

Ala Val Ile Ala Ala Leu Ala Gln Lys Arg Ile Ala Glu Gly Lys Ser
465                 470                 475                 480

Val Gly Ile Ile Gly Ala
                485
```

<210> SEQ ID NO 43
<211> LENGTH: 1164
<212> TYPE: DNA
<213> ORGANISM: Klebsiella pneumoniae

<400> SEQUENCE: 43

```
tcagaatgcc tggcggaaaa tcgcggcaat ctcctgctcg ttgcctttac gcgggttcga      60

gaacgcattg ccgtctttca gagccatctc cgccatgtag gggaagtcgg cctcttttac     120

tcccagatcg cgcagatgct gcggaatacc gatatccatc gacagacgcg tgatagcggc     180

gatggctttt tccgccgcgt cgagagtgga cagtccggtg atattttcgc ccatcagttc     240

agcgatatcg gcgaatttct ccgggttggc gatcaggttg tagcgggcca catgcggcag     300

caggacagcg ttggccacgc cgtgcggcat gtcgtacagg ccgcccagct ggtgcgccat     360

ggcgtgcacg tagccgaggt tggcgttatt gaaagccatc ccggccagca gagaggcata     420
```

```
ggccatgttt tcccgcgcct gcagattgct gccgagggcc acggcctggc gcaggttgcg    480

ggcgatgagg cggatcgcct gcatggcggc ggcgtccgtc accgggttag cgtctttgga    540

gatataggcc tctacggcgt gggtcagggc atccatcccg gtcgccgcgg tcagggcggc    600

cggtttaccg atcatcagca gcggatcgtt gatagagacc gacggcaggt tgcgccagct    660

gacgatcaca aacttcactt tggtttcggt gttggtcagg acgcagtggc gggtgacctc    720

gctggcggtg ccggcggtgg tattgaccgc gacgataggc ggcagcgggt tggtcagggt    780

ctcgattccg gcatactggt acagatcgcc ctcatgggtg gcggcgatgc cgatgccttt    840

gccgcaatcg tgcgggctgc cgccgcccac ggtgacgatg atgtcgcact gttcgcggcg    900

aaacacggcg aggccgtcgc gcacgttggt gtctttcggg ttcggctcga cgccgtcaaa    960

gatcgccacc tcgatcccgg cctcccgcag ataatgcagg gttttgtcca ctgcgccatc   1020

tttaattgcc cgcaggcctt tgtcggtgac cagcagggct tttttccccc ccagcagctg   1080

gcagcgttcg ccgactacgg aaatggcgtt ggggccaaaa aagttaacgt ttggcaccag   1140

ataatcaaac atacgatagc tcat                                          1164
```

<210> SEQ ID NO 44
<211> LENGTH: 387
<212> TYPE: PRT
<213> ORGANISM: Klebsiella pneumoniae

<400> SEQUENCE: 44

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu His Tyr Leu Arg Glu Ala Gly Ile
    50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Ala Met Gln Ala Ile
    210                 215                 220

Arg Leu Ile Ala Arg Asn Leu Arg Gln Ala Val Ala Leu Gly Ser Asn
225                 230                 235                 240
```

```
Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
                325                 330                 335

Asp Ile Gly Ile Pro Gln His Leu Arg Asp Leu Gly Val Lys Glu Ala
            340                 345                 350

Asp Phe Pro Tyr Met Ala Glu Met Ala Leu Lys Asp Gly Asn Ala Phe
        355                 360                 365

Ser Asn Pro Arg Lys Gly Asn Glu Gln Glu Ile Ala Ala Ile Phe Arg
    370                 375                 380

Gln Ala Phe
385
```

<210> SEQ ID NO 45
<211> LENGTH: 1824
<212> TYPE: DNA
<213> ORGANISM: Klebsiella pneumoniae

<400> SEQUENCE: 45

```
atgccgttaa tagccgggat tgatatcggc aacgccacca ccgaggtggc gctggcgtcc     60

gactacccgc aggcgagggc gtttgttgcc agcgggatcg tcgcgacgac gggcatgaaa    120

gggacgcggg acaatatcgc cgggaccctc gccgcgctgg agcaggccct ggcgaaaaca    180

ccgtggtcga tgagcgatgt ctctcgcatc tatcttaacg aagccgcgcc ggtgattggc    240

gatgtggcga tggagaccat caccgagacc attatcaccg aatcgaccat gatcggtcat    300

aacccgcaga cgccgggcgg ggtgggcgtt ggcgtgggga cgactatcgc cctcgggcgg    360

ctggcgacgc tgccggcggc gcagtatgcc gaggggtgga tcgtactgat tgacgacgcc    420

gtcgatttcc ttgacgccgt gtggtggctc aatgaggcgc tcgaccgggg gatcaacgtg    480

gtggcggcga tcctcaaaaa ggacgacggc gtgctggtga acaaccgcct gcgtaaaacc    540

ctgccggtgg tggatgaagt gacgctgctg gagcaggtcc ccgagggggt aatggcggcg    600

gtggaagtgg ccgcgccggg ccaggtggtg cggatcctgt cgaatcccta cgggatcgcc    660

accttcttcg ggctaagccc ggaagagacc caggccatcg tccccatcgc ccgcgccctg    720

attggcaacc gttccgcggt ggtgctcaag accccgcagg gggatgtgca gtcgcgggtg    780

atcccggcgg gcaacctcta cattagcggc gaaaagcgcc gcggagaggc cgatgtcgcc    840

gagggcgcgg aagccatcat gcaggcgatg agcgcctgcg ctccggtacg cgacatccgc    900

ggcgaaccgg gcacccacgc cggcggcatg cttgagcggg tgcgcaaggt aatggcgtcc    960

ctgaccggcc atgagatgag cgcgatatac atccaggatc tgctggcggt ggatacgttt   1020

attccgcgca aggtgcaggg cgggatggcc ggcgagtgcg ccatggagaa tgccgtcggg   1080

atggcggcga tggtgaaagc ggatcgtctg caaatgcagg ttatcgcccg cgaactgagc   1140

gcccgactgc agaccgaggt ggtggtgggc ggcgtggagg ccaacatggc catcgccggg   1200
```

-continued

```
gcgttaacca ctcccggctg tgcggcgccg ctggcgatcc tcgacctcgg cgccggctcg   1260

acggatgcgg cgatcgtcaa cgcggagggg cagataacgg cggtccatct cgccggggcg   1320

gggaatatgg tcagcctgtt gattaaaacc gagctgggcc tcgaggatct ttcgctggcg   1380

gaagcgataa aaaaataccc gctggccaaa gtggaaagcc tgttcagtat tcgtcacgag   1440

aatggcgcgg tggagttctt tcgggaagcc ctcagcccgg cggtgttcgc caaagtggtg   1500

tacatcaagg agggcgaact ggtgccgatc gataacgcca gcccgctgga aaaaattcgt   1560

ctcgtgcgcc ggcaggcgaa agagaaagtg tttgtcacca actgcctgcg cgcgctgcgc   1620

caggtctcac ccggcggttc cattcgcgat atcgcctttg tggtgctggt gggcggctca   1680

tcgctggact ttgagatccc gcagcttatc acggaagcct tgtcgcacta tggcgtggtc   1740

gccgggcagg gcaatattcg gggaacagaa gggccgcgca atgcggtcgc caccgggctg   1800

ctactggccg gtcaggcgaa ttaa                                          1824
```

<210> SEQ ID NO 46
<211> LENGTH: 13669
<212> TYPE: DNA
<213> ORGANISM: Artificial Sequence
<220> FEATURE:
<223> OTHER INFORMATION: Plasmid

<400> SEQUENCE: 46

```
tagtaaagcc ctcgctagat tttaatgcgg atgttgcgat tacttcgcca actattgcga     60

taacaagaaa aagccagcct ttcatgatat atctcccaat ttgtgtaggg cttattatgc    120

acgcttaaaa ataataaaag cagacttgac ctgatagttt ggctgtgagc aattatgtgc    180

ttagtgcatc taacgcttga gttaagccgc gccgcgaagc ggcgtcggct tgaacgaatt    240

gttagacatt atttgccgac taccttggtg atctcgcctt tcacgtagtg gacaaattct    300

tccaactgat ctgcgcgcga ggccaagcga tcttcttctt gtccaagata agcctgtcta    360

gcttcaagta tgacgggctg atactgggcc ggcaggcgct ccattgccca gtcggcagcg    420

acatccttcg gcgcgatttt gccggttact gcgctgtacc aaatgcggga caacgtaagc    480

actacatttc gctcatcgcc agcccagtcg ggcggcgagt tccatagcgt taaggtttca    540

tttagcgcct caaatagatc ctgttcagga accggatcaa agagttcctc cgccgctgga    600

cctaccaagg caacgctatg ttctcttgct tttgtcagca agatagccag atcaatgtcg    660

atcgtggctg gctcgaagat acctgcaaga atgtcattgc gctgccattc tccaaattgc    720

agttcgcgct tagctggata acgccacgga atgatgtcgt cgtgcacaac aatggtgact    780

tctacagcgc ggagaatctc gctctctcca ggggaagccg aagtttccaa aaggtcgttg    840

atcaaagctc gccgcgttgt ttcatcaagc cttacggtca ccgtaaccag caaatcaata    900

tcactgtgtg gcttcaggcc gccatccact gcggagccgt acaaatgtac ggccagcaac    960

gtcggttcga gatggcgctc gatgacgcca actacctctg atagttgagt cgatacttcg   1020

gcgatcaccg cttccctcat gatgtttaac tttgttttag ggcgactgcc ctgctgcgta   1080

acatcgttgc tgctccataa catcaaacat cgacccacgg cgtaacgcgc ttgctgcttg   1140

gatgcccgag gcatagactg taccccaaaa aaacagtcat aacaagccat gaaaaccgcc   1200

actgcgccgt taccaccgct gcgttcggtc aaggttctgg accagttgcg tgagcgcata   1260

cgctacttgc attacagctt acgaaccgaa caggcttatg tccactgggt tcgtgccttc   1320

atccgtttcc acggtgtgcg tcacccggca accttgggca gcagcgaagt cgaggcattt   1380

ctgtcctggc tggcgaacga gcgcaaggtt tcggtctcca cgcatcgtca ggcattggcg   1440
```

-continued

```
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420
ttttttgttt atattcaagt ggttataatt tatagaataa agaaagaata aaaaaagata   3480
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
```

-continued

```
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcagggggtc ccctgccaga   4860
ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000
acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
```

-continued

```
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttattttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
```

```
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc tttttttcttg  10500
tctagagtac tggcgaaagg gggatgtgct gcaaggcgat taagttgggt aacgccaggg  10560
ttttcccagt cacgacgttg taaaacgacg gccagtgaat tcgagctcgg tacccggggc  10620
ggccgcgcta gcgcccgatc cagctggagt ttgtagaaac gcaaaaaggc catccgtcag  10680
gatggccttc tgcttaattt gatgcctggc agtttatggc gggcgtcctg cccgccaccc  10740
tccgggccgt tgcttcgcaa cgttcaaatc cgctcccggc ggatttgtcc tactcaggag  10800
agcgttcacc gacaaacaac agataaaacg aaaggcccag tctttcgact gagcctttcg  10860
ttttatttga tgcctggcag ttccctactc tcgcatgggg agaccccaca ctaccatcgg  10920
```

-continued

```
cgctacggcg tttcacttct gagttcggca tggggtcagg tgggaccacc gcgctactgc  10980
cgccaggcaa attctgtttt atcagaccgc ttctgcgttc tgatttaatc tgtatcaggc  11040
tgaaaatctt ctctcatccg ccaaaacagc caagcttgca tgcctgcagc ccgggttacc  11100
atttcaacag atcgtcctta gcatataagt agtcgtcaaa aatgaattca acttcgtctg  11160
tttcggcatt gtagccgcca actctgatgg attcgtggtt tttgacaatg atgtcacagc  11220
ctttttcctt taggaagtcc aagtcgaaag tagtggcaat accaatgatc ttacaaccgg  11280
cggcttttcc ggcggcaata cctgctggag cgtcttcaaa tactactacc ttagatttgg  11340
aagggtcttg ctcattgatc ggatatccta agccattcct gcccttcaga tatggttctg  11400
gatgaggctt accctgtttg acatcattag cggtaatgaa gtactttggt ctcctgattc  11460
ccagatgctc gaaccatttt tgtgccatat cacgggtacc ggaagttgcc acagcccatt  11520
tctcttttgg tagagcgttc aaagcgttgc acagcttaac tgcacctggg acttcaatgg  11580
atttttcacc gtacttgacc ggaatttcag cttctaattt gttaacatac tcttcattgg  11640
caaagtctgg agcgaactta gcaatggcat caaacgttct ccaaccatgc gagacttgga  11700
taacgtgttc agcatcgaaa taaggtttgt ccttaccgaa atccctccag aatgcagcaa  11760
tggctggttg agagatgata atggtaccgt cgacgtcgaa caaagcggcg ttaactttca  11820
aagatagagg tttagtagtc aatcccataa ttctagtctg tttcctggat ccaataaatc  11880
taatcttcat gtagatctaa ttcttcaatc atgtccggca ggttcttcat tgggtagttg  11940
ttgtaaacga tttggtatac ggcttcaaat aatgggaagt cttcgacaga gccacatgtt  12000
tccaaccatt cgtgaacttc tttgcaggta attaaacctt gagcggattg gccattcaac  12060
aactcctttt cacattccca ggcgtcctta ccagaagtag ccattagcct agcaaccttg  12120
acgtttctac caccagcgca ggtggtgatc aaatcagcaa caccagcaga ctcttggtag  12180
tatgtttctt ctctagattc tgggaaaaac atttgaccga atctgatgat ctcacccaaa  12240
ccgactcttt ggatggcagc agaagcgttg ttaccccagc ctagaccttc gacgaaacca  12300
caacctaagg caacaacgtt cttcaaagca ccacagatgg agataccagc aacatcttcg  12360
atgacactaa cgtggaagta aggtctgtgg aacaaggcct ttagaacctt atggtcgacg  12420
tccttgccct cgcctctgaa atcctttgga atgtggtaag caactgttgt ttcagaccag  12480
tgttcttgag cgacttcggt ggcaatgtta gcaccagata gagcaccaca ttgaatacct  12540
agttcctcag tgatgtaaga ggatagcaat tggacacctt tagcaccaac ttcaaaaccc  12600
tttagacagg agatagctct gacgtgtgaa tcaacatgac ctttcaattg gctacagata  12660
cggggcaaaa attgatgtgg aatgttgaaa acgatgatgt cgacatcctt gactgaatca  12720
atcaagtctg gattagcaac caaattgtcg ggtagagtga tgccaggcaa gtatttcacg  12780
ttttgatgtc tagtatttat gatttcagtc aatttttcac cattgatctc ttcttcgaac  12840
acccacattt gtactattgg agcgaaaact tctgggtatc ccttacaatt ttcggcaacc  12900
accttggcaa tagtagtacc ccagttacca gatccaatca cagtaacctt gaaaggcttt  12960
tcggcagcct tcaaagaaac agaagaggaa cttctctttc taccagcatt caagtggccg  13020
gaagttaagt ttaatctatc agcagcagca gccatggaat tgtcctcctt actagtcatg  13080
gtctgtttcc tgtgtgaaat tgttatccgc tcacaattcc acacattata cgagccggat  13140
gattaattgt caacagctca tttcagaata tttgccagaa ccgttatgat gtcggcgcaa  13200
aaaacattat ccagaacggg agtgcgcctt gagcgacacg aattatgcag tgatttacga  13260
```

-continued

```
cctgcacagc cataccacag cttccgatgg ctgcctgacg ccagaagcat tggtgcacgc  13320
tagccagtac atttaaatgg taccctctag tcaaggcctt aagtgagtcg tattacggac  13380
tggccgtcgt tttacaacgt cgtgactggg aaaaccctgg cgttacccaa cttaatcgcc  13440
ttgcagcaca tccccctttc gccagctggc gtaatagcga agaggcccgc accgatcgcc  13500
cttcccaaca gttgcgcagc ctgaatggcg aatggcgcct gatgcggtat tttctcctta  13560
cgcatctgtg cggtatttca caccgcatat ggtgcactct cagtacaatc tgctctgatg  13620
ccgcatagtt aagccagccc cgacacccgc caacacccgc tgacgagct             13669
```

<210> SEQ ID NO 47
<211> LENGTH: 13543
<212> TYPE: DNA
<213> ORGANISM: Artificial Sequence
<220> FEATURE:
<223> OTHER INFORMATION: Plasmid

<400> SEQUENCE: 47

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
```

-continued

```
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420
tttttgttt atattcaagt ggttataatt tatagaataa agaaagaata aaaaaagata   3480
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
```

-continued

```
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcagggggtc ccctgccaga   4860
ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700
tgtgctgttt gccacggtat gcagcaccag cgcgagatta tgggctcgca cgctcgactg   5760
tcggacgggg gcactggaac gagaagtcag gcgagccgtc acgcccttga ctatgccaca   5820
tcctgagcaa ataattcaac cactaaacaa atcaaccgcg tttcccggag gtaaccaagc   5880
ttcacctttt gagccgatga acaatgaaaa gatcaaaacg atttgcagta ctggcccagc   5940
gccccgtcaa tcaggacggg ctgattggcg agtggcctga agaggggctg atcgccatgg   6000
acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccggaccccc tccaaccagt gccacgtcac caatctcaaa gataatccgg   6360
tgcagattgc cgctgacgcc gccgaggccg ggatccgcgg cttctcagaa caggagacca   6420
```

-continued

```
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg ggctattcgg   6720
agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttattttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
```

-continued

```
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagcgtgc accaatgctt ctggcgtcag gcagccatcg gaagctgtgg tatggctgtg  10560
caggtcgtaa atcactgcat aattcgtgtc gctcaaggcg cactcccgtt ctggataatg  10620
ttttttgcgc cgacatcata acggttctgg caaatattct gaaatgagct gttgacaatt  10680
aatcatccgg ctcgtataat gtgtggaatt gtgagcggat aacaatttca cacaggaaac  10740
agaccatgac tagtaaggag gacaattcca tggctgctgc tgctgataga ttaaacttaa  10800
cttccggcca cttgaatgct ggtagaaaga gaagttcctc ttctgtttct ttgaaggctg  10860
ccgaaaagcc tttcaaggtt actgtgattg gatctggtaa ctggggtact actattgcca  10920
aggtggttgc cgaaaattgt aagggatacc cagaagtttt cgctccaata gtacaaatgt  10980
gggtgttcga agaagagatc aatggtgaaa aattgactga aatcataaat actagacatc  11040
aaaacgtgaa atacttgcct ggcatcactc tacccgacaa tttggttgct aatccagact  11100
tgattgattc agtcaaggat gtcgacatca tcgttttcaa cattccacat caatttttgc  11160
```

```
cccgtatctg tagccaattg aaaggtcatg ttgattcaca cgtcagagct atctcctgtc  11220
taaagggttt tgaagttggt gctaaaggtg tccaattgct atcctcttac atcactgagg  11280
aactaggtat tcaatgtggt gctctatctg gtgctaacat tgccaccgaa gtcgctcaag  11340
aacactggtc tgaaacaaca gttgcttacc acattccaaa ggatttcaga ggcgagggca  11400
aggacgtcga ccataaggtt ctaaaggcct tgttccacag accttacttc cacgttagtg  11460
tcatcgaaga tgttgctggt atctccatct gtggtgcttt gaagaacgtt gttgccttag  11520
gttgtggttt cgtcgaaggt ctaggctggg gtaacaacgc ttctgctgcc atccaaagag  11580
tcggtttggg tgagatcatc agattcggtc aaatgttttt cccagaatct agagaagaaa  11640
catactacca agagtctgct ggtgttgctg atttgatcac cacctgcgct ggtggtagaa  11700
acgtcaaggt tgctaggcta atggctactt ctggtaagga cgcctgggaa tgtgaaaagg  11760
agttgttgaa tggccaatcc gctcaaggtt taattacctg caaagaagtt cacgaatggt  11820
tggaaacatg tggctctgtc gaagacttcc cattatttga agccgtatac caaatcgttt  11880
acaacaacta cccaatgaag aacctgccgg acatgattga agaattagat ctacatgaag  11940
attagattta ttggatccag gaaacagact agaattatgg gattgactac taaacctcta  12000
tctttgaaag ttaacgccgc tttgttcgac gtcgacggta ccattatcat ctctcaacca  12060
gccattgctg cattctggag ggatttcggt aaggacaaac cttatttcga tgctgaacac  12120
gttatccaag tctcgcatgg ttggagaacg tttgatgcca ttgctaagtt cgctccagac  12180
tttgccaatg aagagtatgt taacaaatta gaagctgaaa ttccggtcaa gtacggtgaa  12240
aaatccattg aagtcccagg tgcagttaag ctgtgcaacg ctttgaacgc tctaccaaaa  12300
gagaaatggg ctgtggcaac ttccggtacc cgtgatatgg cacaaaaatg gttcgagcat  12360
ctgggaatca ggagaccaaa gtacttcatt accgctaatg atgtcaaaca gggtaagcct  12420
catccagaac catatctgaa gggcaggaat ggcttaggat atccgatcaa tgagcaagac  12480
ccttccaaat ctaaggtagt agtatttgaa gacgctccag caggtattgc cgccggaaaa  12540
gccgccggtt gtaagatcat tggtattgcc actactttcg acttggactt cctaaaggaa  12600
aaaggctgtg acatcattgt caaaaaccac gaatccatca gagttggcgg ctacaatgcc  12660
gaaacagacg aagttgaatt catttttgac gactacttat atgctaagga cgatctgttg  12720
aaatggtaac ccgggctgca ggcatgcaag cttggctgtt ttggcggatg agagaagatt  12780
ttcagcctga tacagattaa atcagaacgc agaagcggtc tgataaaaca gaatttgcct  12840
ggcggcagta gcgcggtggt cccacctgac cccatgccga actcagaagt gaaacgccgt  12900
agcgccgatg gtagtgtggg gtctccccat gcgagagtag ggaactgcca ggcatcaaat  12960
aaaacgaaag gctcagtcga aagactgggc ctttcgtttt atctgttgtt tgtcggtgaa  13020
cgctctcctg agtaggacaa atccgccggg agcggatttg aacgttgcga agcaacggcc  13080
cggagggtgg cgggcaggac gcccgccata aactgccagg catcaaatta agcagaaggc  13140
catcctgacg gatggccttt ttgcgtttct acaaactcca gctggatcgg gcgctagagt  13200
atacatttaa atggtaccct ctagtcaagg ccttaagtga gtcgtattac ggactggccg  13260
tcgttttaca acgtcgtgac tgggaaaacc ctggcgttac ccaacttaat cgccttgcag  13320
cacatccccc tttcgccagc tggcgtaata gcgaagaggc ccgcaccgat cgcccttccc  13380
aacagttgcg cagcctgaat ggcgaatggc gcctgatgcg gtattttctc cttacgcatc  13440
tgtgcggtat ttcacaccgc atatggtgca ctctcagtac aatctgctct gatgccgcat  13500
```

agttaagcca gccccgacac ccgccaacac ccgctgacga gct 13543

<210> SEQ ID NO 48
<211> LENGTH: 13543
<212> TYPE: DNA
<213> ORGANISM: Artificial Sequence
<220> FEATURE:
<223> OTHER INFORMATION: Plasmid

<400> SEQUENCE: 48
tagtaaagcc ctcgctagat tttaatgcgg atgttgcgat tacttcgcca actattgcga 60
taacaagaaa aagccagcct ttcatgatat atctcccaat ttgtgtaggg cttattatgc 120
acgcttaaaa ataataaaag cagacttgac ctgatagttt ggctgtgagc aattatgtgc 180
ttagtgcatc taacgcttga gttaagccgc gccgcgaagc ggcgtcggct tgaacgaatt 240
gttagacatt atttgccgac taccttggtg atctcgcctt tcacgtagtg gacaaattct 300
tccaactgat ctgcgcgcga ggccaagcga tcttcttctt gtccaagata agcctgtcta 360
gcttcaagta tgacgggctg atactgggcc ggcaggcgct ccattgccca gtcggcagcg 420
acatccttcg gcgcgatttt gccggttact gcgctgtacc aaatgcggga caacgtaagc 480
actacatttc gctcatcgcc agcccagtcg ggcggcgagt tccatagcgt taaggtttca 540
tttagcgcct caaatagatc ctgttcagga accggatcaa agagttcctc cgccgctgga 600
cctaccaagg caacgctatg ttctcttgct tttgtcagca agatagccag atcaatgtcg 660
atcgtggctg gctcgaagat acctgcaaga atgtcattgc gctgccattc tccaaattgc 720
agttcgcgct tagctggata acgccacgga atgatgtcgt cgtgcacaac aatggtgact 780
tctacagcgc ggagaatctc gctctctcca ggggaagccg aagtttccaa aaggtcgttg 840
atcaaagctc gccgcgttgt ttcatcaagc cttacggtca ccgtaaccag caaatcaata 900
tcactgtgtg gcttcaggcc gccatccact gcggagccgt acaaatgtac ggccagcaac 960
gtcggttcga gatggcgctc gatgacgcca actacctctg atagttgagt cgatacttcg 1020
gcgatcaccg cttccctcat gatgtttaac tttgttttag ggcgactgcc ctgctgcgta 1080
acatcgttgc tgctccataa catcaaacat cgacccacgg cgtaacgcgc ttgctgcttg 1140
gatgcccgag gcatagactg taccccaaaa aaacagtcat aacaagccat gaaaaccgcc 1200
actgcgccgt taccaccgct gcgttcggtc aaggttctgg accagttgcg tgagcgcata 1260
cgctacttgc attacagctt acgaaccgaa caggcttatg tccactgggt tcgtgccttc 1320
atccgtttcc acggtgtgcg tcacccggca accttgggca gcagcgaagt cgaggcattt 1380
ctgtcctggc tggcgaacga gcgcaaggtt tcggtctcca cgcatcgtca ggcattggcg 1440
gccttgctgt tcttctacgg caaggtgctg tgcacggatc tgccctggct tcaggagatc 1500
ggaagacctc ggccgtcgcg gcgcttgccg gtggtgctga ccccggatga agtggttcgc 1560
atcctcggtt ttctggaagg cgagcatcgt ttgttcgccc agcttctgta tggaacgggc 1620
atgcggatca gtgagggttt gcaactgcgg gtcaaggatc tggatttcga tcacggcacg 1680
atcatcgtgc gggagggcaa gggctccaag gatcgggcct tgatgttacc cgagagcttg 1740
gcacccagcc tgcgcgagca ggggaattaa ttcccacggg ttttgctgcc cgcaaacggg 1800
ctgttctggt gttgctagtt tgttatcaga atcgcagatc cggcttcagc cggtttgccg 1860
gctgaaagcg ctatttcttc cagaattgcc atgatttttt ccccacggga ggcgtcactg 1920
gctcccgtgt tgtcggcagc tttgattcga taagcagcat cgcctgtttc aggctgtcta 1980
tgtgtgactg ttgagctgta acaagttgtc tcaggtgttc aatttcatgt tctagttgct 2040

```
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420
ttttttgttt atattcaagt ggttataatt tatagaataa agaaagaata aaaaaagata   3480
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
```

-continued cttatccagc ggatggacga ggccttcgtc tccagctgcg atatttccct gaataaagcc 4440
tggagcgcct gcagcctgaa gcaaggtacc catgaaatta cgtcagcggt ccagccagga 4500
caatctctgt acggtctgca gctaaccaac caacagcgaa ttattatttt tggcggcggc 4560
ctgccagtta tttttaatga gcaggtaatt ggcgccgtcg gcgttagcgg cggtacggtc 4620
gagcaggatc aattattagc ccagtgcgcc ctggattgtt tttccgcatt ataacctgaa 4680
gcgagaaggt atattatgag ctatcgtatg ttccgccagg cattctgagt gttaacgagg 4740
ggaccgtcat gtcgctttca ccgccaggcg tacgcctgtt ttacgatccg cgcgggcacc 4800
atgccggcgc catcaatgag ctgtgctggg ggctggagga gcagggggtc ccctgccaga 4860
ccataaccta tgacggaggc ggtgacgccg ctgcgctggg cgccctggcg gccagaagct 4920
cgcccctgcg ggtgggtatc gggctcagcg cgtccggcga gatagccctc actcatgccc 4980
agctgccggc ggacgcgccg ctggctaccg gacacgtcac cgatagcgac gatcaactgc 5040
gtacgctcgg cgccaacgcc gggcagctgg ttaaagtcct gccgttaagt gagagaaact 5100
gaatgtatcg tatctatacc cgcaccgggg ataaaggcac caccgccctg tacggcggca 5160
gccgcatcga gaaagaccat attcgcgtcg aggcctacgg caccgtcgat gaactgatat 5220
cccagctggg cgtctgctac gccacgaccc gcgacgccgg gctgcgggaa agcctgcacc 5280
atattcagca gacgctgttc gtgctggggg ctgaactggc cagcgatgcg cggggcctga 5340
cccgcctgag ccagacgatc ggcgaagagg agatcaccgc cctggagcgg cttatcgacc 5400
gcaatatggc cgagagcggc ccgttaaaac agttcgtgat cccggggagg aatctcgcct 5460
ctgcccagct gcacgtggcg cgcacccagt cccgtcggct cgaacgcctg ctgacggcca 5520
tggaccgcgc gcatccgctg cgcgacgcgc tcaaacgcta cagcaatcgc ctgtcggatg 5580
ccctgttctc catggcgcga atcgaagaga ctaggcctga tgcttgcgct tgaactggcc 5640
tagcaaacac agaaaaaagc ccgcacctga cagtgcgggc tttttttttc ctaggcgatc 5700
tgtgctgttt gccacggtat gcagcaccag cgcgagatta tgggctcgca cgctcgactg 5760
tcggacgggg gcactggaac gagaagtcag gcgagccgtc acgcccttga caatgccaca 5820
tcctgagcaa ataattcaac cactaaacaa atcaaccgcg tttcccggag gtaaccaagc 5880
ttcacctttt gagccgatga acaatgaaaa gatcaaaacg atttgcagta ctggcccagc 5940
gccccgtcaa tcaggacggg ctgattggcg agtggcctga agaggggctg atcgccatgg 6000
acagcccctt tgacccggtc tcttcagtaa aagtggacaa cggtctgatc gtcgaactgg 6060
acggcaaacg ccgggaccag tttgacatga tcgaccgatt tatcgccgat tacgcgatca 6120
acgttgagcg cacagagcag gcaatgcgcc tggaggcggt ggaaatagcc cgtatgctgg 6180
tggatattca cgtcagccgg gaggagatca ttgccatcac taccgccatc acgccggcca 6240
aagcggtcga ggtgatggcg cagatgaacg tggtggagat gatgatggcg ctgcagaaga 6300
tgcgtgcccg ccggaccccc tccaaccagt gccacgtcac caatctcaaa gataatccgg 6360
tgcagattgc cgctgacgcc gccgaggccg ggatccgcgg cttctcagaa caggagacca 6420
cggtcggtat cgcgcgctac gcgccgttta acgccctggc gctgttggtc ggttcgcagt 6480
gcggccgccc cggcgtgttg acgcagtgct cggtggaaga ggccaccgag ctggagctgg 6540
gcatgcgtgg cttaaccagc tacgccgaga cggtgtcggt ctacggcacc gaagcggtat 6600
ttaccgacgg cgatgatacg ccgtggtcaa aggcgttcct cgcctcggcc tacgcctccc 6660
gcgggttgaa aatgcgctac acctccggca ccggatccga agcgctgatg ggctattcgg 6720
agagcaagtc gatgctctac ctcgaatcgc gctgcatctt cattactaaa ggcgccgggg 6780

```
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttattttct ccggctacag cgcggtgccg aactacgaca   7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
```

-continued

```
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc tttttcttg  10500
tctagcgtgc accaatgctt ctggcgtcag gcagccatcg gaagctgtgg tatggctgtg  10560
caggtcgtaa atcactgcat aattcgtgtc gctcaaggcg cactcccgtt ctggataatg  10620
ttttttgcgc cgacatcata acggttctgg caaatattct gaaatgagct gttgacaatt  10680
aatcatccgg ctcgtataat gtgtggaatt gtgagcggat aacaatttca cacaggaaac  10740
agaccatgac tagtaaggag gacaattcca tggctgctgc tgctgataga ttaaacttaa  10800
cttccggcca cttgaatgct ggtagaaaga gaagttcctc ttctgtttct ttgaaggctg  10860
ccgaaaagcc tttcaaggtt actgtgattg gatctggtaa ctggggtact actattgcca  10920
aggtggttgc cgaaaattgt aagggatacc cagaagtttt cgctccaata gtacaaatgt  10980
gggtgttcga agaagagatc aatggtgaaa aattgactga aatcataaat actagacatc  11040
aaaacgtgaa atacttgcct ggcatcactc tacccgacaa tttggttgct aatccagact  11100
tgattgattc agtcaaggat gtcgacatca tcgttttcaa cattccacat caatttttgc  11160
cccgtatctg tagccaattg aaaggtcatg ttgattcaca cgtcagagct atctcctgtc  11220
taaagggttt tgaagttggt gctaaaggtg tccaattgct atcctcttac atcactgagg  11280
aactaggtat tcaatgtggt gctctatctg gtgctaacat tgccaccgaa gtcgctcaag  11340
aacactggtc tgaaacaaca gttgcttacc acattccaaa ggatttcaga ggcgagggca  11400
aggacgtcga ccataaggtt ctaaaggcct tgttccacag accttacttc cacgttagtg  11460
tcatcgaaga tgttgctggt atctccatct gtggtgcttt gaagaacgtt gttgccttag  11520
```

gttgtggttt cgtcgaaggt ctaggctggg gtaacaacgc ttctgctgcc atccaaagag 11580
tcggtttggg tgagatcatc agattcggtc aaatgttttt cccagaatct agagaagaaa 11640
catactacca agagtctgct ggtgttgctg atttgatcac cacctgcgct ggtggtagaa 11700
acgtcaaggt tgctaggcta atggctactt ctggtaagga cgcctgggaa tgtgaaaagg 11760
agttgttgaa tggccaatcc gctcaaggtt taattacctg caaagaagtt cacgaatggt 11820
tggaaacatg tggctctgtc gaagacttcc cattatttga agccgtatac caaatcgttt 11880
acaacaacta cccaatgaag aacctgccgg acatgattga agaattagat ctacatgaag 11940
attagattta ttggatccag gaaacagact agaattatgg gattgactac taaacctcta 12000
tctttgaaag ttaacgccgc tttgttcgac gtcgacggta ccattatcat ctctcaacca 12060
gccattgctg cattctggag ggatttcggt aaggacaaac cttatttcga tgctgaacac 12120
gttatccaag tctcgcatgg ttggagaacg tttgatgcca ttgctaagtt cgctccagac 12180
tttgccaatg aagagtatgt taacaaatta gaagctgaaa ttccggtcaa gtacggtgaa 12240
aaatccattg aagtcccagg tgcagttaag ctgtgcaacg ctttgaacgc tctaccaaaa 12300
gagaaatggg ctgtggcaac ttccggtacc cgtgatatgg cacaaaaatg gttcgagcat 12360
ctgggaatca ggagaccaaa gtacttcatt accgctaatg atgtcaaaca gggtaagcct 12420
catccagaac catatctgaa gggcaggaat ggcttaggat atccgatcaa tgagcaagac 12480
ccttccaaat ctaaggtagt agtatttgaa gacgctccag caggtattgc cgccggaaaa 12540
gccgccggtt gtaagatcat tggtattgcc actactttcg acttggactt cctaaaggaa 12600
aaaggctgtg acatcattgt caaaaaccac gaatccatca gagttggcgg ctacaatgcc 12660
gaaacagacg aagttgaatt catttttgac gactacttat atgctaagga cgatctgttg 12720
aaatggtaac ccgggctgca ggcatgcaag cttggctgtt ttggcggatg agagaagatt 12780
ttcagcctga tacagattaa atcagaacgc agaagcggtc tgataaaaca gaatttgcct 12840
ggcggcagta gcgcggtggt cccacctgac cccatgccga actcagaagt gaaacgccgt 12900
agcgccgatg gtagtgtggg gtctccccat gcgagagtag ggaactgcca ggcatcaaat 12960
aaaacgaaag gctcagtcga aagactgggc ctttcgtttt atctgttgtt tgtcggtgaa 13020
cgctctcctg agtaggacaa atccgccggg agcggatttg aacgttgcga agcaacggcc 13080
cggagggtgg cgggcaggac gcccgccata aactgccagg catcaaatta agcagaaggc 13140
catcctgacg gatggccttt ttgcgtttct acaaactcca gctggatcgg gcgctagagt 13200
atacatttaa atggtaccct ctagtcaagg ccttaagtga gtcgtattac ggactggccg 13260
tcgttttaca acgtcgtgac tgggaaaacc ctggcgttac ccaacttaat cgccttgcag 13320
cacatccccc tttcgccagc tggcgtaata gcgaagaggc ccgcaccgat cgcccttccc 13380
aacagttgcg cagcctgaat ggcgaatggc gcctgatgcg gtattttctc cttacgcatc 13440
tgtgcggtat ttcacaccgc atatggtgca ctctcagtac aatctgctct gatgccgcat 13500
agttaagcca gccccgacac ccgccaacac ccgctgacga gct 13543

<210> SEQ ID NO 49
<211> LENGTH: 13402
<212> TYPE: DNA
<213> ORGANISM: Artificial Sequence
<220> FEATURE:
<223> OTHER INFORMATION: Plamid

<400> SEQUENCE: 49

-continued

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
```

```
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420
tttttgtttt atattcaagt ggttataatt tatagaataa agaaagaata aaaaaagata   3480
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
```

-continued

```
ggaccgtcat gtcgctttca ccgccaggcg tacgcctgtt ttacgatccg cgcgggcacc   4800
atgccggcgc catcaatgag ctgtgctggg ggctggagga gcagggggtc ccctgccaga   4860
ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcaccctgat gcttgcgctt gaactggcct agcaaacaca gaaaaaagcc   5520
cgcacctgac agtgcgggct tttttttcc taggcgatct gtgctgtttg ccacggtatg   5580
cagcaccagc gcgagattat gggctcgcac gctcgactgt cggacggggg cactggaacg   5640
agaagtcagg cgagccgtca cgcccttgac aatgccacat cctgagcaaa taattcaacc   5700
actaaacaaa tcaaccgcgt ttcccggagg taaccaagct tcaccttttg agccgatgaa   5760
caatgaaaag atcaaaacga tttgcagtac tggcccagcg ccccgtcaat caggacgggc   5820
tgattggcga gtggcctgaa gaggggctga tcgccatgga cagccccttt gacccggtct   5880
cttcagtaaa agtggacaac ggtctgatcg tcgaactgga cggcaaacgc cgggaccagt   5940
ttgacatgat cgaccgattt atcgccgatt acgcgatcaa cgttgagcgc acagagcagg   6000
caatgcgcct ggaggcggtg gaaatagccc gtatgctggt ggatattcac gtcagccggg   6060
aggagatcat tgccatcact accgccatca cgccggccaa agcggtcgag gtgatggcgc   6120
agatgaacgt ggtggagatg atgatggcgc tgcagaagat gcgtgcccgc cggacccccct   6180
ccaaccagtg ccacgtcacc aatctcaaag ataatccggt gcagattgcc gctgacgccg   6240
ccgaggccgg gatccgcggc ttctcagaac aggagaccac ggtcggtatc gcgcgctacg   6300
cgccgtttaa cgccctggcg ctgttggtcg gttcgcagtg cggccgcccc ggcgtgttga   6360
cgcagtgctc ggtggaagag gccaccgagc tggagctggg catgcgtggc ttaaccagct   6420
acgccgagac ggtgtcggtc tacggcaccg aagcggtatt taccgacggc gatgatacgc   6480
cgtggtcaaa ggcgttcctc gcctcggcct acgcctcccg cgggttgaaa atgcgctaca   6540
cctccggcac cggatccgaa gcgctgatgg gctattcgga gagcaagtcg atgctctacc   6600
tcgaatcgcg ctgcatcttc attactaaag gcgccggggt tcagggactg caaaacggcg   6660
cggtgagctg tatcggcatg accggcgctg tgccgtcggg cattcgggcg gtgctggcgg   6720
aaaacctgat cgcctctatg ctcgacctcg aagtggcgtc cgccaacgac cagactttct   6780
cccactcgga tattcgccgc accgcgcgca ccctgatgca gatgctgccg ggcaccgact   6840
ttattttctc cggctacagc gcggtgccga actacgacaa catgttcgcc ggctcgaact   6900
tcgatgcgga agattttgat gattacaaca tcctgcagcg tgacctgatg gttgacggcg   6960
gcctgcgtcc ggtgaccgag gcggaaacca ttgccattcg ccagaaagcg gcgcgggcga   7020
tccaggcggt tttccgcgag ctggggctgc cgccaatcgc cgacgaggag gtggaggccg   7080
ccacctacgc gcacggcagc aacgagatgc cgccgcgtaa cgtggtggag gatctgagtg   7140
```

```
cggtggaaga gatgatgaag cgcaacatca ccggcctcga tattgtcggc gcgctgagcc   7200
gcagcggctt tgaggatatc gccagcaata ttctcaatat gctgcgccag cgggtcaccg   7260
gcgattacct gcagacctcg gccattctcg atcggcagtt cgaggtggtg agtgcggtca   7320
acgacatcaa tgactatcag gggccgggca ccggctatcg catctctgcc gaacgctggg   7380
cggagatcaa aaatattccg ggcgtggttc agcccgacac cattgaataa ggcggtattc   7440
ctgtgcaaca gacaacccaa attcagccct cttttaccct gaaaacccgc gagggcgggg   7500
tagcttctgc cgatgaacgc gccgatgaag tggtgatcgg cgtcggccct gccttcgata   7560
aacaccagca tcacactctg atcgatatgc cccatggcgc gatcctcaaa gagctgattg   7620
ccggggtgga agaagagggg cttcacgccc gggtggtgcg cattctgcgc acgtccgacg   7680
tctcctttat ggcctgggat gcggccaacc tgagcggctc ggggatcggc atcggtatcc   7740
agtcgaaggg gaccacggtc atccatcagc gcgatctgct gccgctcagc aacctggagc   7800
tgttctccca ggcgccgctg ctgacgctgg agacctaccg gcagattggc aaaaacgctg   7860
cgcgctatgc gcgcaaagag tcaccttcgc cggtgccggt ggtgaacgat cagatggtgc   7920
ggccgaaatt tatggccaaa gccgcgctat ttcatatcaa agagaccaaa catgtggtgc   7980
aggacgccga gcccgtcacc ctgcacatcg acttagtaag ggagtgacca tgagcgagaa   8040
aaccatgcgc gtgcaggatt atccgttagc cacccgctgc ccggagcata tcctgacgcc   8100
taccggcaaa ccattgaccg atattaccct cgagaaggtg ctctctggcg aggtgggccc   8160
gcaggatgtg cggatctccc gccagaccct tgagtaccag gcgcagattg ccgagcagat   8220
gcagcgccat gcggtggcgc gcaatttccg ccgcgcggcg gagcttatcg ccattcctga   8280
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggg acgcgggaca atatcgccgg gaccctcgcc gcgctggagc aggccctggc   8640
gaaaacaccg tggtcgatga gcgatgtctc tcgcatctat cttaacgaag ccgcgccggt   8700
gattggcgat gtggcgatgg agaccatcac cgagaccatt atcaccgaat cgaccatgat   8760
cggtcataac ccgcagacgc cgggcggggt gggcgttggc gtggggacga ctatcgccct   8820
cgggcggctg gcgacgctgc cggcggcgca gtatgccgag ggtggatcg tactgattga   8880
cgacgccgtc gatttccttg acgccgtgtg gtggctcaat gaggcgctcg accgggggat   8940
caacgtggtg gcggcgatcc tcaaaaagga cgacggcgtg ctggtgaaca accgcctgcg   9000
taaaaccctg ccggtggtgg atgaagtgac gctgctggag caggtccccg agggggtaat   9060
ggcggcggtg gaagtggccg cgccgggcca ggtggtgcgg atcctgtcga atccctacgg   9120
gatcgccacc ttcttcgggc taagcccgga agagacccag gccatcgtcc ccatcgcccg   9180
cgccctgatt ggcaaccgtt ccgcggtggt gctcaagacc ccgcaggggg atgtgcagtc   9240
gcgggtgatc ccggcgggca acctctacat tagcggcgaa aagcgccgcg gagaggccga   9300
tgtcgccgag ggcgcggaag ccatcatgca ggcgatgagc gcctgcgctc cggtacgcga   9360
catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
```

-continued

```
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta aacgggcgct cgcgccagcc tctaggtaca  10320
aataaaaaag gcacgtcaga tgacgtgcct tttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt tttttgcgcc gacatcataa  10500
cggttctggc aaatattctg aaatgagctg ttgacaatta atcatccggc tcgtataatg  10560
tgtggaattg tgagcggata acaatttcac acaggaaaca gaccatgact agtaaggagg  10620
acaattccat ggctgctgct gctgatagat taaacttaac ttccggccac ttgaatgctg  10680
gtagaaagag aagttcctct tctgtttctt tgaaggctgc cgaaaagcct ttcaaggtta  10740
ctgtgattgg atctggtaac tggggtacta ctattgccaa ggtggttgcc gaaaattgta  10800
agggataccc agaagttttc gctccaatag tacaaatgtg ggtgttcgaa gaagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgttttcaac attccacatc aatttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
tctccatctg tggtgctttg aagaacgttg ttgccttagg ttgtggtttc gtcgaaggtc  11400
taggctgggg taacaacgct tctgctgcca tccaaagagt cggtttgggt gagatcatca  11460
gattcggtca aatgtttttc ccagaatcta gagaagaaac atactaccaa gagtctgctg  11520
gtgttgctga tttgatcacc acctgcgctg gtggtagaaa cgtcaaggtt gctaggctaa  11580
tggctacttc tggtaaggac gcctgggaat gtgaaaagga gttgttgaat ggccaatccg  11640
ctcaaggttt aattacctgc aaagaagttc acgaatggtt ggaaacatgt ggctctgtcg  11700
aagacttccc attatttgaa gccgtatacc aaatcgttta caacaactac ccaatgaaga  11760
acctgccgga catgattgaa gaattagatc tacatgaaga ttagatttat tggatccagg  11820
aaacagacta gaattatggg attgactact aaacctctat ctttgaaagt taacgccgct  11880
```

ttgttcgacg tcgacggtac cattatcatc tctcaaccag ccattgctgc attctggagg 11940
gatttcggta aggacaaacc ttatttcgat gctgaacacg ttatccaagt ctcgcatggt 12000
tggagaacgt ttgatgccat tgctaagttc gctccagact ttgccaatga agagtatgtt 12060
aacaaattag aagctgaaat tccggtcaag tacggtgaaa aatccattga agtcccaggt 12120
gcagttaagc tgtgcaacgc tttgaacgct ctaccaaaag agaaatgggc tgtggcaact 12180
tccggtaccc gtgatatggc acaaaaatgg ttcgagcatc tgggaatcag gagaccaaag 12240
tacttcatta ccgctaatga tgtcaaacag ggtaagcctc atccagaacc atatctgaag 12300
ggcaggaatg gcttaggata tccgatcaat gagcaagacc cttccaaatc taaggtagta 12360
gtatttgaag acgctccagc aggtattgcc gccggaaaag ccgccggttg taagatcatt 12420
ggtattgcca ctactttcga cttggacttc ctaaaggaaa aaggctgtga catcattgtc 12480
aaaaaccacg aatccatcag agttggcggc tacaatgccg aaacagacga agttgaattc 12540
atttttgacg actacttata tgctaaggac gatctgttga aatggtaacc cgggctgcag 12600
gcatgcaagc ttggctgttt tggcggatga gagaagattt tcagcctgat acagattaaa 12660
tcagaacgca gaagcggtct gataaaacag aatttgcctg gcggcagtag cgcggtggtc 12720
ccacctgacc ccatgccgaa ctcagaagtg aaacgccgta gcgccgatgg tagtgtgggg 12780
tctccccatg cgagagtagg gaactgccag gcatcaaata aaacgaaagg ctcagtcgaa 12840
agactgggcc tttcgtttta tctgttgttt gtcggtgaac gctctcctga gtaggacaaa 12900
tccgccggga gcggatttga acgttgcgaa gcaacggccc ggagggtggc gggcaggacg 12960
cccgccataa actgccaggc atcaaattaa gcagaaggcc atcctgacgg atggcctttt 13020
tgcgtttcta caaactccag ctggatcggg cgctagagta tacatttaaa tggtaccctc 13080
tagtcaaggc cttaagtgag tcgtattacg gactggccgt cgttttacaa cgtcgtgact 13140
gggaaaaccc tggcgttacc caacttaatc gccttgcagc acatccccct ttcgccagct 13200
ggcgtaatag cgaagaggcc cgcaccgatc gcccttccca acagttgcgc agcctgaatg 13260
gcgaatggcg cctgatgcgg tattttctcc ttacgcatct gtgcggtatt tcacaccgca 13320
tatggtgcac tctcagtaca atctgctctg atgccgcata gttaagccag ccccgacacc 13380
cgccaacacc cgctgacgag ct 13402

<210> SEQ ID NO 50
<211> LENGTH: 14443
<212> TYPE: DNA
<213> ORGANISM: Artificial Sequence
<220> FEATURE:
<223> OTHER INFORMATION: Plasmid

<400> SEQUENCE: 50
ttctgataac aaactagcaa caccagaaca gcccgtttgc gggcagcaaa acccgtggga 60
attaattccc ctgctcgcgc aggctgggtg ccaagctctc gggtaacatc aaggcccgat 120
ccttggagcc cttcttacag agatgaaaaa caaaccgcga cgccaggcgg catcgcggtc 180
tcagagatat gtttacgtag atcgaagagc accggtgttt aaacgccctt gacgatgcca 240
catcctgagc aaataattca accactaaac aaatcaaccg cgtttcccgg aggtaaccga 300
gctcatgatc ctgtgttgtg gtgaagccct gatcgacatg ctgccccggc agacgacgct 360
gggtgaggcg ggctttgccc cttacgcagg cggagcggtc ttcaacacgg caattgcgct 420
ggggcgtctt ggcgtccctt cagccttttt taccggtctt tccgacgaca tgatgggcga 480

-continued

```
tatcctgcgg gagaccctgc gggccagcaa ggtggatttc agctattgcg ccaccctgtc    540
gcgccccacc accattgcgt tcgttaagct ggttgatggc catgcgacct acgcttttta    600
cgacgagaac accgccggcc ggatgatcac cgaggccgaa cttccggcct tgggagcgga    660
ttgcgaagcg ctgcatttcg gcgccatcag ccttattccc gaaccctgcg gcagcaccta    720
tgaggcgctg atgacgcgcg agcatgagac ccgcgtcatc tcgctcgatc cgaacattcg    780
tcccggcttc atccagaaca agcagtcgca catggcccgc atccgccgca tggcggcgat    840
gtctgacatc gtcaagttct cggatgagga cctggcgtgg ttcggtctgg aaggcgacga    900
ggacacgctt gcccgccact ggctgcacca cggtgcaaaa ctcgtcgttg tcacccgtgg    960
cgccaagggt gccgtgggtt acagcgccaa tctcaaggtg gaagtggcct ccgagcgcgt   1020
cgaagtggtc gatacggtcg gcgccggcga tacgttcgat gccggcattc ttgcttcgct   1080
gaaaatgcag ggcctgctga ccaaagcgca ggtggcttcg ctgagcgaag agcagatcag   1140
aaaagctttg gcgcttggcg cgaaagccgc tgcggtcact gtctcgcggg ctggcgcaaa   1200
tccgcctttc gcgcatgaaa tcggtttgtg attaattaaa gcacgcagtc aaacaaaaaa   1260
cccgcgccat tgcgcgggtt tttttatgcc cgaaggcgcg ccagcacgca gtcaaacaaa   1320
aaacccgcgc cattgcgcgg gtttttttat gcccgaacgg ccgaggtctt ccgatctcct   1380
gaagccaggg cagatccgtg cacagcacct tgccgtagaa gaacagcaag gccgccaatg   1440
cctgacgatg cgtggagacc gaaaccttgc gctcgttcgc cagccaggac agaaatgcct   1500
cgacttcgct gctgcccaag gttgccgggt gacgcacacc gtggaaacgg atgaaggcac   1560
gaacccagtg gacataagcc tgttcggttc gtaagctgta atgcaagtag cgtatgcgct   1620
cacgcaactg gtccagaacc ttgaccgaac gcagcggtgg taacggcgca gtggcggttt   1680
tcatggcttg ttatgactgt ttttttgggg tacagtctat gcctcgggca tccaagcagc   1740
aagcgcgtta cgccgtgggt cgatgtttga tgttatggag cagcaacgat gttacgcagc   1800
agggcagtcg ccctaaaaca aagttaaaca tcatgaggga agcggtgatc gccgaagtat   1860
cgactcaact atcagaggta gttggcgtca tcgagcgcca tctcgaaccg acgttgctgg   1920
ccgtacattt gtacggctcc gcagtggatg gcggcctgaa gccacacagt gatattgatt   1980
tgctggttac ggtgaccgta aggcttgatg aaacaacgcg gcgagctttg atcaacgacc   2040
ttttggaaac ttcggcttcc cctggagaga gcgagattct ccgcgctgta gaagtcacca   2100
ttgttgtgca cgacgacatc attccgtggc gttatccagc taagcgcgaa ctgcaatttg   2160
gagaatggca gcgcaatgac attcttgcag gtatcttcga gccagccacg atcgacattg   2220
atctggctat cttgctgaca aaagcaagag aacatagcgt tgccttggta ggtccagcgg   2280
cggaggaact ctttgatccg gttcctgaac aggatctatt tgaggcgcta aatgaaacct   2340
taacgctatg gaactcgccg cccgactggg ctggcgatga gcgaaatgta gtgcttacgt   2400
tgtcccgcat ttggtacagc gcagtaaccg gcaaaatcgc gccgaaggat gtcgctgccg   2460
actgggcaat ggagcgcctg ccggcccagt atcagcccgt catacttgaa gctagacagg   2520
cttatcttgg acaagaagaa gatcgcttgg cctcgcgcgc agatcagttg gaagaatttg   2580
tccactacgt gaaaggcgag atcaccaagg tagtcggcaa ataatgtcta acaattcgtt   2640
caagccgacg ccgcttcgcg gcgcggctta actcaagcgt tagatgcact aagcacataa   2700
ttgctcacag ccaaactatc aggtcaagtc tgcttttatt atttttaagc gtgcataata   2760
agccctacac aaattgggag atatatcatg aaaggctggc tttttcttgt tatcgcaata   2820
gttggcgaag taatcgcaac atccgcatta aaatctagcg agggctttac taagctcgtc   2880
```

agcgggtgtt ggcgggtgtc ggggctggct taactatgcg gcatcagagc agattgtact 2940
gagagtgcac catatgcggt gtgaaatacc gcacagatgc gtaaggagaa aataccgcat 3000
caggcgccat tcgccattca ggctgcgcaa ctgttgggaa gggcgatcgg tgcgggcctc 3060
ttcgctatta cgccagctgg cgaaaggggg atgtgctgca aggcgattaa gttgggtaac 3120
gccagggttt tcccagtcac gacgttgtaa aacgacggcc agtccgtaat acgactcact 3180
taaggccttg actagagggt accatttaaa tgtatactct agcgcccgat ccagctggag 3240
tttgtagaaa cgcaaaaagg ccatccgtca ggatggcctt ctgcttaatt tgatgcctgg 3300
cagtttatgg cgggcgtcct gcccgccacc ctccgggccg ttgcttcgca acgttcaaat 3360
ccgctcccgg cggatttgtc ctactcagga gagcgttcac cgacaaacaa cagataaaac 3420
gaaaggccca gtctttcgac tgagcctttc gttttatttg atgcctggca gttccctact 3480
ctcgcatggg gagaccccac actaccatcg gcgctacggc gtttcacttc tgagttcggc 3540
atggggtcag gtgggaccac cgcgctactg ccgccaggca aattctgttt tatcagaccg 3600
cttctgcgtt ctgatttaat ctgtatcagg ctgaaaatct tctctcatcc gccaaaacag 3660
ccaagcttgc atgcctgcag cccgggttac catttcaaca gatcgtcctt agcatataag 3720
tagtcgtcaa aaatgaattc aacttcgtct gtttcggcat tgtagccgcc aactctgatg 3780
gattcgtggt tttgacaat gatgtcacag cctttttcct ttaggaagtc caagtcgaaa 3840
gtagtggcaa taccaatgat cttacaaccg gcggcttttc cggcggcaat acctgctgga 3900
gcgtcttcaa atactactac cttagatttg gaagggtctt gctcattgat cggatatcct 3960
aagccattcc tgcccttcag atatggttct ggatgaggct taccctgttt gacatcatta 4020
gcggtaatga agtactttgg tctcctgatt cccagatgct cgaaccattt ttgtgccata 4080
tcacgggtac cggaagttgc cacagcccat ttctcttttg gtagagcgtt caaagcgttg 4140
cacagcttaa ctgcacctgg gacttcaatg gatttttcac cgtacttgac cggaatttca 4200
gcttctaatt tgttaacata ctcttcattg gcaaagtctg gagcgaactt agcaatggca 4260
tcaaacgttc tccaaccatg cgagacttgg ataacgtgtt cagcatcgaa ataaggtttg 4320
tccttaccga aatccctcca gaatgcagca atggctggtt gagagatgat aatggtaccg 4380
tcgacgtcga acaaagcggc gttaactttc aaagatagag gtttagtagt caatcccata 4440
attctagtct gtttcctgga tccaataaat ctaatcttca tgtagatcta attcttcaat 4500
catgtccggc aggttcttca ttgggtagtt gttgtaaacg atttggtata cggcttcaaa 4560
taatgggaag tcttcgacag agccacatgt ttccaaccat tcgtgaactt ctttgcaggt 4620
aattaaacct tgagcggatt ggccattcaa caactccttt tcacattccc aggcgtcctt 4680
accagaagta gccattagcc tagcaacctt gacgtttcta ccaccagcgc aggtggtgat 4740
caaatcagca acaccagcag actcttggta gtatgtttct tctctagatt ctgggaaaaa 4800
catttgaccg aatctgatga tctcacccaa accgactctt tggatggcag cagaagcgtt 4860
gttaccccag cctagacctt cgacgaaacc acaacctaag gcaacaacgt tcttcaaagc 4920
accacagatg gagataccag caacatcttc gatgacacta acgtggaagt aaggtctgtg 4980
gaacaaggcc tttagaacct tatggtcgac gtccttgccc tcgcctctga aatcctttgg 5040
aatgtggtaa gcaactgttg tttcagacca gtgttcttga gcgacttcgg tggcaatgtt 5100
agcaccagat agagcaccac attgaatacc tagttcctca gtgatgtaag aggatagcaa 5160
ttggacacct ttagcaccaa cttcaaaacc ctttagacag gagatagctc tgacgtgtga 5220

-continued

```
atcaacatga cctttcaatt ggctacagat acggggcaaa aattgatgtg gaatgttgaa   5280
aacgatgatg tcgacatcct tgactgaatc aatcaagtct ggattagcaa ccaaattgtc   5340
gggtagagtg atgccaggca agtatttcac gttttgatgt ctagtattta tgatttcagt   5400
caatttttca ccattgatct cttcttcgaa cacccacatt tgtactattg gagcgaaaac   5460
ttctgggtat cccttacaat tttcggcaac caccttggca atagtagtac cccagttacc   5520
agatccaatc acagtaacct tgaaaggctt ttcggcagcc ttcaaagaaa cagaagagga   5580
acttctcttt ctaccagcat tcaagtggcc ggaagttaag tttaatctat cagcagcagc   5640
agccatggaa ttgtcctcct tactagtcat ggtctgtttc ctgtgtgaaa ttgttatccg   5700
ctcacaattc cacacattat acgagccgga tgattaattg tcaacagctc atttcagaat   5760
atttgccaga accgttatga tgtcggcgca aaaaacatta tccagaacgg gagtgcgcct   5820
tgagcgacac gaattatgca gtgatttacg acctgcacag ccataccaca gcttccgatg   5880
gctgcctgac gccagaagca ttggtgcacg ctagacaaga aaaaaggcac gtcatctgac   5940
gtgccttttt tatttgtacc tagaggctgg cgcgagcgcc cgtttaattc gcctgaccgg   6000
ccagtagcag cccggtggcg accgcattgc gcggcccttc tgttccccga atattgccct   6060
gcccggcgac cacgccatag tgcgacaagg cttccgtgat aagctgcggg atctcaaagt   6120
ccagcgatga gccgcccacc agcaccacaa aggcgatatc gcgaatggaa ccgccgggtg   6180
agacctggcg cagcgcgcgc aggcagttgg tgacaaacac tttctctttc gcctgccggc   6240
gcacgagacg aatttttttcc agcgggctgg cgttatcgat cggcaccagt tcgccctcct   6300
tgatgtacac cactttggcg aacaccgccg ggctgagggc ttcccgaaag aactccaccg   6360
cgccattctc gtgacgaata ctgaacaggc tttccacttt ggccagcggg tattttttta   6420
tcgcttccgc cagcgaaaga tcctcgaggc ccagctcggt tttaatcaac aggctgacca   6480
tattccccgc cccggcgaga tggaccgccg ttatctgccc ctccgcgttg acgatcgccg   6540
catccgtcga gccggcgccg aggtcgagga tcgccagcgg cgccgcacag ccgggagtgg   6600
ttaacgcccc ggcgatggcc atgttggcct ccacgccgcc caccaccacc tcggtctgca   6660
gtcgggcgct cagttcgcgg gcgataacct gcatttgcag acgatccgct ttcaccatcg   6720
ccgccatccc gacggcattc tccatggcgc actcgccggc catcccgccc tgcaccttgc   6780
gcggaataaa cgtatccacc gccagcagat cctggatgta tatcgcgctc atctcatggc   6840
cggtcaggga cgccattacc ttgcgcaccc gctcaagcat gccgccggcg tgggtgcccg   6900
gttcgccgcg gatgtcgcgt accggagcgc aggcgctcat cgcctgcatg atggcttccg   6960
cgccctcggc gacatcggcc tctccgcggc gcttttcgcc gctaatgtag aggttgcccg   7020
ccgggatcac ccgcgactgc acatccccct gcggggtctt gagcaccacc gcggaacggt   7080
tgccaatcag ggcgcgggcg atggggacga tggcctgggt ctcttccggg cttagcccga   7140
agaaggtggc gatcccgtag ggattcgaca ggatccgcac cacctggccc ggcgcggcca   7200
cttccaccgc cgccattacc ccctcgggga cctgctccag cagcgtcact tcatccacca   7260
ccggcagggt tttacgcagg cggttgttca ccagcacgcc gtcgtccttt ttgaggatcg   7320
ccgccaccac gttgatcccc cggtcgagcg cctcattgag ccaccacacg gcgtcaagga   7380
aatcgacggc gtcgtcaatc agtacgatcc accccctcggc atactgcgcc gccggcagcg   7440
tcgccagccg cccgagggcg atagtcgtcc ccacgccaac gcccaccccg cccggcgtct   7500
gcgggttatg accgatcatg gtcgattcgg tgataatggt ctcggtgatg gtctccatcg   7560
ccacatcgcc aatcaccggc gcggcttcgt taagatagat gcgagagaca tcgctcatcg   7620
```

```
accacggtgt tttcgccagg gcctgctcca gcgcggcgag ggtcccggcg atattgtccc   7680
gcgtcccttt catgcccgtc gtcgcgacga tcccgctggc aacaaacgcc ctcgcctgcg   7740
ggtagtcgga cgccagcgcc acctcggtgg tggcgttgcc gatatcaatc ccggctatta   7800
acggcatgct gacctccgct tagcttcctt tacgcagctt atgccgctgc tgatacactt   7860
ccgccgactc ccggacaaag gcggcattca ctgtcgcatg ccaggtgtgc tccagctcgt   7920
cggcgatcgc cagcagctcc gcctgcgagg agcggaacgg gcgcagcgcg ttatagatag   7980
ccagaatgcg ctcgtcagga atggcgataa gctccgccgc gcggcggaaa ttgcgcgcca   8040
ccgcatggcg ctgcatctgc tcggcaatct gcgcctggta ctcaagggtc tggcgggaga   8100
tccgcacatc ctgcgggccc acctcgccag agagcacctt ctcgagggta atatcggtca   8160
atggtttgcc ggtaggcgtc aggatatgct ccgggcagcg ggtggctaac ggataatcct   8220
gcacgcgcat ggttttctcg ctcatggtca ctcccttact aagtcgatgt gcagggtgac   8280
gggctcggcg tcctgcacca catgtttggt ctctttgata tgaaatagcg cggctttggc   8340
cataaatttc ggccgcacca tctgatcgtt caccaccggc accggcgaag gtgactcttt   8400
gcgcgcatag cgcgcagcgt ttttgccaat ctgccggtag gtctccagcg tcagcagcgg   8460
cgcctgggag aacagctcca ggttgctgag cggcagcaga tcgcgctgat ggatgaccgt   8520
ggtccccttc gactggatac cgatgccgat ccccgagccg ctcaggttgg ccgcatccca   8580
ggccataaag gagacgtcgg acgtgcgcag aatgcgcacc acccgggcgt gaagcccctc   8640
ttcttccacc ccggcaatca gctctttgag gatcgcgcca tggggcatat cgatcagagt   8700
gtgatgctgg tgtttatcga aggcagggcc gacgccgatc accacttcat cggcgcgttc   8760
atcggcagaa gctaccccgc cctcgcgggt tttcagggta aaagagggct gaatttgggt   8820
tgtctgttgc acaggaatac cgccttgttc aatggtgtcg ggctgaacca cgcccggaat   8880
atttttgatc tccgcccagc gttcggcaga gatgcgatag ccggtgcccg gcccctgata   8940
gtcattgatg tcgttgaccg cactcaccac ctcgaactgc cgatcgaaaa tggccgaggt   9000
ctgcaggtaa tcgccggtga cccgctggcg cagcatattg agaatattgc tggcgatatc   9060
ctcaaagccg ctgcggctca gcgcgccgac aatatcgagg ccggtgatgt tgcgcttcat   9120
catctcttcc accgcactca gatcctccac cacgttacgc ggcggcatct cgttgctgcc   9180
gtgcgcgtag gtggcggcct ccacctcctc gtcggcgatt ggcggcagcc ccagctcgcg   9240
gaaaaccgcc tggatcgccc gcgccgcttt ctggcgaatg gcaatggttt ccgcctcggt   9300
caccggacgc aggccgccgt caaccatcag gtcacgctgc aggatgttgt aatcatcaaa   9360
atcttccgca tcgaagttcg agccggcgaa catgttgtcg tagttcggca ccgcgctgta   9420
gccggagaaa ataaagtcgg tgcccggcag catctgcatc agggtgcgcg cggtgcggcg   9480
aatatccgag tgggagaaag tctggtcgtt ggcggacgcc acttcgaggt cgagcataga   9540
ggcgatcagg ttttccgcca gcaccgcccg aatgcccgac ggcacagcgc cggtcatgcc   9600
gatacagctc accgcgccgt tttgcagtcc ctgaaccccg gcgcctttag taatgaagat   9660
gcagcgcgat tcgaggtaga gcatcgactt gctctccgaa tagcccatca gcgcttcgga   9720
tccggtgccg gaggtgtagc gcattttcaa cccgcgggag gcgtaggccg aggcgaggaa   9780
cgcctttgac cacggcgtat catcgccgtc ggtaaatacc gcttcggtgc cgtagaccga   9840
caccgtctcg gcgtagctgg ttaagccacg catgcccagc tccagctcgg tggcctcttc   9900
caccgagcac tgcgtcaaca cgccggggcg gccgcactgc gaaccgacca acagcgccag   9960
```

-continued

```
ggcgttaaac ggcgcgtagc gcgcgatacc gaccgtggtc tcctgttctg agaagccgcg  10020
gatcccggcc tcggcggcgt cagcggcaat ctgcaccgga ttatctttga gattggtgac  10080
gtggcactgg ttggaggggg tccggcgggc acgcatcttc tgcagcgcca tcatcatctc  10140
caccacgttc atctgcgcca tcacctcgac cgctttggcc ggcgtgatgg cggtagtgat  10200
ggcaatgatc tcctcccggc tgacgtgaat atccaccagc atacgggcta tttccaccgc  10260
ctccaggcgc attgcctgct ctgtgcgctc aacgttgatc gcgtaatcgg cgataaatcg  10320
gtcgatcatg tcaaactggt cccggcgttt gccgtccagt tcgacgatca gaccgttgtc  10380
cacttttact gaagagaccg ggtcaaaggg gctgtccatg gcgatcagcc cctcttcagg  10440
ccactcgcca atcagcccgt cctgattgac ggggcgctgg gccagtactg caaatcgttt  10500
tgatcttttc attgttcatc ggctcaaaag gtgaagcttg gttacctccg ggaaacgcgg  10560
ttgatttgtt tagtggttga attatttgct caggatgtgg cattgtcaag ggcgtgacgg  10620
ctcgcctgac ttctcgttcc agtgcccccg tccgacagtc gagcgtgcga gcccataatc  10680
tcgcgctggt gctgcatacc gtggcaaaca gcacagatcg cctaggaaaa aaaaagcccg  10740
cactgtcagg tgcgggcttt tttctgtgtt tgctaggcca gttcaagcgc aagcatcagg  10800
gtgcagctgg gcagaggcga gattcctccc cgggatcacg aactgtttta acgggccgct  10860
ctcggccata ttgcggtcga taagccgctc cagggcggtg atctcctctt cgccgatcgt  10920
ctggctcagg cgggtcaggc cccgcgcatc gctggccagt tcagccccca gcacgaacag  10980
cgtctgctga atatggtgca ggctttcccg cagcccggcg tcgcgggtcg tggcgtagca  11040
gacgcccagc tgggatatca gttcatcgac ggtgccgtag gcctcgacgc gaatatggtc  11100
tttctcgatg cggctgccgc cgtacagggc ggtggtgcct ttatccccgg tgcgggtata  11160
gatacgatac attcagtttc tctcacttaa cggcaggact ttaaccagct gcccggcgtt  11220
ggcgccgagc gtacgcagtt gatcgtcgct atcggtgacg tgtccggtag ccagcggcgc  11280
gtccgccggc agctgggcat gagtgagggc tatctcgccg gacgcgctga gcccgatacc  11340
cacccgcagg ggcgagcttc tggccgccag ggcgcccagc gcagcggcgt caccgcctcc  11400
gtcataggtt atggtctggc aggggacccc ctgctcctcc agcccccagc acagctcatt  11460
gatggcgccg gcatggtgcc cgcgcggatc gtaaaacagg cgtacgcctg gcggtgaaag  11520
cgacatgacg gtcccctcgt taacactcag aatgcctggc ggaacatacg atagctcata  11580
atataccttc tcgcttcagg ttataatgcg gaaaaacaat ccagggcgca ctgggctaat  11640
aattgatcct gctcgaccgt accgccgcta acgccgacgg cgccaattac ctgctcatta  11700
aaaataactg gcaggccgcc gccaaaaata ataattcgct gttggttggt tagctgcaga  11760
ccgtacagag attgtcctgg ctggaccgct gacgtaattt catgggtacc ttgcttcagg  11820
ctgcaggcgc tccaggcttt attcagggaa atatcgcagc tggagacgaa ggcctcgtcc  11880
atccgctgga taagcagcgt gttgcctccg cggtcaacta cggaaaacac caccgccacg  11940
ttgatctcag tggctttttt ttccaccgcc gccgccattt gctgggcggc ggccagggtg  12000
attgtctgaa cttgttggct cttgttcatc attctctccc gcaagcttgg ttacctccgg  12060
gaaacgcggt tgatttgttt agtggttgaa ttatttgctc aggatgtggc attgtcaagg  12120
gcgtgacggc tcgcctgact tctcgttcca gtgcccccgt ccgacagtcg agcgtgcgag  12180
cccataatct cgcgctggtg ctgcataccg tggcaaacag cacagatcgc ctagcagtca  12240
aaagcctccg gtcggaggct tttgactatt taaatgaatt cccgacagta agacgggtaa  12300
gcctgttgat gataccgctg ccttactggg tgcattagcc agtctgaatg acctgtcacg  12360
```

```
ggataatccg aagtggtcag actggaaaat cagagggcag gaactgctga acagcaaaaa  12420
gtcagatagc accacatagc agacccgcca taaaacgccc tgagaagccc gtgacgggct  12480
tttcttgtat tatgggtagt ttccttgcat gaatccataa aaggcgcctg tagtgccatt  12540
tacccccatt cactgccaga gccgtgagcg cagcgaactg aatgtcacga aaaagacagc  12600
gactcaggtg cctgatggtc ggagacaaaa ggaatattca gcgatttgcc cgagcttgcg  12660
agggtgctac ttaagccttt agggttttaa ggtctgtttt gtagaggagc aaacagcgtt  12720
tgcgacatcc ttttgtaata ctgcggaact gactaaagta gtgagttata cacagggctg  12780
ggatctattc tttttatctt tttttattct ttctttattc tataaattat aaccacttga  12840
atataaacaa aaaaaacaca caaaggtcta gcggaattta cagagggtct agcagaattt  12900
acaagttttc cagcaaaggt ctagcagaat ttacagatac ccacaactca aaggaaaagg  12960
actagtaatt atcattgact agcccatctc aattggtata gtgattaaaa tcacctagac  13020
caattgagat gtatgtctga attagttgtt ttcaaagcaa atgaactagc gattagtcgc  13080
tatgacttaa cggagcatga aaccaagcta attttatgct gtgtggcact actcaacccc  13140
acgattgaaa accctacaag gaaagaacgg acggtatcgt tcacttataa ccaatacgct  13200
cagatgatga acatcagtag ggaaaatgct tatggtgtat tagctaaagc aaccagagag  13260
ctgatgacga gaactgtgga aatcaggaat cctttggtta aaggctttga gattttccag  13320
tggacaaact atgccaagtt ctcaagcgaa aaattagaat tagtttttag tgaagagata  13380
ttgccttatc ttttccagtt aaaaaaattc ataaaatata atctggaaca tgttaagtct  13440
tttgaaaaca aatactctat gaggatttat gagtggttat taaaagaact aacacaaaag  13500
aaaactcaca aggcaaatat agagattagc cttgatgaat ttaagttcat gttaatgctt  13560
gaaaataact accatgagtt taaaaggctt aaccaatggg ttttgaaacc aataagtaaa  13620
gatttaaaca cttacagcaa tatgaaattg gtggttgata agcgaggccg cccgactgat  13680
acgttgattt tccaagttga actagataga caaatggatc tcgtaaccga acttgagaac  13740
aaccagataa aaatgaatgg tgacaaaata ccaacaacca ttacatcaga ttcctaccta  13800
cataacggac taagaaaaac actacacgat gctttaactg caaaaattca gctcaccagt  13860
tttgaggcaa aatttttgag tgacatgcaa agtaagtatg atctcaatgg ttcgttctca  13920
tggctcacgc aaaaacaacg aaccacacta gagaacatac tggctaaata cggaaggatc  13980
tgaggttctt atggctcttg tatctatcag tgaagcatca agactaacaa acaaaagtag  14040
aacaactgtt caccgttaca tatcaaaggg aaaactgtcc atatgcacag atgaaaacgg  14100
tgtaaaaaag atagatacat cagagctttt acgagttttt ggtgcattca aagctgttca  14160
ccatgaacag atcgacaatg taacagatga acagcatgta acacctaata gaacaggtga  14220
aaccagtaaa acaaagcaac tagaacatga aattgaacac ctgagacaac ttgttacagc  14280
tcaacagtca cacatagaca gcctgaaaca ggcgatgctg cttatcgaat caaagctgcc  14340
gacaacacgg gagccagtga cgcctcccgt ggggaaaaaa tcatggcaat tctggaagaa  14400
atagcgcttt cagccggcaa accggctgaa gccggatctg cga                    14443
```

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
ggatctaaag cagaaaaatc tgc 23

<210> SEQ ID NO 52
<211> LENGTH: 30
<212> TYPE: DNA
<213> ORGANISM: Artificial Sequnece
<220> FEATURE:
<223> OTHER INFORMATION: Primer

<400> SEQUENCE: 52
ttcaagctta aacaactgtt ctcccatacg 30

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
atgggaaaca catcaataca aacgc 25

<210> SEQ ID NO 54
<211> LENGTH: 30
<212> TYPE: DNA
<213> ORGANISM: Artificial Sequence
<220> FEATURE:
<223> OTHER INFORMATION: Primer

<400> SEQUENCE: 54
cagctgtcag ttagttgccg tttgagaacg 30

<210> SEQ ID NO 55
<211> LENGTH: 5770
<212> TYPE: DNA
<213> ORGANISM: Artificial Sequence
<220> FEATURE:
<223> OTHER INFORMATION: Plasmid

<400> SEQUENCE: 55
aaaaatagat tttatttttt tgatgcaggt caagattgac tcattagagg tatcggtgag 60
gagacactgg aagagaagag atcgttgtaa tgcttttcaa attaacgtaa agcgggtata 120
tttcggttgt tattagctgc gcagagggtg gcactctgtg gagcaaagcg gcgaaagccg 180
gacggcagaa tgcgccataa ggcattcagg agagatggca tttacgggca gtaagtcaga 240
agaccgaaga tgttccggaa gccataaaag gaaaaccccc acaatctttc gacgaacttg 300
gcgggacgga gaaagattat gggggcctca cagaatacgg gtaaagtata atgaaaccgt 360
accagagatt caaccctgtg cagtgtataa atacacggca caatcgctcc gccataagcg 420
acagcttgtg gcaggtctga agaatactcc atataacgca gtacactgga gtcagttagc 480
acccgaagag cagatccgtt tctgggaaga ctatgaagcg ggaagggcga ccactttcct 540
ggttgaaccg gaaaggaagc gcacgaagcg ccgtcgcggt gagcactcca ccaaacccaa 600
atgcgaaaat ccgtcctggt atcgtcctga gcgctataag gcgctgagcg ggcagctcgg 660
gcacgcctac aaccgtctgg tgaaaaagga cccggtgacc ggcgagcaga gcctgcgcat 720
gcacatgtct ctgcatcctt tttacgtgca gaaacgaacg tatgccggtc gcaaatatgc 780
tttccgtccg gaaaaacaac gcctcctcga tgccatctgg ccggttctgg tcagcttcag 840
tgatgcgggc acacataccg taggcatgag tgtttcccgt ctggccagag aaatcagccc 900

-continued

```
gaaagacagc aaggggaagg ttattccgga actggaagtg acggtctccc gcctttcccg    960
tttgctggcc gaacaggtac gttttggtgt gctgggtgtt tcagaggaaa ccctgtggga   1020
ccgtgaaacc cgccagcgtc tgccacgtta cgtctggata acaccggcag gctggcagat   1080
gctgggcgtc gacatggtaa aacttcacga acagcagcag aaacgactgc gtgaaagtga   1140
aatccgccag cagctcattc gggaaggtgt tctgcgtgag gatgaagata tctccgtaca   1200
tgcggccaga aaacgctggt atctgcagcg cagccaggat gcactgaaac accgtcgtgc   1260
aaaagcggca gccagtaagc gcgccagacg cctgaagaaa ctgcctgccg accagcagat   1320
tcatgagatg gcagagtatc tcaggaagcg tctgcctccg gatgaagcct atttttgttc   1380
cgatgaccat ctgaagcgaa tggccatcag ggagttgcgt cagcttgaac tgacgctggc   1440
tgccccgcca ccgcactaga cagcaccatt ccctcagcac tgaatcatca ccagcccctc   1500
cggggctttc ggcgctggtt ccgctcagcc caaaatccgc agtaatcacc ttaaatcccc   1560
tcagaggggc atatctgccc ataaaaccac gcatcagtca tcagaacatg gccacgtcgt   1620
ttcagttatc cacataaatc cgcaaacaaa gaactttaag aagctgcaaa cctgaaacag   1680
caaacctgca atatagtctt aaccccatta tttaatcccc tgcgttgctt cgccgcaggg   1740
aaaatcttta tctctgagac cactgtgaac aaatacaaag aggccttcgc ttgcagcggc   1800
caaggccgcg ccgctcagaa tctaaaagca cctcccacgc tgatgcgcgg gccccgaacc   1860
tcaccgttct gaaaccacaa caaaaaaaca tcaggaataa aaacaccaca caaacgcagc   1920
accgtaccca cccctcataa ctgaaaagcg aggccgcccc cgcccgaagg gcgggaacaa   1980
catcgctttt aattatgaat gttgtaacta cattgtcatc gctgccagtc ttctggctgg   2040
aagtcctcag tacacgctcg taagcggccc tgacggcccg ctaacgcgga gatacgcccc   2100
gactgcgggt aaacccttgt cgggaccact ccgaccgcgc acagaagcta tttcatggct   2160
gaagcgggta tggcttagca ggatggggat gggtaaggtg aaatctatca atcagtaccg   2220
gctgacgccg ggcttcggcg gttttgtttc tgtgccatat gtaacaacgg agtgccgcct   2280
tacatgcgct gacgcgcatt atttgccttg tttcgtctga aagtaatcac tatgattaaa   2340
tatgattaac agctaatcgg atatgcaaat gaaaaacaat accgcacaag caacaaaagt   2400
aattaccgcg catgtgccat tacctatggc tgataaagtc gaccagatgg ccgccagact   2460
ggaacgctcc cggggctgga ttatcaaaca ggcgctttct gcatggcttg cccaggagga   2520
ggagcgtaat cgcctgacgc tggaagccct ggacgatgtg acatccggac aggttatcga   2580
ccatcaggct gtacaggcct gggcggacag cctcagtact gacaatccgt taccggtgcc   2640
acgctgatgg aactgaagtg gaccagtaag gcgctttctg atttggcgcg gttatatgat   2700
tttctggtgc tgaccagtaa acctgcggcc gccagaacgg tgcagtccct gacacatgct   2760
ccggtcattc tgttaactca tccacgtatg ggagaacagt tgtttaagct cagctgtcag   2820
ttagttgccg tttgagaacg gaaacgggca aagataaaga tgaccgcgaa gcagagtgcg   2880
gggatcagtt cagcagtggg gatgttgccc gccgcgtcac tgacaaaacc catgaccgga   2940
gtgacaatac cgccgccaat aatggtcata acgatgaagg acgaaccata tttggtgtcc   3000
tggccgagat tcttaatgcc cagcgagaag attgttgggt actgaatcga cataaaggcg   3060
ctgcataaag tcagggctat taagcccaca tgaccgccag cgaaggctga gatcaggcac   3120
agtgccatag cgattaatgc gtaggcggcc aggactttgt gtggtgcgaa gcgactgatg   3180
agccaggtac cggtgaaacg accaataaag aagcacacca tggttccggt taaatagtta   3240
```

-continued

```
gcggcaaagc ctgcagtcat acctggaatt tcttctacag cgtagcgaat caaatagctc   3300
cagcaggccg tttgtgcgcc gacatagcag aattgcgcta ataccgccca gcgccagtgg   3360
cgaatacgcg ccaggcgaga aagcgatgcg gagaacgatc cttgtttggc gtcactgtga   3420
ttatcactct gcaatgccgg gaatttcgtc agcatgatca gcagggcgac cagtaacacg   3480
atagccacga tgatcatata aggtgtctgt accgataata ccaggctgtg tttatacgca   3540
ctcaattgct ctggagacat tttatcgaga acgtcttgcg attgatgtgg cacgttagac   3600
aaaataagac tttgcccaaa gacaaccgcg ataattgcgc caaacgagtt aaatgtttgc   3660
gcaagattta agcggaagtg accactactt tccggcccta ataccgtaac aaaagggttt   3720
gcggcagttt ccagacaacc taatccggct gcaataataa ataggccaac taaaaacaag   3780
gtgtagttca ttatttctgc ggcgggccag aataatgcag cacccaaggc atataaaaat   3840
aacccggtaa taatccctgc tttataactg agtttttca tcaatatccc agcagggatt   3900
gggataatga aataaccaaa gtaaaaggcc gattggatca ggccagcctg gaaatttgtc   3960
agcgtaaaag cctgctggaa ttgaggtaat aaaatgtcgt taaggttatt ggctaccgcc   4020
caaagaaaaa acagtgagca cagcagcgcg aatggaataa tgtaacttct gctttgccct   4080
gcatctttat ctaccgcacg gtaactctgc gtttgtattg atgtgtttcc catagcttgg   4140
ttacctccgg gaaacgcggt tgatttgttt agtggttgaa ttatttgctc aggatgtggc   4200
atagtcaagg gcgtgacggc tcgcctgact tctcgttcca gtgcccccgt ccgacagtcg   4260
agcgtgcgag cccataatct cgcgctggtg ctgcataccg tggcaaacag cacagatcgc   4320
ctagggaatt cggcactggc cgtcgtttta caacgtcgtg actgggaaaa ccctggcgtt   4380
acccaactta atcgccttgc agcacatccc cctttcgcca gctggcgtaa tagcgaagag   4440
gcccgcaccg atcgcccttc ccaacagttg cgcagcctga atggcgaatg gcgcgataag   4500
ctagcttcac gctgccgcaa gcactcaggg cgcaagggct gctaaaggaa gcggaacacg   4560
tagaaagcca gtccgcagaa acggtgctga ccccggatga atgtcagcta ctgggctatc   4620
tggacaaggg aaaacgcaag cgcaaagaga aagcaggtag cttgcagtgg gcttacatgg   4680
cgatagctag actgggcggt tttatggaca gcaagcgaac cggaattgcc agctggggcg   4740
ccctctggta aggttgggaa gccctgcaaa gtaaactgga tggctttctt gccgccaagg   4800
atctgatggc gcaggggatc aagatctgat caagagacag gatgaggatc gtttcgcatg   4860
attgaacaag atggattgca cgcaggttct ccggccgctt gggtggagag gctattcggc   4920
tatgactggg cacaacagac aatcggctgc tctgatgccg ccgtgttccg gctgtcagcg   4980
caggggcgcc cggttctttt tgtcaagacc gacctgtccg gtgccctgaa tgaactccaa   5040
gacgaggcag cgcggctatc gtggctggcc acgacgggcg ttccttgcgc agctgtgctc   5100
gacgttgtca ctgaagcggg aagggactgg ctgctattgg gcgaagtgcc ggggcaggat   5160
ctcctgtcat ctcaccttgc tcctgccgag aaagtatcca tcatggctga tgcaatgcgg   5220
cggctgcata cgcttgatcc ggctacctgc ccattcgacc accaagcgaa acatcgcatc   5280
gagcgagcac gtactcggat ggaagccggt cttgtcgatc aggatgatct ggacgaagag   5340
catcaggggc tcgcgccagc cgaactgttc gccaggctca aggcgcggat gcccgacggc   5400
gaggatctcg tcgtgaccca tggcgatgcc tgcttgccga atatcatggt ggaaaatggc   5460
cgcttttctg gattcatcga ctgtggccgg ctgggtgtgg cggaccgcta tcaggacata   5520
gcgttggcta cccgtgatat tgctgaagag cttggcggcg aatgggctga ccgcttcctc   5580
gtgctttacg gtatcgccgc tcccgattcg cagcgcatcg ccttctatcg ccttcttgac   5640
```

gagttcttct gagcgggact ctggggttcg cgatgataag ctgtcaaaca tgagaattac 5700
aacttatatc gtatggggct gacttcaggt gctacatttg aagagataaa ttgcactgaa 5760
atctagaaat 5770

<210> SEQ ID NO 56
<211> LENGTH: 5764
<212> TYPE: DNA
<213> ORGANISM: Artificial Sequence
<220> FEATURE:
<223> OTHER INFORMATION: Plasmid

<400> SEQUENCE: 56
agcttggtta cctccgggaa acgcggttga tttgtttagt ggttgaatta tttgctcagg 60
atgtggcatc gtcaagggcg tgacggctcg cctgacttct cgttccagtg cccccgtccg 120
acagtcgagc gtgcgagccc ataatctcgc gctggtgctg cataccgtgg caaacagcac 180
agatcgccta gggaattcgg cactggccgt cgttttacaa cgtcgtgact gggaaaaccc 240
tggcgttacc caacttaatc gccttgcagc acatccccct ttcgccagct ggcgtaatag 300
cgaagaggcc cgcaccgatc gcccttccca acagttgcgc agcctgaatg gcgaatggcg 360
cgataagcta gcttcacgct gccgcaagca ctcagggcgc aagggctgct aaaggaagcg 420
gaacacgtag aaagccagtc cgcagaaacg gtgctgaccc cggatgaatg tcagctactg 480
ggctatctgg acaagggaaa acgcaagcgc aaagagaaag caggtagctt gcagtgggct 540
tacatggcga tagctagact gggcggtttt atggacagca agcgaaccgg aattgccagc 600
tggggcgccc tctggtaagg ttgggaagcc ctgcaaagta aactggatgg ctttcttgcc 660
gccaaggatc tgatggcgca ggggatcaag atctgatcaa gagacaggat gaggatcgtt 720
tcgcatgatt gaacaagatg gattgcacgc aggttctccg gccgcttggg tggagaggct 780
attcggctat gactgggcac aacagacaat cggctgctct gatgccgccg tgttccggct 840
gtcagcgcag gggcgcccgg ttctttttgt caagaccgac ctgtccggtg ccctgaatga 900
actccaagac gaggcagcgc ggctatcgtg gctggccacg acgggcgttc cttgcgcagc 960
tgtgctcgac gttgtcactg aagcgggaag ggactggctg ctattgggcg aagtgccggg 1020
gcaggatctc ctgtcatctc accttgctcc tgccgagaaa gtatccatca tggctgatgc 1080
aatgcggcgg ctgcatacgc ttgatccggc tacctgccca ttcgaccacc aagcgaaaca 1140
tcgcatcgag cgagcacgta ctcggatgga agccggtctt gtcgatcagg atgatctgga 1200
cgaagagcat caggggctcg cgccagccga actgttcgcc aggctcaagg cgcggatgcc 1260
cgacggcgag gatctcgtcg tgacccatgg cgatgcctgc ttgccgaata tcatggtgga 1320
aaatggccgc ttttctggat tcatcgactg tggccggctg ggtgtggcgg accgctatca 1380
ggacatagcg ttggctaccc gtgatattgc tgaagagctt ggcggcgaat gggctgaccg 1440
cttcctcgtg ctttacggta tcgccgctcc cgattcgcag cgcatcgcct tctatcgcct 1500
tcttgacgag ttcttctgag cgggactctg gggttcgcga tgataagctg tcaaacatga 1560
gaattacaac ttatatcgta tggggctgac ttcaggtgct acatttgaag agataaattg 1620
cactgaaatc tagaaataaa aatagatttt atttttttga tgcaggtcaa gattgactca 1680
ttagaggtat cggtgaggag acactggaag agaagagatc gttgtaatgc ttttcaaatt 1740
aacgtaaagc gggtatattt cggttgttat tagctgcgca gagggtggca ctctgtggag 1800
caaagcggcg aaagccggac ggcagaatgc gccataaggc attcaggaga gatggcattt 1860

-continued acgggcagta agtcagaaga ccgaagatgt tccggaagcc ataaaaggaa aacccccaca 1920
atctttcgac gaacttggcg ggacggagaa agattatggg ggcctcacag aatacgggta 1980
aagtataatg aaaccgtacc agagattcaa ccctgtgcag tgtataaata cacggcacaa 2040
tcgctccgcc ataagcgaca gcttgtggca ggtctgaaga atactccata taacgcagta 2100
cactggagtc agttagcacc cgaagagcag atccgtttct gggaagacta tgaagcggga 2160
agggcgacca ctttcctggt tgaaccggaa aggaagcgca cgaagcgccg tcgcggtgag 2220
cactccacca aacccaaatg cgaaaatccg tcctggtatc gtcctgagcg ctataaggcg 2280
ctgagcgggc agctcgggca cgcctacaac cgtctggtga aaaaggaccc ggtgaccggc 2340
gagcagagcc tgcgcatgca catgtctctg catccttttt acgtgcagaa acgaacgtat 2400
gccggtcgca aatatgcttt ccgtccggaa aaacaacgcc tcctcgatgc catctggccg 2460
gttctggtca gcttcagtga tgcgggcaca cataccgtag gcatgagtgt ttcccgtctg 2520
gccagagaaa tcagcccgaa agacagcaag ggaaggtta ttccggaact ggaagtgacg 2580
gtctcccgcc tttcccgttt gctggccgaa caggtacgtt ttggtgtgct gggtgtttca 2640
gaggaaaccc tgtgggaccg tgaaacccgc cagcgtctgc cacgttacgt ctggataaca 2700
ccggcaggct ggcagatgct gggcgtcgac atggtaaaac ttcacgaaca gcagcagaaa 2760
cgactgcgtg aaagtgaaat ccgccagcag ctcattcggg aaggtgttct gcgtgaggat 2820
gaagatatct ccgtacatgc ggccagaaaa cgctggtatc tgcagcgcag ccaggatgca 2880
ctgaaacacc gtcgtgcaaa agcggcagcc agtaagcgcg ccagacgcct gaagaaactg 2940
cctgccgacc agcagattca tgagatggca gagtatctca ggaagcgtct gcctccggat 3000
gaagcctatt tttgttccga tgaccatctg aagcgaatgg ccatcaggga gttgcgtcag 3060
cttgaactga cgctggctgc cccgccaccg cactagacag caccattccc tcagcactga 3120
atcatcacca gcccctccgg ggctttcggc gctggttccg ctcagcccaa aatccgcagt 3180
aatcacctta aatcccctca gaggggcata tctgcccata aaaccacgca tcagtcatca 3240
gaacatggcc acgtcgtttc agttatccac ataaatccgc aaacaaagaa ctttaagaag 3300
ctgcaaacct gaaacagcaa acctgcaata tagtcttaac cccattattt aatcccctgc 3360
gttgcttcgc cgcagggaaa atctttatct ctgagaccac tgtgaacaaa tacaaagagg 3420
ccttcgcttg cagcggccaa ggccgcgccg ctcagaatct aaaagcacct cccacgctga 3480
tgcgcgggcc ccgaacctca ccgttctgaa accacaacaa aaaaacatca ggaataaaaa 3540
caccacacaa acgcagcacc gtacccaccc ctcataactg aaaagcgagg ccgcccccgc 3600
ccgaagggcg ggaacaacat cgcttttaat tatgaatgtt gtaactacat tgtcatcgct 3660
gccagtcttc tggctggaag tcctcagtac acgctcgtaa gcggccctga cggcccgcta 3720
acgcggagat acgccccgac tgcgggtaaa cccttgtcgg gaccactccg accgcgcaca 3780
gaagctattt catggctgaa gcgggtatgg cttagcagga tggggatggg taaggtgaaa 3840
tctatcaatc agtaccggct gacgccgggc ttcggcggtt ttgtttctgt gccatatgta 3900
acaacggagt gccgccttac atgcgctgac gcgcattatt tgccttgttt cgtctgaaag 3960
taatcactat gattaaatat gattaacagc taatcggata tgcaaatgaa aaacaatacc 4020
gcacaagcaa caaaagtaat taccgcgcat gtgccattac ctatggctga taaagtcgac 4080
cagatggccg ccagactgga acgctcccgg ggctggatta tcaaacaggc gctttctgca 4140
tggcttgccc aggaggagga gcgtaatcgc ctgacgctgg aagccctgga cgatgtgaca 4200
tccggacagg ttatcgacca tcaggctgta caggcctggg cggacagcct cagtactgac 4260
aatccgttac cggtgccacg ctgatggaac tgaagtggac cagtaaggcg ctttctgatt 4320
tggcgcggtt atatgatttt ctggtgctga ccagtaaacc tgcggccgcc agaacggtgc 4380
agtccctgac acatgctccg gtcattctgt taactcatcc acgtatggga gaacagttgt 4440
ttaagcttca gttagttgcc gtttgagaac ggaaacgggc aaagataaag atgaccgcga 4500
agcagagtgc ggggatcagt tcagcagtgg ggatgttgcc cgccgcgtca ctgacaaaac 4560
ccatgaccgg agtgacaata ccgccgccaa taatggtcat aacgatgaag gacgaaccat 4620
atttggtgtc ctggccgaga ttcttaatgc ccagcgagaa gattgttggg tactgaatcg 4680
acataaaggc gctgcataaa gtcagggcta ttaagcccac atgaccgcca gcgaaggctg 4740
agatcaggca cagtgccata gcgattaatg cgtaggcggc caggactttg tgtggtgcga 4800
agcgactgat gagccaggta ccggtgaaac gaccaataaa gaagcacacc atggttccgg 4860
ttaaatagtt agcggcaaag cctgcagtca tacctggaat ttcttctaca gcgtagcgaa 4920
tcaaatagct ccagcaggcc gtttgtgcgc cgacatagca gaattgcgct aataccgccc 4980
agcgccagtg gcgaatacgc gccaggcgag aaagcgatgc ggagaacgat ccttgtttgg 5040
cgtcactgtg attatcactc tgcaatgccg ggaatttcgt cagcatgatc agcagggcga 5100
ccagtaacac gatagccacg atgatcatat aaggtgtctg taccgataat accaggctgt 5160
gtttatacgc actcaattgc tctggagaca ttttatcgag aacgtcttgc gattgatgtg 5220
gcacgttaga caaaataaga ctttgcccaa agacaaccgc gataattgcg ccaaacgagt 5280
taaatgtttg cgcaagattt aagcggaagt gaccactact ttccggccct aataccgtaa 5340
caaaagggtt tgcggcagtt tccagacaac ctaatccggc tgcaataata aataggccaa 5400
ctaaaaacaa ggtgtagttc attatttctg cggcgggcca gaataatgca gcacccaagg 5460
catataaaaa taacccggta ataatccctg ctttataact gagttttttc atcaatatcc 5520
cagcagggat tgggataatg aaataaccaa agtaaaaggc cgattggatc aggccagcct 5580
ggaaatttgt cagcgtaaaa gcctgctgga attgaggtaa taaaatgtcg ttaaggttat 5640
tggctaccgc ccaaagaaaa aacagtgagc acagcagcgc gaatggaata atgtaacttc 5700
tgctttgccc tgcatcttta tctaccgcac ggtaactctg cgtttgtatt gatgtgtttc 5760
ccat 5764

<210> SEQ ID NO 57
<211> LENGTH: 109
<212> TYPE: DNA
<213> ORGANISM: Artificial Sequence
<220> FEATURE:
<223> OTHER INFORMATION: Synthetic Linker

<400> SEQUENCE: 57
actgacaatc cgttaccggt gccacgctga tggaactgaa gtggaccagt aaggcgcttt 60
ctgatttggc gcggttatat gattttctgg tgctgaccag taaacctgc 109

<210> SEQ ID NO 58
<211> LENGTH: 5695
<212> TYPE: DNA
<213> ORGANISM: Artificial Sequence
<220> FEATURE:
<223> OTHER INFORMATION: Plasmid

<400> SEQUENCE: 58
gtgaccggcg agcagagcct gcgcatgcac atgtctctgc atccttttta cgtgcagaaa 60

-continued

```
cgaacgtatg ccggtcgcaa atatgctttc cgtccggaaa aacaacgcct cctcgatgcc    120
atctggccgg ttctggtcag cttcagtgat gcgggcacac ataccgtagg catgagtgtt    180
tcccgtctgg ccagagaaat cagcccgaaa gacagcaagg ggaaggttat tccggaactg    240
gaagtgacgg tctcccgcct ttcccgtttg ctggccgaac aggtacgttt tggtgtgctg    300
ggtgtttcag aggaaaccct gtgggaccgt gaaacccgcc agcgtctgcc acgttacgtc    360
tggataacac cggcaggctg gcagatgctg ggcgtcgaca tggtaaaact tcacgaacag    420
cagcagaaac gactgcgtga aagtgaaatc cgccagcagc tcattcggga aggtgttctg    480
cgtgaggatg aagatatctc cgtacatgcg gccagaaaac gctggtatct gcagcgcagc    540
caggatgcac tgaaacaccg tcgtgcaaaa gcggcagcca gtaagcgcgc cagacgcctg    600
aagaaactgc ctgccgacca gcagattcat gagatggcag agtatctcag gaagcgtctg    660
cctccggatg aagcctattt ttgttccgat gaccatctga agcgaatggc catcagggag    720
ttgcgtcagc ttgaactgac gctggctgcc ccgccaccgc actagacagc accattccct    780
cagcactgaa tcatcaccag cccctccggg gctttcggcg ctggttccgc tcagcccaaa    840
atccgcagta atcaccttaa atcccctcag aggggcatat ctgcccataa aaccacgcat    900
cagtcatcag aacatggcca cgtcgtttca gttatccaca taaatccgca aacaaagaac    960
tttaagaagc tgcaaacctg aaacagcaaa cctgcaatat agtcttaacc ccattattta   1020
atcccctgcg ttgcttcgcc gcagggaaaa tctttatctc tgagaccact gtgaacaaat   1080
acaaagaggc cttcgcttgc agcggccaag gccgcgccgc tcagaatcta aaagcacctc   1140
ccacgctgat gcgcgggccc cgaacctcac cgttctgaaa ccacaacaaa aaaacatcag   1200
gaataaaaac accacacaaa cgcagcaccg tacccacccc tcataactga aaagcgaggc   1260
cgcccccgcc cgaagggcgg gaacaacatc gcttttaatt atgaatgttg taactacatt   1320
gtcatcgctg ccagtcttct ggctggaagt cctcagtaca cgctcgtaag cggccctgac   1380
ggcccgctaa cgcggagata cgccccgact gcgggtaaac ccttgtcggg accactccga   1440
ccgcgcacag aagctatttc atggctgaag cgggtatggc ttagcaggat ggggatgggt   1500
aaggtgaaat ctatcaatca gtaccggctg acgccgggct tcggcggttt tgtttctgtg   1560
ccatatgtaa caacggagtg ccgccttaca tgcgctgacg cgcattattt gccttgtttc   1620
gtctgaaagt aatcactatg attaaatatg attaacagct aatcggatat gcaaatgaaa   1680
aacaataccg cacaagcaac aaaagtaatt accgcgcatg tgccattacc tatggctgat   1740
aaagtcgacc agatggccgc cagactggaa cgctcccggg gctggattat caaacaggcg   1800
ctttctgcat ggcttgccca ggaggaggag cgtaatcgcc tgacgctgga agccctggac   1860
gatgtgacat ccggacaggt tatcgaccat caggctgtac aggcctgggc ggacagcctc   1920
agtactgttt aaacgtaagg cgctttctga tttgggcggc cgccagaacg gtgcagtccc   1980
tgacacatgc tccggtcatt ctgttaactc atccacgtat gggagaacag ttgtttaagc   2040
tcagctgtca gttagttgcc gtttgagaac ggaaacgggc aaagataaag atgaccgcga   2100
agcagagtgc ggggatcagt tcagcagtgg ggatgttgcc cgccgcgtca ctgacaaaac   2160
ccatgaccgg agtgacaata ccgccgccaa taatggtcat aacgatgaag gacgaaccat   2220
atttggtgtc ctggccgaga ttcttaatgc ccagcgagaa gattgttggg tactgaatcg   2280
acataaaggc gctgcataaa gtcagggcta ttaagcccac atgaccgcca gcgaaggctg   2340
agatcaggca cagtgccata gcgattaatg cgtaggcggc caggactttg tgtggtgcga   2400
agcgactgat gagccaggta ccggtgaaac gaccaataaa gaagcacacc atggttccgg   2460
```

ttaaatagtt agcggcaaag cctgcagtca tacctggaat ttcttctaca gcgtagcgaa 2520
tcaaatagct ccagcaggcc gtttgtgcgc cgacatagca gaattgcgct aataccgccc 2580
agcgccagtg gcgaatacgc gccaggcgag aaagcgatgc ggagaacgat ccttgtttgg 2640
cgtcactgtg attatcactc tgcaatgccg ggaatttcgt cagcatgatc agcagggcga 2700
ccagtaacac gatagccacg atgatcatat aaggtgtctg taccgataat accaggctgt 2760
gtttatacgc actcaattgc tctggagaca ttttatcgag aacgtcttgc gattgatgtg 2820
gcacgttaga caaaataaga ctttgcccaa agacaaccgc gataattgcg ccaaacgagt 2880
taaatgtttg cgcaagattt aagcggaagt gaccactact ttccggccct aataccgtaa 2940
caaaagggtt tgcggcagtt tccagacaac ctaatccggc tgcaataata aataggccaa 3000
ctaaaaacaa ggtgtagttc attatttctg cggcgggcca gaataatgca gcacccaagg 3060
catataaaaa taacccggta ataatccctg ctttataact gagtttttc atcaatatcc 3120 cagcagggat tgggataatg aaataaccaa agtaaaaggc cgattggatc aggccagcct 3180
ggaaatttgt cagcgtaaaa gcctgctgga attgaggtaa taaaatgtcg ttaaggttat 3240
tggctaccgc ccaaagaaaa aacagtgagc acagcagcgc gaatggaata atgtaacttc 3300
tgctttgccc tgcatcttta tctaccgcac ggtaactctg cgtttgtatt gatgtgtttc 3360
ccatagcttg gttacctccg ggaaacgcgg ttgatttgtt tagtggttga attatttgct 3420
caggatgtgg cattgtcaag ggcgtgacgg ctcgcctgac ttctcgttcc agtgcccccg 3480
tccgacagtc gagcgtgcga gcccataatc tcgcgctggt gctgcatacc gtggcaaaca 3540
gcacagatcg cctagggaat tcggcactgg ccgtcgtttt acaacgtcgt gactgggaaa 3600
accctggcgt tacccaactt aatcgccttg cagcacatcc ccctttcgcc agctggcgta 3660
atagcgaaga ggcccgcacc gatcgccctt cccaacagtt gcgcagcctg aatggcgaat 3720
ggcgcgataa gctagcttca cgctgccgca agcactcagg gcgcaagggc tgctaaagga 3780
agcggaacac gtagaaagcc agtccgcaga aacggtgctg accccggatg aatgtcagct 3840
actgggctat ctggacaagg gaaaacgcaa gcgcaaagag aaagcaggta gcttgcagtg 3900
ggcttacatg gcgatagcta gactgggcgg ttttatggac agcaagcgaa ccggaattgc 3960
cagctggggc gccctctggt aaggttggga agccctgcaa agtaaactgg atggctttct 4020
tgccgccaag gatctgatgg cgcaggggat caagatctga tcaagagaca ggatgaggat 4080
cgtttcgcat gattgaacaa gatggattgc acgcaggttc tccggccgct tgggtggaga 4140
ggctattcgg ctatgactgg gcacaacaga caatcggctg ctctgatgcc gccgtgttcc 4200
ggctgtcagc gcaggggcgc ccggttcttt ttgtcaagac cgacctgtcc ggtgccctga 4260
atgaactcca agacgaggca gcgcggctat cgtggctggc cacgacgggc gttccttgcg 4320
cagctgtgct cgacgttgtc actgaagcgg gaagggactg gctgctattg ggcgaagtgc 4380
cggggcagga tctcctgtca tctcaccttg ctcctgccga gaaagtatcc atcatggctg 4440
atgcaatgcg gcggctgcat acgcttgatc cggctacctg cccattcgac caccaagcga 4500
aacatcgcat cgagcgagca cgtactcgga tggaagccgg tcttgtcgat caggatgatc 4560
tggacgaaga gcatcagggg ctcgcgccag ccgaactgtt cgccaggctc aaggcgcgga 4620
tgcccgacgg cgaggatctc gtcgtgaccc atggcgatgc ctgcttgccg aatatcatgg 4680
tggaaaatgg ccgcttttct ggattcatcg actgtggccg gctgggtgtg gcggaccgct 4740
atcaggacat agcgttggct acccgtgata ttgctgaaga gcttggcggc gaatgggctg 4800

-continued

```
accgcttcct cgtgctttac ggtatcgccg ctcccgattc gcagcgcatc gccttctatc   4860

gccttcttga cgagttcttc tgagcgggac tctggggttc gcgatgataa gctgtcaaac   4920

atgagaatta caacttatat cgtatggggc tgacttcagg tgctacattt gaagagataa   4980

attgcactga aatctagaaa taaaaataga ttttattttt ttgatgcagg tcaagattga   5040

ctcattagag gtatcggtga ggagacactg gaagagaaga gatcgttgta atgcttttca   5100

aattaacgta aagcgggtat atttcggttg ttattagctg cgcagagggt ggcactctgt   5160

ggagcaaagc ggcgaaagcc ggacggcaga atgcgccata aggcattcag gagagatggc   5220

atttacgggc agtaagtcag aagaccgaag atgttccgga agccataaaa ggaaaacccc   5280

cacaatcttt cgacgaactt ggcgggacgg agaaagatta tgggggcctc acagaatacg   5340

ggtaaagtat aatgaaaccg taccagagat tcaaccctgt gcagtgtata aatacacggc   5400

acaatcgctc cgccataagc gacagcttgt ggcaggtctg aagaatactc catataacgc   5460

agtacactgg agtcagttag cacccgaaga gcagatccgt ttctgggaag actatgaagc   5520

gggaagggcg accactttcc tggttgaacc ggaaaggaag cgcacgaagc gccgtcgcgg   5580

tgagcactcc accaaaccca aatgcgaaaa tccgtcctgg tatcgtcctg agcgctataa   5640

ggcgctgagc gggcagctcg ggcacgccta caaccgtctg gtgaaaaagg acccg        5695
```

```
<210> SEQ ID NO 59
<211> LENGTH: 34
<212> TYPE: DNA
<213> ORGANISM: Artificial Sequence
<220> FEATURE:
<223> OTHER INFORMATION: Primer

<400> SEQUENCE: 59

ccctactgta taaaaaagct taagaggata gctc                                  34


<210> SEQ ID NO 60
<211> LENGTH: 28
<212> TYPE: DNA
<213> ORGANISM: Artificial Sequence
<220> FEATURE:
<223> OTHER INFORMATION: Primer

<400> SEQUENCE: 60

aacgcgttaa ctcactgacc tgatagcc                                         28


<210> SEQ ID NO 61
<211> LENGTH: 5815
<212> TYPE: DNA
<213> ORGANISM: Artificial Sequence
<220> FEATURE:
<223> OTHER INFORMATION: Plasmid

<400> SEQUENCE: 61

agcttaagag gatagctcaa tgagtacgct aatcacggat aaggtcgata acgcagcggt     60

ccaaaaagaa aaactggaca ccagtgcgta tttaccccat accccctggc tgcaattttt    120

actggtctgt tgcctgtttg cgctatgggg gatggcgggc aacctgaatg atattttgat    180

cgcccagttt aaaaagggct tcgatttaac ggatacccag acagcgctgg tgcagtcgat    240

tttttcctc ggctactttt ttgtcgccct gcccgcggcg gcgctgatta agcgtttctc    300

ctataaagcg gcgattatta ttgggctgtg cctgtacgcc ctcggctgct tcctgttcgt    360

tccggccgca cagatcatga cctacggcgc attcctcgcc tgcctcggag tgatcgcctg    420

cggactctct tttctggaaa cgtcggcaaa cacctactcc agcctgctgg gtccgattca    480
```

```
atcctccacc cagcgtatta acttttcgca gatcttcaac tcgctgggcg tgatctccgg    540
cgtattaatt ggccagctga tggtctttgg cgaaaacgat ccgagtcatg aacaactgct    600
ggcgatgccc gccgccgctg cagacgttgc acgccatcag atggttggtc aggtggtcgg    660
gccctatctg attatcggct ccgtactggt ggtgctggcg ctggtgttcg tgtttattaa    720
attcccgtcg tgcaagggcg cgcccgctca acagcaacaa ctcccgacgg aaagcatggg    780
gccaacgctg aaacgcctgt ttgctatccc gcgctttcgc ctcgggatcc tgtcgcagtt    840
tttgtacgtc ggcgcccagg ttggcgtatg gagcttcacg attcgctttg tgcagctcgt    900
gcagcaaggc accagcgagc actccgcgac ttactggctg ctggcttctc tggtgattta    960
cgccgtggga aaaaccgtgg ccacctggtt gatgaaccgt ctgaatccgg cgatgctgct   1020
cggaacgttt gccctggccg ccaccgccct gttactgatt gccgttttca gcggttcaat   1080
gctggcggtc tatgcgctca ttctggtcag cttctgtatg gcgccatgct ggccgacgaa   1140
ctttggtctg gtgatcaaag ggatggggaa agatacccag accgcaggct cgatcgtggt   1200
gatgtcgatt atcggcgggg ccgtaattcc gctggtgatg ggcattatct cggatatgaa   1260
cggcggcaat atgcaaatcg cctttatcgc tccgctcctg tgctttgtgt atgtcgcttt   1320
ctacggcttc tggtgcgtgc gtaagggggt ataacatgcg cgaacttatc aacacgattg   1380
ctcatattgg ctatcaggtc agtgagttaa cagaatgacc ggagcatgtg tcagggactg   1440
caccgttctg gcggccgcag gtttactggt cagcaccaga aaatcatata accgcgccaa   1500
atcagaaagc gccttactgg tccacttcag ttccatcagc gtggcaccgg taacggattg   1560
tcagtactga ggctgtccgc ccaggcctgt acagcctgat ggtcgataac ctgtccggat   1620
gtcacatcgt ccagggcttc cagcgtcagg cgattacgct cctcctcctg ggcaagccat   1680
gcagaaagcg cctgtttgat aatccagccc cgggagcgtt ccagtctggc ggccatctgg   1740
tcgactttat cagccatagg taatggcaca tgcgcggtaa ttacttttgt tgcttgtgcg   1800
gtattgtttt tcatttgcat atccgattag ctgttaatca tatttaatca tagtgattac   1860
tttcagacga aacaaggcaa ataatgcgcg tcagcgcatg taaggcggca ctccgttgtt   1920
acatatggca cagaaacaaa accgccgaag cccggcgtca gccggtactg attgatagat   1980
ttcaccttac ccatccccat cctgctaagc catacccgct tcagccatga aatagcttct   2040
gtgcgcggtc ggagtggtcc cgacaagggt ttacccgcag tcggggcgta tctccgcgtt   2100
agcgggccgt cagggccgct tacgagcgtg tactgaggac ttccagccag aagactggca   2160
gcgatgacaa tgtagttaca acattcataa ttaaaagcga tgttgttccc gcccttcggg   2220
cgggggcggc ctcgcttttc agttatgagg ggtgggtacg gtgctgcgtt tgtgtggtgt   2280
ttttattcct gatgtttttt tgttgtggtt tcagaacggt gaggttcggg gcccgcgcat   2340
cagcgtggga ggtgctttta gattctgagc ggcgcggcct tggccgctgc aagcgaaggc   2400
ctctttgtat ttgttcacag tggtctcaga gataaagatt ttccctgcgg cgaagcaacg   2460
caggggatta aataatgggg ttaagactat attgcaggtt tgctgtttca ggtttgcagc   2520
ttcttaaagt tctttgtttg cggatttatg tggataactg aaacgacgtg gccatgttct   2580
gatgactgat gcgtggtttt atgggcagat atgcccctct gaggggattt aaggtgatta   2640
ctgcggattt tgggctgagc ggaaccagcg ccgaaagccc cggaggggct ggtgatgatt   2700
cagtgctgag ggaatggtgc tgtctagtgc ggtggcgggg cagccagcgt cagttcaagc   2760
tgacgcaact ccctgatggc cattcgcttc agatggtcat cggaacaaaa ataggcttca   2820
```

-continued

```
tccggaggca gacgcttcct gagatactct gccatctcat gaatctgctg gtcggcaggc   2880
agtttcttca ggcgtctggc gcgcttactg gctgccgctt ttgcacgacg gtgtttcagt   2940
gcatcctggc tgcgctgcag ataccagcgt tttctggccg catgtacgga gatatcttca   3000
tcctcacgca gaacaccttc ccgaatgagc tgctggcgga tttcactttc acgcagtcgt   3060
ttctgctgct gttcgtgaag ttttaccatg tcgacgccca gcatctgcca gcctgccggt   3120
gttatccaga cgtaacgtgg cagacgctgg cgggtttcac ggtcccacag ggtttcctct   3180
gaaacaccca gcacaccaaa acgtacctgt tcggccagca aacgggaaag gcgggagacc   3240
gtcacttcca gttccggaat aaccttcccc ttgctgtctt tcgggctgat ttctctggcc   3300
agacgggaaa cactcatgcc tacggtatgt gtgcccgcat cactgaagct gaccagaacc   3360
ggccagatgg catcgaggag gcgttgtttt tccggacgga aagcatattt gcgaccggca   3420
tacgttcgtt tctgcacgta aaaaggatgc agagacatgt gcatgcgcag gctctgctcg   3480
ccggtcaccg ggtccttttt caccagacgg ttgtaggcgt gcccgagctg cccgctcagc   3540
gccttatagc gctcaggacg ataccaggac ggattttcgc atttgggttt ggtggagtgc   3600
tcaccgcgac ggcgcttcgt gcgcttcctt tccggttcaa ccaggaaagt ggtcgccctt   3660
cccgcttcat agtcttccca gaaacggatc tgctcttcgg gtgctaactg actccagtgt   3720
actgcgttat atggagtatt cttcagacct gccacaagct gtcgcttatg gcggagcgat   3780
tgtgccgtgt atttatacac tgcacagggt tgaatctctg gtacggtttc attatacttt   3840
acccgtattc tgtgaggccc ccataatctt tctccgtccc gccaagttcg tcgaaagatt   3900
gtgggggttt tccttttatg gcttccggaa catcttcggt cttctgactt actgcccgta   3960
aatgccatct ctcctgaatg ccttatggcg cattctgccg tccggctttc gccgctttgc   4020
tccacagagt gccaccctct gcgcagctaa taacaaccga aatatacccg ctttacgtta   4080
atttgaaaag cattacaacg atctcttctc ttccagtgtc tcctcaccga tacctctaat   4140
gagtcaatct tgacctgcat caaaaaaata aaatctattt ttatttctag atttcagtgc   4200
aatttatctc ttcaaatgta gcacctgaag tcagccccat acgatataag ttgtaattct   4260
catgtttgac agcttatcat cgcgaacccc agagtcccgc tcagaagaac tcgtcaagaa   4320
ggcgatagaa ggcgatgcgc tgcgaatcgg gagcggcgat accgtaaagc acgaggaagc   4380
ggtcagccca ttcgccgcca agctcttcag caatatcacg ggtagccaac gctatgtcct   4440
gatagcggtc cgccacaccc agccggccac agtcgatgaa tccagaaaag cggccatttt   4500
ccaccatgat attcggcaag caggcatcgc catgggtcac gacgagatcc tcgccgtcgg   4560
gcatccgcgc cttgagcctg gcgaacagtt cggctggcgc gagcccctga tgctcttcgt   4620
ccagatcatc ctgatcgaca agaccggctt ccatccgagt acgtgctcgc tcgatgcgat   4680
gtttcgcttg gtggtcgaat gggcaggtag ccggatcaag cgtatgcagc cgccgcattg   4740
catcagccat gatggatact ttctcggcag gagcaaggtg agatgacagg agatcctgcc   4800
ccggcacttc gcccaatagc agccagtccc ttcccgcttc agtgacaacg tcgagcacag   4860
ctgcgcaagg aacgcccgtc gtggccagcc acgatagccg cgctgcctcg tcttggagtt   4920
cattcagggc accggacagg tcggtcttga caaaaagaac cgggcgcccc tgcgctgaca   4980
gccggaacac ggcggcatca gagcagccga ttgtctgttg tgcccagtca tagccgaata   5040
gcctctccac ccaagcggcc ggagaacctg cgtgcaatcc atcttgttca atcatgcgaa   5100
acgatcctca tcctgtctct tgatcagatc ttgatcccct gcgccatcag atccttggcg   5160
gcaagaaagc catccagttt actttgcagg gcttcccaac cttaccagag ggcgccccag   5220
```

ctggcaattc cggttcgctt gctgtccata aaaccgccca gtctagctat cgccatgtaa 5280
gcccactgca agctacctgc tttctctttg cgcttgcgtt ttcccttgtc cagatagccc 5340
agtagctgac attcatccgg ggtcagcacc gtttctgcgg actggctttc tacgtgttcc 5400
gcttccttta gcagcccttg cgccctgagt gcttgcggca gcgtgaagct agcttatcgc 5460
gccattcgcc attcaggctg cgcaactgtt gggaagggcg atcggtgcgg gcctcttcgc 5520
tattacgcca gctggcgaaa gggggatgtg ctgcaaggcg attaagttgg gtaacgccag 5580
ggttttccca gtcacgacgt tgtaaaacga cggccagtgc cgaattccct aggcgatctg 5640
tgctgtttgc cacggtatgc agcaccagcg cgagattatg ggctcgcacg ctcgactgtc 5700
ggacgggggc actggaacga gaagtcaggc gagccgtcac gcccttgact atgccacatc 5760
ctgagcaaat aattcaacca ctaaacaaat caaccgcgtt tcccggaggt aacca 5815

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
aagcgccaag cttgggaggg gagaggtcgc 30

<210> SEQ ID NO 63
<211> LENGTH: 27
<212> TYPE: DNA
<213> ORGANISM: Artificial Sequence
<220> FEATURE:
<223> OTHER INFORMATION: Primer

<400> SEQUENCE: 63
tactgcgcag ttaacgccgc atcgtcg 27

<210> SEQ ID NO 64
<211> LENGTH: 5789
<212> TYPE: DNA
<213> ORGANISM: Artificial Sequence
<220> FEATURE:
<223> OTHER INFORMATION: Plasmid

<400> SEQUENCE: 64
agcttgggag gggagaggtc gcatgcatta cagcgatacc gccgcgtcac cgcgcggcaa 60
cctggcgcgt accgccgtgg tgcccctgtt gttgatcgtc agcctgtttt ttctatgggg 120
catggcgaac aacctcaacg acatcctgat caagcagttc aagaaggcct tcgagctgtc 180
cgacctgcag gccgggctgg tgcagagcgc tttctacctg ggctatttcg tgttcgcgat 240
gccagcggcg atgttcatgc gccgctacag ctacaaggcc gcggtggtgc tgggcctgct 300
gctatatgcc tgcggcgcgt tcctgttcta tccggccgcg caggtgcaca cctactggct 360
gttcctgctg gcgttgttcg tgatcgccag cggcctggcg tttctggaaa ccaccgccaa 420
tccgctggtc accgtgctgg gcccggccga cggcgcggcg cggcggctca atcttgcgca 480
ggccttcaat ccgctgggct cgatcaccgg cgtgctggtg ggccagcatt tcattttctc 540
cggcgtggag cacaccccag ccgagctggc ggcgatggcg ccggccgcgc gcgaggcctt 600
cttcgccacc gaatcctcag cggtgcagat gccctatctg atcatcggcg tggtggtggt 660
gctgtgggcg atcctgatcg cgctggtgcg cttcccaacc ggcgacgccg gcgtgggcac 720

-continued

```
ggcggccccc aagcgtgcca agttcggcga attgctgcgt aaccggctgt tcgtgttttc    780
ggtggtggcg cagttcttct acgtgggcgc gcaggtcggc atctggagtt atttgattcg    840
ctacctgcag gatgcggtcc ccggtacgcc ggaaaaaagc gcggccacct atctgacgat    900
ctcgctggtg ctattcatgg ccgggcgctt tgtcggcacc gcactgctgc gctatctggc    960
gccggccaag ttgctggcca gctttgccac gatcaatctg ctgctgtgcg cagtcgcgat   1020
tgccttgccg ggctggactg gcctgtatgc gctggttgcg gccagcgtgt tcatgtcggt   1080
aatgttcccg accatcttcg cgctgggcct ggatggcatg cacgatgacg cacgcaagct   1140
ggggtcttcg ttgctggtga tggccatcat tggtggcgcc ttgctcactg cgctcatggg   1200
tgcggtgtcg gacatggccg gcatccattg ggcaatggtg gtgcccggtg tgtgcttcgg   1260
cgtgatcctg ctgttcgcgt tgcgtgcccg tcgtgctgcg cctgtggtgg cgggggcatg   1320
agcatgcagc ggctgtgcta tgtgctggat ctgcacgacg atgcggcgtt aactgcgcag   1380
taaacagaat gaccggagca tgtgtcaggg actgcaccgt tctggcggcc gcaggtttac   1440
tggtcagcac cagaaaatca tataaccgcg ccaaatcaga aagcgcctta ctggtccact   1500
tcagttccat cagcgtggca ccggtaacgg attgtcagta ctgaggctgt ccgcccaggc   1560
ctgtacagcc tgatggtcga taacctgtcc ggatgtcaca tcgtccaggg cttccagcgt   1620
caggcgatta cgctcctcct cctgggcaag ccatgcagaa agcgcctgtt tgataatcca   1680
gccccgggag cgttccagtc tggcggccat ctggtcgact ttatcagcca taggtaatgg   1740
cacatgcgcg gtaattactt ttgttgcttg tgcggtattg tttttcattt gcatatccga   1800
ttagctgtta atcatattta atcatagtga ttactttcag acgaaacaag gcaaataatg   1860
cgcgtcagcg catgtaaggc ggcactccgt tgttacatat ggcacagaaa caaaaccgcc   1920
gaagcccggc gtcagccggt actgattgat agatttcacc ttacccatcc ccatcctgct   1980
aagccatacc cgcttcagcc atgaaatagc ttctgtgcgc ggtcggagtg gtcccgacaa   2040
gggtttaccc gcagtcgggg cgtatctccg cgttagcggg ccgtcagggc cgcttacgag   2100
cgtgtactga ggacttccag ccagaagact ggcagcgatg acaatgtagt tacaacattc   2160
ataattaaaa gcgatgttgt tcccgccctt cgggcggggg cggcctcgct tttcagttat   2220
gaggggtggg tacggtgctg cgtttgtgtg gtgtttttat tcctgatgtt tttttgttgt   2280
ggtttcagaa cggtgaggtt cggggcccgc gcatcagcgt gggaggtgct tttagattct   2340
gagcggcgcg gccttggccg ctgcaagcga aggcctcttt gtatttgttc acagtggtct   2400
cagagataaa gattttccct gcggcgaagc aacgcagggg attaaataat ggggttaaga   2460
ctatattgca ggtttgctgt ttcaggtttg cagcttctta aagttctttg tttgcggatt   2520
tatgtggata actgaaacga cgtggccatg ttctgatgac tgatgcgtgg ttttatgggc   2580
agatatgccc ctctgagggg atttaaggtg attactgcgg attttgggct gagcggaacc   2640
agcgccgaaa gccccggagg ggctggtgat gattcagtgc tgagggaatg gtgctgtcta   2700
gtgcggtggc ggggcagcca gcgtcagttc aagctgacgc aactccctga tggccattcg   2760
cttcagatgg tcatcggaac aaaaataggc ttcatccgga ggcagacgct tcctgagata   2820
ctctgccatc tcatgaatct gctggtcggc aggcagtttc ttcaggcgtc tggcgcgctt   2880
actggctgcc gcttttgcac gacggtgttt cagtgcatcc tggctgcgct gcagatacca   2940
gcgttttctg gccgcatgta cggagatatc ttcatcctca cgcagaacac cttcccgaat   3000
gagctgctgg cggatttcac tttcacgcag tcgtttctgc tgctgttcgt gaagttttac   3060
catgtcgacg cccagcatct gccagcctgc cggtgttatc cagacgtaac gtggcagacg   3120
```

```
ctggcgggtt tcacggtccc acagggtttc ctctgaaaca cccagcacac caaaacgtac   3180
ctgttcggcc agcaaacggg aaaggcggga gaccgtcact tccagttccg gaataacctt   3240
ccccttgctg tctttcgggc tgatttctct ggccagacgg gaaacactca tgcctacggt   3300
atgtgtgccc gcatcactga agctgaccag aaccggccag atggcatcga ggaggcgttg   3360
tttttccgga cggaaagcat atttgcgacc ggcatacgtt cgtttctgca cgtaaaaagg   3420
atgcagagac atgtgcatgc gcaggctctg ctcgccggtc accgggtcct tttcaccag    3480
acggttgtag gcgtgcccga gctgcccgct cagcgcctta tagcgctcag gacgatacca   3540
ggacggattt tcgcatttgg gtttggtgga gtgctcaccg cgacggcgct tcgtgcgctt   3600
cctttccggt tcaaccagga aagtggtcgc ccttcccgct tcatagtctt cccagaaacg   3660
gatctgctct tcgggtgcta actgactcca gtgtactgcg ttatatggag tattcttcag   3720
acctgccaca agctgtcgct tatggcggag cgattgtgcc gtgtatttat acactgcaca   3780
gggttgaatc tctggtacgg tttcattata ctttacccgt attctgtgag gcccccataa   3840
tctttctccg tcccgccaag ttcgtcgaaa gattgtgggg gttttccttt tatggcttcc   3900
ggaacatctt cggtcttctg acttactgcc cgtaaatgcc atctctcctg aatgccttat   3960
ggcgcattct gccgtccggc tttcgccgct ttgctccaca gagtgccacc ctctgcgcag   4020
ctaataacaa ccgaaatata cccgctttac gttaatttga aaagcattac aacgatctct   4080
tctcttccag tgtctcctca ccgatacctc taatgagtca atcttgacct gcatcaaaaa   4140
aataaaatct atttttattt ctagatttca gtgcaattta tctcttcaaa tgtagcacct   4200
gaagtcagcc ccatacgata taagttgtaa ttctcatgtt tgacagctta tcatcgcgaa   4260
ccccagagtc ccgctcagaa gaactcgtca agaaggcgat agaaggcgat gcgctgcgaa   4320
tcgggagcgg cgataccgta aagcacgagg aagcggtcag cccattcgcc gccaagctct   4380
tcagcaatat cacgggtagc caacgctatg tcctgatagc ggtccgccac acccagccgg   4440
ccacagtcga tgaatccaga aaagcggcca ttttccacca tgatattcgg caagcaggca   4500
tcgccatggg tcacgacgag atcctcgccg tcgggcatcc gcgccttgag cctggcgaac   4560
agttcggctg gcgcgagccc ctgatgctct tcgtccagat catcctgatc gacaagaccg   4620
gcttccatcc gagtacgtgc tcgctcgatg cgatgtttcg cttggtggtc gaatgggcag   4680
gtagccggat caagcgtatg cagccgccgc attgcatcag ccatgatgga tactttctcg   4740
gcaggagcaa ggtgagatga caggagatcc tgccccggca cttcgcccaa tagcagccag   4800
tcccttcccg cttcagtgac aacgtcgagc acagctgcgc aaggaacgcc cgtcgtggcc   4860
agccacgata gccgcgctgc ctcgtcttgg agttcattca gggcaccgga caggtcggtc   4920
ttgacaaaaa gaaccgggcg cccctgcgct gacagccgga acacggcggc atcagagcag   4980
ccgattgtct gttgtgccca gtcatagccg aatagcctct ccacccaagc ggccggagaa   5040
cctgcgtgca atccatcttg ttcaatcatg cgaaacgatc ctcatcctgt ctcttgatca   5100
gatcttgatc ccctgcgcca tcagatcctt ggcggcaaga aagccatcca gtttactttg   5160
cagggcttcc caaccttacc agagggcgcc ccagctggca attccggttc gcttgctgtc   5220
cataaaaccg cccagtctag ctatcgccat gtaagcccac tgcaagctac ctgctttctc   5280
tttgcgcttg cgttttccct tgtccagata gcccagtagc tgacattcat ccggggtcag   5340
caccgtttct gcggactggc tttctacgtg ttccgcttcc tttagcagcc cttgcgccct   5400
gagtgcttgc ggcagcgtga agctagctta tcgcgccatt cgccattcag gctgcgcaac   5460
```

```
tgttgggaag ggcgatcggt gcgggcctct tcgctattac gccagctggc gaaaggggga   5520

tgtgctgcaa ggcgattaag ttgggtaacg ccagggtttt cccagtcacg acgttgtaaa   5580

acgacggcca gtgccgaatt ccctaggcga tctgtgctgt ttgccacggt atgcagcacc   5640

agcgcgagat tatgggctcg cacgctcgac tgtcggacgg gggcactgga acgagaagtc   5700

aggcgagccg tcacgccctt gactatgcca catcctgagc aaataattca accactaaac   5760

aaatcaaccg cgtttcccgg aggtaacca                                     5789
```

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65

```
gatgaggatg ctatgggaaa cac                                             23
```

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66

```
ggataaatgt tcagtttgtc gccgc                                           25
```

<210> SEQ ID NO 67
<211> LENGTH: 5786
<212> TYPE: DNA
<213> ORGANISM: Artificial Sequence
<220> FEATURE:
<223> OTHER INFORMATION: Plasmid

<400> SEQUENCE: 67

```
gatgaggatg ctatgggaaa cacaacaata caaacacaga gttttcgtgc tgtggatgca     60

gagcaaagca aaagcaagcg ctacattatt ccattcgcct tactttgctc gctatttttt    120

ctgtgggccg tcgccaataa tctgaatgac attttattac cgcagtttca acaagctttt    180

acgctaacta actttcaggc cgggcttatt cagtcagcct tttatttcgg ttatttcgtc    240

attccaattc ccgctgggat tttgatgaaa aaactcagtt ataaagcagg gattatcacc    300

ggactttttt tgtatgctgt tggcgccgca ttattctggc ctgccgccga gataatgaat    360

tacacattgt ttttaattgg cctgtttatc atcgccgccg gtttaggctg ccttgaaact    420

gcggccaacc cttttgttac ggtattaggt ccagaaagcg gcggacattt ccggcttaat    480

ctggcgcaaa cttttaactc ctttggcgct attatcgccg ttgtgtttgg gcaaagcctt    540

attttgtcta acgtgccgca tcaatcgcaa gaagcgcttg ataaaatgac gccggatcag    600

cttagcgcct ataaacacag cctggtgtta tcggtacaaa cgccatacat gattatcgtc    660

gccatcgtat tagtagttgc gctactgatt atgctgacca aatttccggc cctgcaaagt    720

gacgatcata gcgatgctaa acaaagctct ttcttatctt ctctctcccg actcatccgt    780

atccgccact ggcgctgggc ggtgctggcg cagttctgct acgtgggggc gcaaaccgcc    840

tgctggagct atctgatccg ctacgccatt gaggagatcc ctggaatgac gcccggtttc    900

gccgccaatt acctgaccgg cacgatggtg tgcttcttta tcggccgttt caccgggacc    960

tggcttatca gccgcttcgc gccgcataaa gtgctggccg cctacgccct gtttgccatg   1020
```

-continued

```
ctcctgtgtc tgatttccgc ctttagcggc ggacatatcg gcctgctggc gctgacgttg   1080
tgtagcgcat ttatgtcaat ccagtacccg accatcttct cgctgggtat caaaaatctg   1140
ggacaggaca ctaagtacgg ctcgtctttt atcgtcatga ccatcattgg cggcggtatt   1200
gtcacgccag taatgggctt cgttagcgac gccgcaggca aaatcccgac cgccgaactg   1260
gttccggcat tgtgctttgc cgtcatcttc atttttgccc gtttccgttc acaagcggcg   1320
acaaactgaa catttatcca gcttaaacaa ctgttctccc atacgtggat gagttaacag   1380
aatgaccgga gcatgtgtca gggactgcac cgttctggcg gccgcaggtt tactggtcag   1440
caccagaaaa tcatataacc gcgccaaatc agaaagcgcc ttactggtcc acttcagttc   1500
catcagcgtg gcaccggtaa cggattgtca gtactgaggc tgtccgccca ggcctgtaca   1560
gcctgatggt cgataacctg tccggatgtc acatcgtcca gggcttccag cgtcaggcga   1620
ttacgctcct cctcctgggc aagccatgca gaaagcgcct gtttgataat ccagccccgg   1680
gagcgttcca gtctggcggc catctggtcg actttatcag ccataggtaa tggcacatgc   1740
gcggtaatta cttttgttgc ttgtgcggta ttgtttttca tttgcatatc cgattagctg   1800
ttaatcatat ttaatcatag tgattacttt cagacgaaac aaggcaaata atgcgcgtca   1860
gcgcatgtaa ggcggcactc cgttgttaca tatggcacag aaacaaaacc gccgaagccc   1920
ggcgtcagcc ggtactgatt gatagatttc accttaccca tccccatcct gctaagccat   1980
acccgcttca gccatgaaat agcttctgtg cgcggtcgga gtggtcccga caagggttta   2040
cccgcagtcg gggcgtatct ccgcgttagc gggccgtcag ggccgcttac gagcgtgtac   2100
tgaggacttc cagccagaag actggcagcg atgacaatgt agttacaaca ttcataatta   2160
aaagcgatgt tgttcccgcc cttcgggcgg gggcggcctc gcttttcagt tatgaggggt   2220
gggtacggtg ctgcgtttgt gtggtgtttt tattcctgat gttttttttgt tgtggtttca   2280
gaacggtgag gttcggggcc cgcgcatcag cgtgggaggt gcttttagat tctgagcggc   2340
gcggccttgg ccgctgcaag cgaaggcctc tttgtatttg ttcacagtgg tctcagagat   2400
aaagattttc cctgcggcga agcaacgcag gggattaaat aatggggtta agactatatt   2460
gcaggtttgc tgtttcaggt ttgcagcttc ttaaagttct ttgtttgcgg atttatgtgg   2520
ataactgaaa cgacgtggcc atgttctgat gactgatgcg tggttttatg ggcagatatg   2580
cccctctgag ggatttaag gtgattactg cggattttgg gctgagcgga accagcgccg   2640
aaagccccgg aggggctggt gatgattcag tgctgaggga atggtgctgt ctagtgcggt   2700
ggcggggcag ccagcgtcag ttcaagctga cgcaactccc tgatggccat tcgcttcaga   2760
tggtcatcgg aacaaaaata ggcttcatcc ggaggcagac gcttcctgag atactctgcc   2820
atctcatgaa tctgctggtc ggcaggcagt ttcttcaggc gtctggcgcg cttactggct   2880
gccgcttttg cacgacggtg tttcagtgca tcctggctgc gctgcagata ccagcgtttt   2940
ctggccgcat gtacggagat atcttcatcc tcacgcagaa caccttcccg aatgagctgc   3000
tggcggattt cactttcacg cagtcgtttc tgctgctgtt cgtgaagttt taccatgtcg   3060
acgcccagca tctgccagcc tgccggtgtt atccagacgt aacgtggcag acgctggcgg   3120
gtttcacggt cccacagggt ttcctctgaa acacccagca caccaaaacg tacctgttcg   3180
gccagcaaac gggaaaggcg ggagaccgtc acttccagtt ccggaataac cttccccttg   3240
ctgtctttcg ggctgatttc tctggccaga cgggaaacac tcatgcctac ggtatgtgtg   3300
cccgcatcac tgaagctgac cagaaccggc cagatggcat cgaggaggcg ttgtttttcc   3360
```

-continued ggacggaaag catatttgcg accggcatac gttcgtttct gcacgtaaaa aggatgcaga 3420
gacatgtgca tgcgcaggct ctgctcgccg gtcaccgggt cctttttcac cagacggttg 3480
taggcgtgcc cgagctgccc gctcagcgcc ttatagcgct caggacgata ccaggacgga 3540
ttttcgcatt tgggtttggt ggagtgctca ccgcgacggc gcttcgtgcg cttcctttcc 3600
ggttcaacca ggaaagtggt cgcccttccc gcttcatagt cttcccagaa acggatctgc 3660
tcttcgggtg ctaactgact ccagtgtact gcgttatatg gagtattctt cagacctgcc 3720
acaagctgtc gcttatggcg gagcgattgt gccgtgtatt tatacactgc acagggttga 3780
atctctggta cggtttcatt atactttacc cgtattctgt gaggccccca taatctttct 3840
ccgtcccgcc aagttcgtcg aaagattgtg ggggttttcc ttttatggct tccggaacat 3900
cttcggtctt ctgacttact gcccgtaaat gccatctctc ctgaatgcct tatggcgcat 3960
tctgccgtcc ggctttcgcc gctttgctcc acagagtgcc accctctgcg cagctaataa 4020
caaccgaaat atacccgctt tacgttaatt tgaaaagcat tacaacgatc tcttctcttc 4080
cagtgtctcc tcaccgatac ctctaatgag tcaatcttga cctgcatcaa aaaaataaaa 4140
tctattttta tttctagatt tcagtgcaat ttatctcttc aaatgtagca cctgaagtca 4200
gccccatacg atataagttg taattctcat gtttgacagc ttatcatcgc gaaccccaga 4260
gtcccgctca gaagaactcg tcaagaaggc gatagaaggc gatgcgctgc gaatcgggag 4320
cggcgatacc gtaaagcacg aggaagcggt cagcccattc gccgccaagc tcttcagcaa 4380
tatcacgggt agccaacgct atgtcctgat agcggtccgc cacacccagc cggccacagt 4440
cgatgaatcc agaaaagcgg ccattttcca ccatgatatt cggcaagcag gcatcgccat 4500
gggtcacgac gagatcctcg ccgtcgggca tccgcgcctt gagcctggcg aacagttcgg 4560
ctggcgcgag cccctgatgc tcttcgtcca gatcatcctg atcgacaaga ccggcttcca 4620
tccgagtacg tgctcgctcg atgcgatgtt tcgcttggtg gtcgaatggg caggtagccg 4680
gatcaagcgt atgcagccgc cgcattgcat cagccatgat ggatactttc tcggcaggag 4740
caaggtgaga tgacaggaga tcctgccccg gcacttcgcc caatagcagc cagtcccttc 4800
ccgcttcagt gacaacgtcg agcacagctg cgcaaggaac gcccgtcgtg gccagccacg 4860
atagccgcgc tgcctcgtct tggagttcat tcagggcacc ggacaggtcg gtcttgacaa 4920
aaagaaccgg gcgcccctgc gctgacagcc ggaacacggc ggcatcagag cagccgattg 4980
tctgttgtgc ccagtcatag ccgaatagcc tctccaccca agcggccgga gaacctgcgt 5040
gcaatccatc ttgttcaatc atgcgaaacg atcctcatcc tgtctcttga tcagatcttg 5100
atcccctgcg ccatcagatc cttggcggca agaaagccat ccagtttact ttgcagggct 5160
tcccaacctt accagagggc gccccagctg gcaattccgg ttcgcttgct gtccataaaa 5220
ccgcccagtc tagctatcgc catgtaagcc cactgcaagc tacctgcttt ctctttgcgc 5280
ttgcgttttc ccttgtccag atagcccagt agctgacatt catccggggt cagcaccgtt 5340
tctgcggact ggctttctac gtgttccgct tcctttagca gcccttgcgc cctgagtgct 5400
tgcggcagcg tgaagctagc ttatcgcgcc attcgccatt caggctgcgc aactgttggg 5460
aagggcgatc ggtgcgggcc tcttcgctat tacgccagct ggcgaaaggg ggatgtgctg 5520
caaggcgatt aagttgggta acgccagggt tttcccagtc acgacgttgt aaaacgacgg 5580
ccagtgccga attccctagg cgatctgtgc tgtttgccac ggtatgcagc accagcgcga 5640
gattatgggc tcgcacgctc gactgtcgga cgggggcact ggaacgagaa gtcaggcgag 5700
ccgtcacgcc cttgactatg ccacatcctg agcaaataat tcaaccacta aacaaatcaa 5760

-continued

```
ccgcgtttcc cggaggtaac caagct                                     5786


<210> SEQ ID NO 68
<211> LENGTH: 100
<212> TYPE: DNA
<213> ORGANISM: Artificial Sequence
<220> FEATURE:
<223> OTHER INFORMATION: Primer

<400> SEQUENCE: 68

cgtctaccct tgttatacct cacaccgcaa ggagacgatc atgaccaata atcccccttc     60

agcacagatt aagcccggcg gtgtaggctg gagctgcttc                          100


<210> SEQ ID NO 69
<211> LENGTH: 100
<212> TYPE: DNA
<213> ORGANISM: Artificial Sequence
<220> FEATURE:
<223> OTHER INFORMATION: Primer

<400> SEQUENCE: 69

gcatcaggca atgaataccc aatgcgacca gcttcttata tcagaacagc cccaacggtt     60

tatccgagta gctcaccagc catatgaata tcctccttag                          100


<210> SEQ ID NO 70
<211> LENGTH: 22
<212> TYPE: DNA
<213> ORGANISM: Artificial sequence
<220> FEATURE:
<223> OTHER INFORMATION: Primer

<400> SEQUENCE: 70

atgaccaata atcccccttc ag                                              22


<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71

gcttcttata tcagaacagc c                                               21
```